(12) United States Patent
Luo

(10) Patent No.: US 7,741,350 B1
(45) Date of Patent: Jun. 22, 2010

(54) BICYCLIC PYRAZOLO-HETEROCYCLES

(75) Inventor: Robert Zhiyong Luo, New City, NY (US)

(73) Assignee: Cara Therapeutics, Inc., Shelton, CT (US)

(*) Notice: Subject to any disclaimer, the term of this patent is extended or adjusted under 35 U.S.C. 154(b) by 0 days.

(21) Appl. No.: 12/582,417

(22) Filed: Oct. 20, 2009

Related U.S. Application Data

(60) Provisional application No. 61/147,808, filed on Jan. 28, 2009, provisional application No. 61/169,045, filed on Apr. 14, 2009.

(51) Int. Cl.
| | |
|---|---|
| A61K 31/425 | (2006.01) |
| A61K 31/42  | (2006.01) |
| A61K 31/415 | (2006.01) |
| A61K 31/40  | (2006.01) |
| A61K 31/35  | (2006.01) |
| C07D 277/00 | (2006.01) |
| C07D 413/12 | (2006.01) |
| C07D 487/04 | (2006.01) |
| C07D 207/06 | (2006.01) |
| C07D 311/94 | (2006.01) |

(52) U.S. Cl. ............... 514/371; 514/380; 514/406; 514/423; 514/456; 548/196; 548/246; 548/360.5; 548/518; 549/396

(58) Field of Classification Search .......... 514/371, 514/380, 406, 423, 456; 548/196, 246, 360.5, 548/518; 549/396
See application file for complete search history.

(56) References Cited

U.S. PATENT DOCUMENTS

| 3,004,983   | A  | 10/1961 | Loev           |
| 5,104,442   | A  | 4/1992  | Schutze et al. |
| 5,262,293   | A  | 11/1993 | Ikesu et al.   |
| 6,977,262   | B2 | 12/2005 | Kohara et al.  |
| 2003/0018023 | A1 | 1/2003 | Pinto et al.    |
| 2005/0176796 | A1 | 8/2005 | D'Allessio et al. |
| 2006/0069116 | A1 | 3/2006 | Ashton et al.   |
| 2007/0249597 | A1 | 10/2007 | Penning et al. |
| 2008/0070933 | A1 | 3/2008 | Huang           |
| 2009/0023756 | A1 | 1/2009 | Allen           |
| 2009/0137655 | A1 | 5/2009 | Scanlan et al. |
| 2009/0176825 | A1 | 7/2009 | Fitch           |

FOREIGN PATENT DOCUMENTS

| JP | 57-021388 A1 | 4/1982 |
| WO | 96/12720 A1 | 5/1996 |
| WO | 00/69846 A1 | 11/2000 |
| WO | 2003070706 A1 | 8/2003 |
| WO | 2004/013144 A1 | 2/2004 |
| WO | 2004/014374 A1 | 2/2004 |
| WO | 2004014910 A1 | 2/2004 |
| WO | WO 2004/013144 | * 2/2004 |
| WO | WO 2004/014374 | * 2/2004 |
| WO | 2006129178 A2 | 12/2006 |
| WO | 2008036445 A1 | 3/2008 |
| WO | 2009010824 A1 | 1/2009 |
| WO | 2009/106980 A1 | 9/2009 |
| WO | 2009/120660 A1 | 10/2009 |

OTHER PUBLICATIONS

Chemical Abstracts Service Registry Compound 1022511-88-1, Accessed 2009.
Chemical Abstracts Service Registry Compound 641625-85-6, Accessed 2009.
Chemical Abstracts Service Registry Compound 585514-80-3, Accessed 2009.
Chemical Abstracts Service Registry Compound 583812-76-4, Accessed 2009.
CAS Registry Compound No. 339347-66-9, Accessed 2009.
CAS Registry Compound No. 82037-49-8, Accessed 2009.
CAS Registry Compound No. 82048-84-8, Accessed 2009.
Muthusubramanian et al., Synthesis of Bromonaphthopyranoisoxazoles and pyrazoles as potential antimicrobial agents, Eur. J. Med. Chem.-Chim. Ther., 21(2) 163-66 (1986).

* cited by examiner

*Primary Examiner*—Joseph R Kosack
(74) *Attorney, Agent, or Firm*—Algis Anilionis

(57) ABSTRACT

The present invention provides substituted pyrazolo-heterocycles having the general structure of formula I

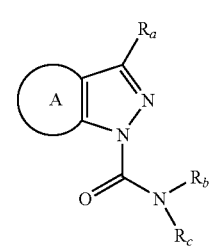

(I)

Also provided are pharmaceutically acceptable salts, acid salts, hydrates, solvates and stereoisomers of the compounds of formula I. The compounds are useful as modulators of cannabinoid receptors and for the prophylaxis and treatment of cannabinoid receptor-associated diseases and conditions, such as pain, inflammation and pruritis.

19 Claims, 1 Drawing Sheet

BICYCLIC PYRAZOLO-HETEROCYCLES

RELATED APPLICATIONS

This application claims the benefit of U.S. Provisional applications with Ser. No. 61/147,808 filed Jan. 28, 2009 and 61/169,045 filed Apr. 14, 2009 the entire specifications of which are expressly incorporated herein by reference.

FIELD OF THE INVENTION

The invention relates to substituted pyrazolo-heterocycles, and the use of these compounds in the prophylaxis and treatment of cannabinoid receptor-associated diseases, disorders and conditions, such as pain, inflammation and pruritis.

BACKGROUND OF THE INVENTION

Classical cannabinoids such as the marijuana-derived compound $\Delta^9$-tetra-hydro-cannabinol, ($\Delta^9$-THC) exert their pharmacological effects through interaction with specific members of the G-protein coupled receptor (GPCR) family. Two cannabinoid receptors have been cloned and characterized: CB1, a receptor found in the mammalian brain and to a lesser extent in peripheral tissues; and CB2, a receptor found primarily in the peripheral tissues, particularly in cells of the immune system.

Compounds that are modulators of one or both of the cannabinoid receptors have been shown to produce a variety of pharmacological effects that may be of therapeutic benefit in humans (see, for example, Mackie, K., *Cannabinoid receptors as therapeutic targets*, Ann. Rev. Pharmacol. Toxicol. (2006) 46: 101-122; Pertwee, R. G., Amer. Assoc. Pharm. Sci. J. (2005) 7:E625-654). The cannabinoid receptor modulator can be an agonist, an inverse agonist or a neutral antagonist, and may interact at the same (orthosteric) site as the endogenous ligand, or at a different (allosteric) site.

Activation of the CB1 receptor in the brain is believed to mediate undesirable psychotropic effects associated with $\Delta^9$-THC and other centrally acting cannabinoid ligands. As a result, there has been considerable interest in developing compounds that possess high affinity and selectivity for the CB2 receptor (see for example, Raitio, K. H. et al., Curr. Med. Chem. (2005) 12: 1217-37). CB2 receptor agonists have shown efficacy in preclinical models of neuropathic and inflammatory pain and may also find application in cancer, multiple sclerosis, osteoporosis, Alzheimer's disease, liver disease and diabetes (Mackie, K.; Ross R A; Br. J. Pharmacol. (2008) 153: 177-78 and refs cited therein). There is an ongoing need to identify new cannabinoid receptor ligands that exhibit improved drug-like properties. In addition there is a need for new cannabinoid ligands that are restricted to the periphery with low or minimal effects on the central nervous system (CNS).

SUMMARY OF THE INVENTION

The present invention provides compounds having the structure of formula I:

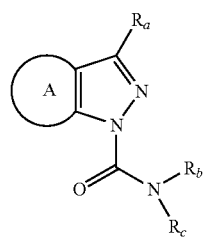

(I)

wherein the ring moiety A is chosen from:

(i)

(ii)

and (iii)

;

wherein V, W, X, Y and Z are each independently chosen from oxygen, $NR_1$ and $CR_1R_2$, provided that only one of V, W, X, Y and Z can be oxygen or $NR_1$.

The radical $R_a$ of formula I is selected from the group consisting of $C_1$-$C_8$ alkyl, $C_3$-$C_8$ cycloalkyl, $C_4$-$C_8$ cycloalkenyl, $(CH_2)_p$aryl, $(CH_2)_p$-linked 4-, 5-, 6-, 7-, 8-, 9- and 10-membered heterocyclyl; wherein the $C_1$-$C_8$ alkyl, $C_3$-$C_8$ cycloalkyl, $C_4$-$C_8$ cycloalkenyl, aryl, 4-, 5-, 6-, 7-, 8-, 9- and 10-membered heterocyclyl of $R_a$ are each optionally substituted with one to four substituents independently chosen from halo, hydroxyl, oxo, amino, nitro, cyano, COOH, $OCF_3$, $CF_3$, $C_1$-$C_6$ alkyl, $C_1$-$C_4$ alkoxy, $C_4$-$C_8$ alkenyl, $C_3$-$C_6$ cycloalkyl, aryl and 4-, 5-, 6-, 7-, 8-, 9- and 10-membered heterocyclyl.

In formula I, the radical $R_b$ is chosen from hydrogen and $C_1$-$C_6$ alkyl optionally substituted with one to four substituents independently chosen from $C_1$-$C_4$ alkoxy, halo, hydroxyl, amino and cyano.

The radical $R_c$ of formula I is $CR_dR_eR_f$ or $C_3$-$C_{10}$ cycloalkyl, 4-, 5-, 6- 7- 8-, 9- or 10-membered heterocyclyl; wherein the $C_3$-$C_{10}$ cycloalkyl, 4-, 5-, 6- 7- 8-, 9, or 10-membered heterocyclyl of $R_c$ is optionally substituted with one to four substituents independently selected from the group consisting of halo, hydroxyl, oxo, amino, nitro, cyano, COOH, $OCF_3$, $CF_3$, $C_1$-$C_4$ alkyl, $C_1$-$C_4$ alkoxy, $C_3$-$C_6$ cycloalkyl, $NR_1R_2$, $CONR_1R_2$, $SOR_1$, $SO_2R_1$, $SO_2NR_1R_2$, $CO_2R_1$, $NR_1SO_2R_2$ and $NR_1COR_2$.

The radical $R_d$ of formula I is chosen from hydrogen, $C_1$-$C_6$ alkyl, $C_3$-$C_8$ cycloalkyl, $(CH_2)_p$aryl, $(CH_2)_p$-linked 4-, 5-, 6-, 7-, 8-, 9- and 10-membered heterocyclyl; wherein the $C_1$-$C_6$ alkyl, $C_3$-$C_8$ cycloalkyl, $(CH_2)_p$aryl and $(CH_2)_p$-linked 4-, 5-, 6-, 7-, 8-, 9- and 10-membered heterocyclyl of $R_d$ are optionally substituted with one to four substituents independently chosen from $C_1$-$C_4$ alkyl, $C_1$-$C_4$ alkoxy, $C_1$-$C_4$ hydroxyalkyl, $C_1$-$C_4$ haloalkyl, $C_1$-$C_4$ haloalkoxy, aryl, halo, hydroxyl, amino, cyano, nitro and $CONR_1R_2$.

Alternatively, radicals $R_b$ and $R_d$ taken together with the nitrogen atom and carbon atom to which they are respectively bonded form a 4-, 5-, 6- 7- 8-, 9, or 10-membered heterocyclyl, which 4-, 5-, 6- 7- 8-, 9, or 10-membered heterocyclyl is optionally substituted with one to three substituents independently chosen from halo, hydroxyl, oxo $C_1$-$C_4$ alkyl, $C_1$-$C_4$ alkoxy, $C_1$-$C_4$ hydroxyalkyl, $COOR_1$, $CONR_1R_2$, $SOR_1$, $SO_2R_1$, $SO_2NR_1R_2$, $NR_1COR_2$ and $NR_1SO_2R_2$.

In formula I, the radical $R_e$ is chosen from hydrogen, $C_1$-$C_8$ alkyl, $C_3$-$C_6$ alkenyl, $C_3$-$C_6$ alkynyl, aryl, $C_3$-$C_8$ cycloalkyl, $C_4$-$C_8$ cycloalkenyl, $C_1$-$C_6$ hydroxyalkyl, $COR_3$, $CONR_3R_4$, $COOR_3$, $CONR_3R_4$, $CSNR_3R_4$, $SOR_3$, $SO_2R_3$, $SO_2NR_3R_4$, $NR_3SO_2R_4$, $NR_3COR_4$ and $(CH_2)_p$-linked 4-, 5-, 6-, 7-, 8-, 9- and 10-membered heterocyclyl; wherein the $C_1$-$C_8$ alkyl, $C_3$-$C_6$ alkenyl, $C_3$-$C_6$ alkynyl, aryl, $C_3$-$C_8$ cycloalkyl, $C_4$-$C_8$ cycloalkenyl, and $(CH_2)_p$-linked heterocyclyl of $R_e$ are each optionally substituted with one to four substituents independently chosen from halo, hydroxyl, oxo, amino, nitro, cyano, $OCF_3$, $CF_3$, $C_1$-$C_4$ alkyl, $C_1$-$C_4$ alkoxy, $C_1$-$C_4$ hydroxyalkyl, $C_3$-$C_6$ cycloalkyl, aryl, $CONR_1R_2$, $SOR_1$, $SO_2R_1$, $SO_2NR_1R_2$, $COOR_1$ and $NR_1SO_2R_2$.

The radical $R_f$ of formula I is chosen from hydrogen, $C_1$-$C_6$ alkyl and $C_1$-$C_8$ hydroxyalkyl. Alternatively, radicals $R_d$ and $R_f$ taken together with the carbon atom to which they are bonded form a $C_3$-$C_8$ cycloalkyl, or 4-, 5-, 6- 7- 8-, 9, or 10-membered heterocyclyl, which $C_3$-$C_8$ cycloalkyl or 4-, 5-, 6- 7- 8-, 9, or 10-membered heterocyclyl formed is optionally substituted with one to three substituents independently chosen from $C_1$-$C_4$ alkyl, $C_1$-$C_4$ alkoxy, $C_1$-$C_4$ hydroxyalkyl, $CONR_1R_2$, halo, hydroxyl and oxo.

In formula I, each instance of substituent $R_1$ and substituent $R_2$ is independently chosen from hydrogen, $C_1$-$C_6$ alkyl, $C_2$-$C_6$ alkenyl, $C_3$-$C_8$ alkynyl and $C_3$-$C_8$ cycloalkyl; wherein the $C_1$-$C_6$ alkyl, $C_2$-$C_6$ alkenyl, $C_3$-$C_8$ alkynyl and $C_3$-$C_8$ cycloalkyl of each $R_1$ and each $R_2$ is optionally substituted with one to four substituents independently chosen from $C_1$-$C_4$ alkyl, $C_1$-$C_4$ alkoxy, halo, hydroxyl, oxo, nitro, CN, $OCF_3$, $CF_3$, $NR_3R_4$, $CONR_3R_4$, $COOR_3$, $SOR_3$, $SO_2R_3$, $SO_2NR_3R_4$, $NR_3COR_4$ and $NR_3SO_2R_4$. Alternatively, the substituents $R_1$ and $R_2$ taken together with the carbon or nitrogen atom to which they are both bonded form a $C_3$-$C_8$ cycloalkyl, $C_4$-$C_8$ cycloalkenyl or a 3- to 8-membered heterocyclyl; wherein the $C_3$-$C_8$ cycloalkyl, $C_4$-$C_8$ cycloalkenyl or 3- to 8-membered heterocyclyl is optionally substituted with one to three substituents independently chosen from $C_1$-$C_4$ alkyl, $C_1$-$C_4$ alkoxy, halo, hydroxyl, oxo, amino, nitro, cyano, $OCF_3$, and $CF_3$.

In formula I, substituents $R_3$ and $R_4$ are each independently chosen from hydrogen, $C_1$-$C_8$ alkyl, $C_1$-$C_8$ alkoxy, $C_1$-$C_8$ alkoxyalkyl, $C_3$-$C_8$ cycloalkyl, $C_4$-$C_8$ cycloalkenyl, $(CH_2)_p$ aryl and $(CH_2)_p$-linked 4-, 5-, 6-, 7-, 8-, 9- and 10-membered heterocyclyl; wherein the $C_1$-$C_8$ alkyl, $C_3$-$C_8$ cycloalkyl, $C_4$-$C_8$ cycloalkenyl, and 4-, 5-, 6-, 7-, 8-, 9- and 10-membered heterocyclyl of $R_3$ and $R_4$ are each optionally substituted with one to four substituents independently chosen from halo, hydroxyl, oxo, amino, nitro, cyano, $OCF_3$, $CF_3$, $C_1$-$C_6$ alkyl, $C_1$-$C_4$ alkoxy, $C_1$-$C_4$ hydroxyalkyl, $NR_5R_6$, $CONR_5R_6$, $COOR_5$, $SOR_5$, $SO_2R_5$, $SO_2NR_5R_6$, $NR_5COR_6$ and $NR_5SO_2R_6$. Alternatively, the substituents $R_3$ and $R_4$ taken together with the nitrogen atom to which they are bonded form a heterocyclyl selected from the group consisting of 4-, 5-, 6-, 7-, 8-, 9- and 10-membered heterocyclyl optionally substituted with one to four substituents independently chosen from halo, hydroxyl, oxo, $NR_5R_6$, nitro, cyano, $OCF_3$, $CF_3$, $C_1$-$C_6$ alkyl, $C_1$-$C_4$ alkoxy, $C_1$-$C_4$ hydroxyalkyl, $CONR_5R_6$, $SOR_5$, $SO_2R_5$, $SO_2NR_5R_6$, $COOR_5$, $NR_5COR_6$ and $NR_5SO_2R_6$.

In formula I, substituents $R_5$ and $R_6$ are each independently chosen from hydrogen, $C_1$-$C_4$ alkyl, aryl and 4-, 5-, 6-, 7-, 8-, 9- and 10-membered heterocyclyl, optionally substituted with one to three substituents selected from the group consisting of $C_1$-$C_4$ alkyl, $C_1$-$C_4$ alkoxy, halo, OH, oxo, $NO_2$, $NH_2$, CN, $OCF_3$ and $CF_3$.

In formula I, each instance of p is independently zero or an integer from 1 to 6. Thus, the alkyl linker, $(CH_2)_p$ when present, can be any linear alkyl chain having one to six saturated carbon atoms.

The present invention also provides pharmaceutically acceptable salts, acid salts, stereoisomers, mixtures of stereoisomers, solvates and hydrates of the compounds having the structure of formula I. The invention further provides pharmaceutical compositions comprising a compound having the structure of formula I, or a pharmaceutically acceptable salt, acid salt, stereoisomer, mixture of stereoisomers, solvate or hydrate thereof and a pharmaceutically acceptable diluent, excipient or carrier.

The present invention further provides a method of prophylaxis or treatment of a cannabinoid receptor-associated disease or condition in a mammalian subject, the method comprising administering to the subject an effective amount of a compound having the structure of formula I.

DETAILED DESCRIPTION

Figure 1:
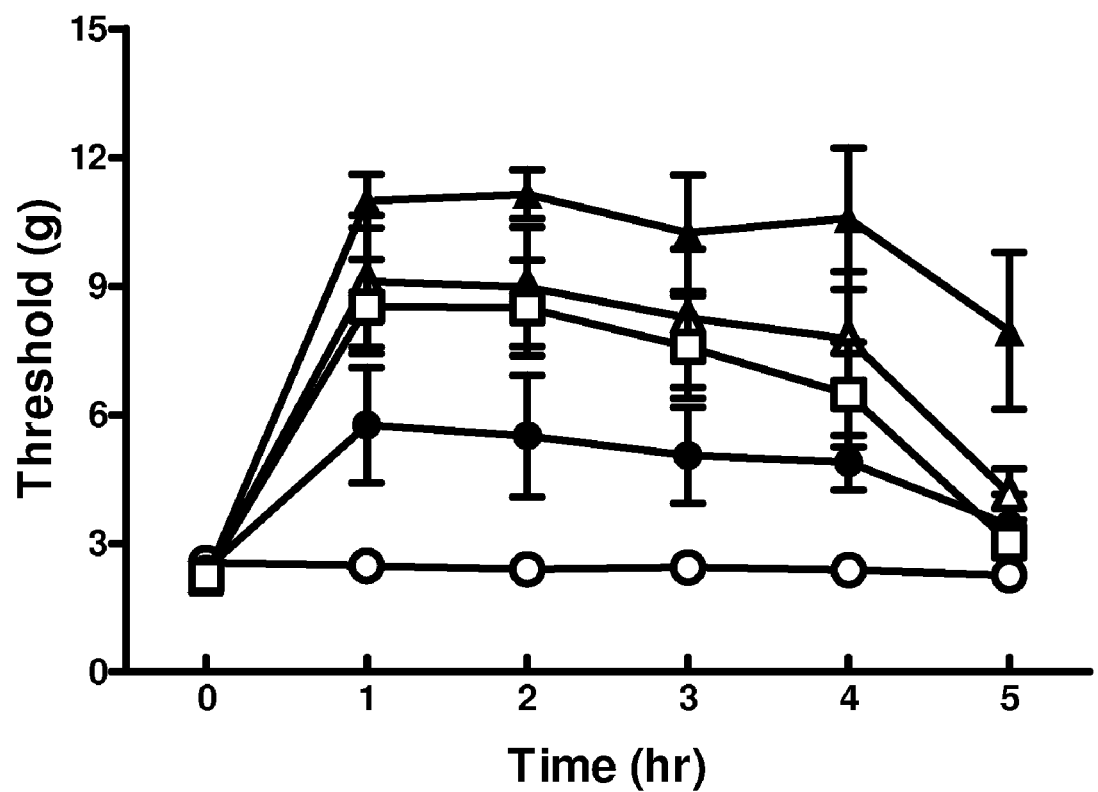
FIG. 1 shows the data obtained in the rat L5/L6 SNL model (n=6/group; mean±sem). Sensitivity to non-noxious mechanical stimuli was tested before and at various time points following oral administration. Open circles denote data obtained with vehicle alone; solid circles: Compound (36) at 3 mg/kg; open triangles 10 mg/kg; solid triangles: 30 mg/kg; open squares: gabapentin at 200 mg/kg. Data for compound (36) at 10 mg/kg and 30 mg/kg were significant to $p<0.001$ vs. vehicle-controls. Data obtained for compound (36) at 3 mg/kg were significant to $p<0.05$ vs. vehicle-controls (two-way repeated measurement ANOVA, Bonferroni post-tests).

The following definitions elucidate the meaning of the listed terms a used in this specification: Alkyl—a saturated branched or straight chain monovalent hydrocarbon radical of a specified number of carbon atoms. Thus, the term alkyl includes, but is not limited to, methyl, ethyl, propyl, isopropyl, n-butyl, t-butyl. A chain of one to six carbon atoms is also herein interchangeably designated as $C_1$-$C_6$ alkyl; a chain of three to six carbon atoms can be alternatively designated as $C_3$-$C_6$ alkyl and so on.

Alkenyl—refers to branched or straight chain hydrocarbon radical having at least one double bond between two carbon atoms. It should be noted that in an alkenyl substituted nitrogen, the unsaturated carbon atom cannot be bound directly to the nitrogen atom, i.e. there must be at least one unsaturated carbon (—$CH_2$—, —CHR'— or —CR'R"—) intervening between the nitrogen atom and the nearest unsaturated carbon atom.

Alkynyl—refers to branched or straight chain hydrocarbon radical having at least one triple bond between two carbon atoms. It should be noted that in an alkynyl substituted nitrogen, the unsaturated carbon atom cannot be bound directly to the nitrogen atom, i.e. there must be at least one unsaturated carbon (—$CH_2$— or —CR'R"—) intervening between the nitrogen atom and the nearest unsaturated carbon atom.

Haloalkyl—an alkyl group having one or more hydrogen atoms substituted with a halogen atom, each independently chosen such that a haloalkyl group having more than one halogen atom can be a mixed haloalkyl, such as for instance, 2-fluoro, 2-chloroethyl, or perhalo as in trifluoromethyl.

Alkoxy—refers to an —O-alkyl substituent.

Cycloalkyl—a saturated monocyclic, polycyclic or bridged hydrocarbon ring system radical or linking group. In a substituted cycloalkyl ring, the substituent is bonded to ring carbon atom replacing a hydrogen atom. The term $C_3$-$C_{10}$ cycloalkyl is herein used to designate a ring of three to ten carbon atoms, or a ring of three of more carbon atoms with the remaining carbon atoms forming one or more alkyl substituents of the ring. Similarly, a $C_3$-$C_7$ cycloalkyl designates a saturated or partially unsaturated carbocycle, although not all the designated number of carbon atoms are necessarily ring carbon atoms. Cycloalkyl typically includes, but is not limited to, cyclopropyl, cyclobutyl, cyclopentyl, cyclohexyl, cyclohexenyl, cycloheptyl and cyclooctyl. However, $C_{10}$ cycloalkyl includes 1,3,3-trimethylbicyclo[2.2.1]heptyl, wherein seven of the ten designated carbon atoms form the seven-membered bicyclo-carbocycle and the remaining three are methyl substituents.

Cycloalkenyl—partially unsaturated monocyclic, polycyclic or bridged hydrocarbon ring system radical or linking group having at least one double bond between two carbon atoms. In a substituted cycloalkenyl ring, the substituent is bonded to ring carbon atom replacing a hydrogen atom. The term $C_3$-$C_{10}$ cycloalkenyl is herein used to designate a ring of three to ten carbon atoms, or a ring of three or more carbon atoms with the remaining carbon atoms forming one or more alkyl substituents of the ring. Similarly, $C_3$-$C_7$ cycloalkenyl designates as partially unsaturated carbocycle, although not all the designated number of carbon atoms are necessarily ring carbon atoms. Cycloalkenyl typically includes, but is not limited to, cyclopentenyl, cyclohexenyl, cycloheptenyl.

Heterocyclyl—a saturated, partially unsaturated or unsaturated monocyclic, polycyclic or bridged hydrocarbon ring system radical or linking group, wherein at least one ring carbon atom has been replaced with a heteroatom selected from nitrogen, oxygen and sulfur. A heterocyclyl ring system further includes a ring system having one, two, three or four nitrogen ring atoms, or a ring system having zero, one, two or three nitrogen ring atoms and one oxygen or sulfur ring atom. The heterocyclic ring system can include more than one ring heteroatom, wherein one heteroatom is nitrogen and the other is selected from nitrogen, oxygen and sulfur. A heterocyclyl radical is derived by the removal of one hydrogen atom from a single carbon or nitrogen ring atom. Heterocyclyl includes, but is not limited to, furyl, thienyl, pyrrole, pyrrolinyl, pyrrolidinyl, pyrrolyl, dioxolanyl, oxazolyl, thiazolyl, imidazolyl, imidazolinyl, imidazolidinyl, pyrazolinyl, pyrazolidinyl, pyrazolyl, isoxazolyl, isothiazolyl, oxadiazolyl, triazolyl, thiadiazolyl, tetrazolyl, pyranyl, pyridinyl, piperidinyl, dioxanyl, morpholinyl, dithianyl, thiomorpholinyl, pyridazinyl, pyrimidinyl, pyrazinyl, piperazinyl, azepanyl, diazepinyl, indolizinyl, indolyl, isoindolyl, indolinyl, benzo[b]furyl, benzo[b]thienyl, indazolyl, benzimidazolyl, benzothiazolyl, purinyl, 4H-quinolizinyl, quinolinyl, isoquinolinyl, cinnolinyl, phthalzinyl, quinazolinyl, quinoxalinyl, napthyridinyl, pteridinyl, quinuclidinyl.

Heterocyclyl—as used herein, also includes an aromatic heterocycle such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, and can be optionally substituted by alkyl. As used herein "heterocyclyl" also includes bicyclic heterocyclyl radicals in which one or both rings are heterocyclic, such as for example, but not limited to imidazopyrazinyl, benzofuranyl, benzodioxolyl, benzothiophenyl, and quinolinyl.

Aryl—an unsaturated, π-electron conjugated monocyclic or polycyclic hydrocarbon ring system radical or linking group of six, ten or fourteen carbon atoms. An aryl radical is derived by the removal of one hydrogen atom from a single carbon ring atom. Aryl includes, but is not limited to, phenyl, naphthalenyl, azulenyl, anthracenyl.

Aminosulfonylalkyl—a radical of the formula —NHSO$_2$-alkyl. Sulfonylamino-alkyl—a linking group of the formula —SO$_2$NH-alkyl—or a radical of the formula —SO$_2$N(alkyl)$_2$.

Halogen—fluoro, chloro, bromo or iodo. Carboxyl—a radical of the formula —COOH. Hydroxyl—a radical of the formula —OH. Cyano—a radical of the formula —C≡N. Oxo—a radical of the formula =O in which the oxygen atom is double-bonded. Amino—a radical of the formula —NH$_2$ or a linking group of the formula —NH—. Aminoalkyl—a radical of the formula —NH-alkyl or —N(alkyl)$_2$.

As used herein, the terms: compound, salt, polymorph, isomer, solvate are also interchangeably referred to in the plural form (i.e. compounds, salts, polymorphs, isomers and solvates). The compounds of the present invention can contain one or more stereogenic centers, depending upon the location and nature of the various substituents desired. These stereogenic centers may be present in the (R) or (S) configuration, and can be in racemic mixtures and/or diastereomeric mixtures. Substituents on a partially or fully saturated ring may also be present in either cis or trans form. All such configurations (including enantiomers and diastereomers) of the compounds described or exemplified herein, are contemplated within the scope of the present invention. Compounds of the invention can also exist as individual stereoisomers or as mixtures in varying ratios (e.g. enantiomerically enriched or racemates). Enantiomeric mixtures of the compounds may be partially or fully resolved through standard purification and/or separation techniques known in the art, including but not limited to chiral chromatography (e.g. chiral derivatized solid phase), formation and separation of diastereomeric salts (e.g. tartaric acid salts or camphorsulfonic acid salts), or enzymatic separation. Diastereomeric mixtures can be separated by techniques well known in the art, based on their physical and/or chemical differences, or by methods described above.

In this specification, salts of a compound of formula I refers to a complex of the compound with an inorganic or organic counter ion or counter ions. For examples, see Handbook of Pharmaceutical Salts: Properties, Selection and Use; Stahl P. H., Wermuth, C. G., Eds.; John Wiley and Sons, 2002. Pharmaceutically useful salts include those obtained by treating the compound, functioning as a base, with an inorganic or organic acid to form a salt or salts. Additional pharmaceutically useful salts include those obtained by treating the compound, functioning as an acid, with an inorganic or organic base to form a salt or salts. Useful salts of the compounds according to the present invention include hydrochloride, hydrobromide, sulfonate, citrate, tartrate, phosphonate, lactate, pyruvate, acetate, succinate, oxalate, fumarate, malate, mesylate, oxaloacetate, methanesulfonate, ethanesulfonate, p-toluenesulfonate, benzenesulfonate and isethionate salts of compounds disclosed herein. Other pharmaceutically useful salts include those obtained by treatment of basic nitrogen-containing groups with such agents as alkyl halides such as chlorides or bromides to form a quaternary ammonium a salt or salts.

As used herein, the term "solvates" describes a complex wherein the compound is coordinated with a proportional amount of a solvent molecule. Specific solvates, wherein the solvent is water, is referred to as hydrates. Combinations of a drug and propylene glycol (1,2-propanediol) have been used to form pharmaceutical drug solvates. See for example U.S. Pat. No. 3,970,651. Other suitable solvates are hydrates of drug compounds. Such hydrates include hydrates which either have comparable activity or hydrates which are converted back to the active compound following administration.

The present invention also contemplates pharmaceutical formulations which comprise one or more of certain compounds disclosed herein, or one or more pharmaceutically acceptable salts, acid salts, stereoisomers, hydrates or solvates thereof, together with one or more pharmaceutically acceptable carriers thereof and optionally one or more other therapeutic ingredients.

The compounds of the present invention described and exemplified herein modulate a signal that regulates a biological activity, by modulating the activity of a cannabinoid receptor. Modulation of a cannabinoid receptor can be effected by a compound of the present invention acting as an agonist, a partial agonist, inverse agonist or an antagonist upon binding at a cannabinoid receptor such as the CB1 receptor or the CB2 receptor, or both the CB1 and CB2 receptors. The modulation of a cannabinoid receptor can be activation by compound of the present invention acting an agonist. Alternatively, the modulation of a cannabinoid receptor can be inhibition or deactivation by an antagonist. Signals regulated by CB1 and also by CB2 are the intracellular concentrations of cyclic adenosine monophosphate (cAMP) and calcium ion ($Ca^{2+}$).

The term 'agonist' as used herein means a molecule that produces a physiological response by activating a receptor. The term 'inverse agonist' as used herein means a molecule that tends to reverse the effect of an agonist. Current theory holds that this occurs due to the higher affinity of the inverse agonist for binding the inactive conformation over the active conformation of the receptor. The term 'antagonist' as used herein means a molecule that binds a receptor and thereby interferes with the interaction of an agonist and its cognate receptor, or blocks the constitutive activity of the receptor. The term 'neutral antagonist' as used herein means a molecule that binds a receptor with equal affinity for the active and inactive conformations and thereby inhibits receptor activity by competing with an agonist.

The present invention provides many embodiments of the compounds having the structure of formula I, several of which are specifically enumerated below:

In a first embodiment, the compounds of the present invention have the structure of formula I:

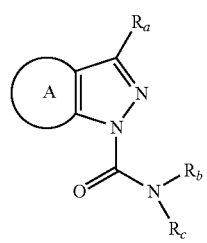

(I)

wherein the ring moiety A is a five, six or seven-membered ring structure having one of the following structures:

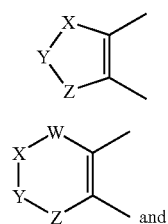

(i)

(ii)

and

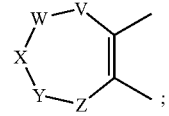

(iii)

;

in which the moieties V, W, X, Y and Z are each independently chosen from oxygen, $NR_1$ and $CR_1R_2$; provided that only one moiety of V, W, X, Y and Z in any ring moiety A can be oxygen or $NR_1$.

In another embodiment, only one of V, W, X, Y and Z is O and all others are each independently $CR_1R_2$. Alternatively, V, W, X, Y and Z are each $CR_1R_2$.

In another embodiment, the present invention provides compound of formula I wherein the radical $R_a$ is chosen from $C_1$-$C_8$ alkyl, $C_3$-$C_8$ cyclo-alkyl, $C_4$-$C_8$ cycloalkenyl, aryl, 4-, 5-, 6-, 7-, 8-, 9- and 10-membered heterocyclyl; wherein the $C_1$-$C_8$ alkyl, $C_3$-$C_8$ cycloalkyl, $C_4$-$C_8$ cycloalkenyl, aryl, heterocyclyl of $R_a$ are each optionally substituted with one to four substituents independently chosen from halo, hydroxyl, oxo, amino, nitro, cyano, COOH, $OCF_3$, $CF_3$, $C_1$-$C_6$ alkyl, $C_1$-$C_4$ alkoxy, $C_4$-$C_8$ alkenyl, $C_3$-$C_6$ cyclo-alkyl, aryl and 4-, 5-, 6-, 7-, 8-, 9- and 10-membered heterocyclyl.

In another embodiment of the compounds of formula I, the radical $R_b$ is chosen from hydrogen and $C_1$-$C_6$ alkyl optionally substituted with one to four substituents independently chosen from $C_1$-$C_4$ alkoxy, halo, hydroxyl, amino and cyano.

In still another embodiment, the radical $R_c$ is chosen from $CR_dR_eR_f$, $C_3$-$C_{10}$ cycloalkyl, aryl and 4-, 5-, 6- 7- 8-, 9, or 10-membered heterocyclyl; wherein the $C_3$-$C_{10}$ cycloalkyl, aryl, heterocyclyl of $R_c$ is optionally substituted with one to four substituents independently chosen from halo, hydroxyl, oxo, amino, nitro, cyano, $COOR_1$, $OCF_3$, $CF_3$, $C_1$-$C_4$ alkyl, $C_1$-$C_4$ alkoxy and $C_3$-$C_6$ cyclo-alkyl, $CONR_1R_2$, $SOR_1$, $SO_2R_1$, $SO_2NR_1R_2$, $NR_1SO_2R_2$ and $NR_1COR_2$.

In yet another embodiment, the radical $R_d$ is chosen from hydrogen, $C_1$-$C_6$ alkyl, $C_3$-$C_8$ cycloalkyl, $(CH_2)_p$aryl, 4-, 5-, 6-, 7-, 8-, 9- and 10-membered $(CH_2)_p$heterocyclyl; wherein the $C_1$-$C_6$ alkyl, $C_3$-$C_8$ cycloalkyl, $(CH_2)_p$aryl, $(CH_2)_p$ heterocyclyl of $R_d$ are each optionally substituted with one to four substituents independently chosen from $C_1$-$C_4$ alkyl, $C_1$-$C_4$ alkoxy, $C_1$-$C_4$ hydroxyalkyl, $C_1$-$C_4$ haloalkyl, $C_1$-$C_4$ haloalkoxy, aryl, halo, hydroxyl, $NR_1R_2$, cyano, nitro and $CONR_1R_2$. Alternatively, radicals $R_b$ and $R_d$ taken together with the nitrogen atom and carbon atom to which they are respectively bonded form a 4-, 5-, 6- 7- 8-, 9, or 10-membered heterocyclyl, which heterocyclyl is optionally substituted with one to three substituents independently chosen from halo, hydroxyl, oxo, $C_1$-$C_4$ alkyl, $C_1$-$C_4$ alkoxy, $C_1$-$C_4$ hydroxyalkyl, $COOR_1$, $CONR_1R_2$, $SOR_1$, $SO_2R_1$, $SO_2NR_1R_2$, $NR_1SO_2R_2$ and $NR_1COR_2$.

In another embodiment, the radical $R_e$ is chosen from hydrogen, $C_1$-$C_8$ alkyl, $C_3$-$C_6$ alkenyl, $C_3$-$C_6$ alkynyl, aryl, $C_3$-$C_8$ cycloalkyl, $C_4$-$C_8$ cycloalkenyl, $C_1$-$C_6$ hydroxyalkyl, $COR_3$, $CONR_3R_4$, $CSNR_3R_4$, $COOR_3$, $SOR_3$, $SO_2R_3$, $SO_2NR_3R_4$, $NR_3SO_2R_4$ and $NR_3COR_4$ and $(CH_2)_p$heterocyclyl; wherein the $C_1$-$C_8$ alkyl, $C_3$-$C_6$ alkenyl, $C_3$-$C_6$ alkynyl, aryl, $C_3$-$C_8$ cycloalkyl, $C_4$-$C_8$ cycloalkenyl, and $(CH_2)_p$heterocyclyl of $R_e$ are each optionally substituted with one to four substituents independently chosen from halo, hydroxyl, oxo, amino, nitro, cyano, $OCF_3$, $CF_3$, $C_1$-$C_4$ alkyl, $C_1$-$C_4$ alkoxy, $C_3$-$C_6$ cycloalkyl, aryl, $CONR_1R_2$, $SOR_1$, $SO_2R_1$, $SO_2NR_1R_2$, $COOR_1$, $NR_1COR_2$ and $NR_1SO_2R_2$.

In a further embodiment, the radical $R_f$ is chosen from hydrogen, $C_1$-$C_6$ alkyl and $C_1$-$C_8$ hydroxyalkyl. Alternatively, the radicals $R_d$ and $R_f$ taken together with the carbon atom to which they are bonded form a $C_3$-$C_8$ cycloalkyl, or 4-, 5-, 6- 7- 8-, 9, or 10-membered heterocyclyl, which $C_3$-$C_8$ cycloalkyl or heterocyclyl formed is optionally substituted with one to three substituents independently chosen from $C_1$-$C_4$ alkyl, $C_1$-$C_4$ alkoxy, $C_1$-$C_4$ hydroxyalkyl, $CONR_1R_2$, halo, hydroxyl and oxo.

In another embodiment, each instance of substituent $R_1$ and substituent $R_2$ is independently chosen from hydrogen, $C_1$-$C_6$ alkyl, $C_2$-$C_6$ alkenyl, $C_3$-$C_8$ alkynyl and $C_3$-$C_8$ cycloalkyl; wherein the $C_1$-$C_6$ alkyl, $C_2$-$C_6$ alkenyl, $C_3$-$C_8$ alkynyl and $C_3$-$C_8$ cyclo-alkyl of each $R_1$ and each $R_2$ is optionally substituted with one to four substituents independently chosen from $C_1$-$C_4$ alkyl, $C_1$-$C_4$ alkoxy, halo, hydroxyl, oxo, nitro, CN, $OCF_3$, $CF_3$, $NR_3R_4$, $CONR_3R_4$, $COOR_3$, $SOR_3$, $SO_2R_3$, $SO_2NR_3R_4$, $NR_3COR_4$ and $NR_3SO_2R_4$.

Alternatively, in another embodiment, the radicals $R_1$ and $R_2$ taken together with the carbon or nitrogen atom(s) to which they are both bonded form a $C_3$-$C_8$ cycloalkyl, $C_4$-$C_8$ cycloalkenyl or 3- to 8-membered heterocyclyl; wherein the $C_3$-$C_8$ cycloalkyl, $C_4$-$C_8$ cycloalkenyl or heterocyclyl is optionally substituted with one to three substituents independently chosen from $C_1$-$C_4$ alkyl, $C_1$-$C_4$ alkoxy, halo, hydroxyl, oxo, amino, nitro, cyano, $OCF_3$, and $CF_3$.

In still another embodiment, the substituents $R_3$ and $R_4$ are each independently chosen hydrogen, $C_1$-$C_8$ alkyl, $C_1$-$C_8$ alkoxy, $C_1$-$C_8$ alkoxyalkyl, $C_3$-$C_8$ cycloalkyl, $C_4$-$C_8$ cycloalkenyl, aryl, 4-, 5-, 6-, 7-, 8-, 9- and 10-membered heterocyclyl; wherein the $C_1$-$C_8$ alkyl, $C_3$-$C_8$ cycloalkyl, $C_4$-$C_8$ cycloalkenyl, aryl and heterocyclyl of $R_3$ and $R_4$ are each optionally substituted with one to four substituents independently chosen from halo, hydroxyl, $OCF_3$, $CF_3$, cyano, nitro, oxo $C_1$-$C_4$ alkyl, $C_1$-$C_4$ alkoxy, $C_1$-$C_4$ hydroxyalkyl, $NR_5R_6$, $COOR_5$, $SOR_5$, $SO_2R_5$, $SO_2NR_5R_6$, $CONR_5R_6$, $NR_5COR_6$ and $NR_5SO_2R_6$.

Alternatively, the radicals $R_3$ and $R_4$ taken together with the nitrogen atom to which they are bonded form a 4-, 5-, 6-, 7-, 8-, 9- or 10-membered heterocyclyl optionally substituted with one to four substituents independently chosen from halo, hydroxyl, $OCF_3$, $CF_3$, cyano, nitro, oxo $C_1$-$C_4$ alkyl, $C_1$-$C_4$ alkoxy, $C_1$-$C_4$ hydroxyalkyl, $NR_5R_6$, $COOR_5$, $SOR_5$, $SO_2R_5$, $SO_2NR_5R_6$, $CONR_5R_6$, $NR_5COR_6$ and $NR_5SO_2R_6$.

In another embodiment, the substituents $R_5$ and $R_6$ is independently chosen from hydrogen, $C_1$-$C_4$ alkyl, aryl and 4-, 5-, 6-, 7-, 8-, 9- and 10-membered heterocyclyl, optionally substituted with one to three substituents chosen from $C_1$-$C_4$ alkyl, $C_1$-$C_4$ alkoxy, halo, OH, oxo, $NO_2$, $NH_2$, CN, $OCF_3$ and $CF_3$ In another embodiment, each instance of the operator, p in the linker —$(CH_2)_p$— in formula I is independently 0 or an integer from 1 to 6; or alternatively, p is 0 or 1, 2 or 3.

In another embodiment, the invention provides a compound having the structure of formula I, wherein the moieties V, W, X, Y and Z are each independently chosen from oxygen, $NR_1$ and $CR_1R_2$; the radical $R_a$ is chosen from $C_1$-$C_8$ alkyl, $C_3$-$C_8$ cycloalkyl, aryl, 4-, 5-, 6-, 7-, 8-, 9- and 10-membered heterocyclyl; wherein the alkyl, aryl and heterocyclyl of $R_a$ are each optionally substituted with one to four substituents independently chosen from halo, OH, oxo, $NH_2$, $NO_2$, CN, COOH, $OCF_3$, $CF_3$, $C_1$-$C_6$ alkyl, and $C_1$-$C_4$ alkoxy.

In another embodiment, the radical $R_b$ is chosen from hydrogen and $C_1$-$C_6$ alkyl optionally substituted with one to three substituents independently chosen from $C_1$-$C_4$ alkoxy, halo, hydroxyl, amino and cyano.

In still another embodiment, the radical $R_c$ is defined by $CR_dR_eR_f$ wherein the radical $R_d$ is chosen $C_1$-$C_6$ alkyl, $C_3$-$C_8$ cycloalkyl, aryl, 4-, 5-, 6-, 7-, 8-, 9- and 10-membered heterocyclyl; wherein the alkyl, cycloalkyl, aryl, and heterocyclyl of $R_d$ are each optionally substituted with one to three substituents independently chosen from $C_1$-$C_4$ alkyl, $C_1$-$C_4$ alkoxy, $C_1$-$C_4$ hydroxyalkyl, aryl, halo, hydroxyl, amino, cyano and nitro; the radical $R_e$ is chosen from $C_1$-$C_8$ alkyl, $C_3$-$C_6$ alkenyl, aryl, $C_3$-$C_8$ cycloalkyl, $C_4$-$C_8$ cycloalkenyl, $C_1$-$C_6$ hydroxyalkyl, $COR_3$, $CONR_3R_4$, $COOR_3$ and $(CH_2)_p$ heterocyclyl; wherein the $C_1$-$C_8$ alkyl, $C_3$-$C_6$ alkenyl, $C_3$-$C_6$ alkynyl, aryl, $C_3$-$C_s$ cycloalkyl, $C_4$-$C_8$ cycloalkenyl, and $(CH_2)_p$ heterocyclyl of $R_e$ are optionally substituted with one to three substituents independently chosen from halo, hydroxyl, oxo, amino, nitro, cyano, COOH, $OCF_3$, $CF_3$, $C_1$-$C_4$ alkyl, $C_1$-$C_4$ alkoxy; and the radical $R_f$ is hydrogen or $C_1$-$C_6$ alkyl.

In another embodiment of the compounds of formula I, each instance of the operator p in the linker —$(CH_2)_p$— is independently zero, one, two or three.

In another embodiment of the compounds of formula I, $R_e$ is chosen from $COR_3$, $CONR_3R_4$ and $COOR_3$.

In another embodiment of the compounds of formula I, one of the moieties V, W, X, Y and Z is $NR_1$ or oxygen; and the radical $R_1$ is chosen from hydrogen, $C_1$-$C_6$ alkyl, $C_1$-$C_6$ haloalkyl and $C_1$-$C_6$ hydroxyalkyl.

In another embodiment, the moieties V, W, X, Y and Z are each independently $CR_1R_2$; wherein the radicals $R_1$ and $R_2$ are each independently chosen from hydrogen, $C_1$-$C_6$ alkyl, $C_1$-$C_6$ haloalkyl and $C_1$-$C_6$ hydroxyalkyl.

In another embodiment, the radical $R_a$ is chosen from $C_3$-$C_8$ cycloalkyl, $C_4$-$C_8$ cycloalkenyl, $(CH_2)_p$aryl, $(CH_2)_p$-linked 4-, 5-, 6-, 7-, 8-, 9- and 10-membered heterocyclyl; wherein the cycloalkyl, cycloalkenyl, aryl and heterocyclyl of $R_a$ are each optionally substituted with one to four substituents independently chosen from halo, hydroxyl, oxo, amino, nitro, cyano, COOH, $OCF_3$, $CF_3$, $C_1$-$C_6$ alkyl, and $C_1$-$C_4$ alkoxy. In one aspect of this embodiment p of $(CH_2)_p$aryl and $(CH_2)_p$-linked heterocyclyl is 0.

In still another embodiment, the radical $R_a$ is aryl, optionally substituted with one to four substituents independently chosen from halo, hydroxyl, oxo, amino, nitro, cyano, COOH, $OCF_3$, $CF_3$, $C_1$-$C_6$ alkyl, and $C_1$-$C_4$ alkoxy.

In a further embodiment, the radical $R_b$ is hydrogen or $C_1$-$C_4$ alkyl. In another further embodiment, the radical $R_b$ is hydrogen or methyl.

In another embodiment, the radical $R_d$ is chosen from hydrogen, $C_1$-$C_6$ alkyl, $C_3$-$C_8$ cycloalkyl, aryl, 4-, 5-, 6-, 7-, 8-, 9- and 10-membered heterocyclyl; wherein the alkyl, cycloalkyl, aryl and heterocyclyl of $R_d$ are optionally substituted with one to four substituents independently chosen from $C_1$-$C_4$alkyl, $C_1$-$C_4$ alkoxy, $C_1$-$C_4$ hydroxyalkyl, aryl, halo, hydroxyl, amino, nitro and cyano.

In another further embodiment, the radical $R_e$ is chosen from $C_1$-$C_8$ alkyl, aryl, $C_3$-$C_8$ cycloalkyl, $C_1$-$C_6$ hydroxyalkyl, $COOR_3$, $CONR_3R_4$, $COR_3$, $SO_2NR_3R_4$, 4-, 5-, 6- 7- 8-, 9, and 10-membered heterocyclyl; wherein the alkyl, cycloalkyl, aryl and heterocyclyl of $R_e$ are optionally substituted with one to four substituents independently chosen from halo, hydroxyl, oxo, amino, nitro, cyano, COOH, $OCF_3$, $CF_3$, $C_1$-$C_4$ alkyl, $C_1$-$C_4$ alkoxy, $C_3$-$C_6$ cycloalkyl, and phenyl; and the radical $R_f$ is hydrogen or $C_1$-$C_4$ alkyl.

In another embodiment of the compounds of formula I, the radical $R_d$ is chosen from hydrogen and $C_1$-$C_6$ alkyl optionally substituted with one to four substituents independently chosen from $C_1$-$C_4$ alkoxy, $C_1$-$C_4$ hydroxyalkyl, halo, hydroxyl, amino, cyano and nitro; and the radical $R_f$ is hydrogen or methyl.

In another embodiment, the radical $R_d$ is chosen from hydrogen and $C_1$-$C_6$ alkyl.

In still another embodiment, the radical $R_e$ is chosen from $CONR_3R_4$, $COOR_3$, 4-, 5-, 6- 7- 8-, 9 and 10-membered heterocyclyl; wherein the heterocyclyl is optionally substituted with one to four substituents independently chosen from halo, hydroxyl, oxo, amino, nitro, cyano, COOH, $OCF_3$, $CF_3$ and $C_1$-$C_4$ alkyl.

In another further embodiment, the radical $R_e$ is a 4-, 5-, 6- 7- 8-, 9, or 10-membered heterocyclyl optionally substituted with one to four substituents independently chosen from halo, hydroxyl, oxo, amino, cyano, nitro, COOH, $OCF_3$, $CF_3$ and $C_1$-$C_4$ alkyl. In an alternative embodiment, the radical $R_e$ is $CONR_3R_4$.

In another embodiment, the radicals $R_3$ and $R_4$ are each independently chosen from hydrogen, $C_1$-$C_8$ alkyl, $C_3$-$C_8$ cycloalkyl, $C_1$-$C_8$ alkoxy, $C_1$-$C_8$ alkoxyalkyl, 4-, 5- and 6-membered heterocyclyl; wherein the alkyl, cycloalkyl and heterocyclyl of $R_3$ and $R_4$ are each independently optionally substituted with one to three substituents independently chosen from halo, hydroxyl, oxo, amino, cyano, nitro, COOH, $CONR_1R_2$, $OCF_3$, $CF_3$ and $C_1$-$C_6$ alkyl.

The present invention also provides pharmaceutical compositions that include one or more compounds having the structure of formula I and a pharmaceutically acceptable diluent, excipient or carrier. Suitable diluents, excipients and carriers for use in combination with the compounds of the present invention are described in U.S. Pat. No. 7,517,874.

The invention also provides a method of prophylaxis or treatment of a cannabinoid receptor-associated disease or condition in a mammalian subject, wherein the method includes administering to the subject an effective amount of a compound having the structure of formula I. The cannabinoid receptor-associated disease or condition treated or prevented by this method can be pain, inflammation or pruritis. The particular form of pain can be visceral pain, somatic pain, cutaneous pain, neuropathic pain and inflammatory pain.

In another embodiment, the compounds have the structure of formula I that exhibit limited penetration across the blood-brain barrier (BBB), and are characterized in that they comprise ionizable and/or polar groups, such as for instance, carboxylate or halo groups respectively, or bulky groups such as, without limitation, branched alkyl groups or cycloalkyl groups, each of which tend to impede transport across the BBB.

The above-described compounds can be formulated in pharmaceutically acceptable salts, acids salts, solvates (including hydrates) and stereoisomers of the compounds having the structure of formula I. Also provided by the present invention are mixtures of stereoisomers of the compounds having the structure of formula I wherein the mixture can include equal quantities of each stereoisomer, or the mixture can contain an excess of one stereoisomer over another.

In one embodiment of the invention, the compounds having the structure of formula I bind one or more cannabinoid receptors such as, without limitation the CB1 receptor or the CB2 receptor.

As used herein, a cannabinoid receptor-associated disease, condition or disorder is any disease, condition or disorder that is preventable or treatable by modulation of a cannabinoid receptor, such as and without limitation, CB2 or CB1. The modulation can be activation by an agonist, or inhibition by an inverse agonist. The cannabinoid receptor can be any mammalian cannabinoid receptor, such as but not limited to, a human cannabinoid receptor or a rat cannabinoid receptor. In one aspect, the compounds of the invention having the structure of formula I are cannabinoid receptor agonists that activate a cannabinoid receptor.

The cannabinoid receptor-associated disease, condition or disorder can be any cannabinoid receptor-associated disease, condition or disorder, such as and without limitation: pain, inflammation, immunomodulation and pruritis; and can also include osteoclastogenesis. The cannabinoid receptor-associated disease, condition or disorder can also be obesity.

The cannabinoid receptor-associated pain can be neuropathic pain, somatic pain, visceral pain, cutaneous pain, ocular pain, otic pain, diabetic pain, pain associated with inflammatory bowel disease or irritable bowel syndrome, breakthrough cancer pain, metastatic cancer pain, virally-induced pain (such as AIDS-associated pain), chemotherapy-induced pain or migraine.

The cannabinoid receptor-associated inflammation can be otic or ocular inflammation due to any of a variety of causes; inflammation due to rheumatoid arthritis or other autoimmune disorders, eczema, atopic dermatitis, inflammatory bowel disease, irritable bowel syndrome, kidney dialysis, insect bites or the inflammation can be inflammation caused by a surgical procedure, accidental injury, viral or bacterial infection, or a degenerative disease or condition.

The cannabinoid receptor-associated pruritis can be opioid-induced pruritis, where in the pruritis is caused by use or abuse of an opioid, such as morphine.

The cannabinoid receptor can be any mammalian cannabinoid receptor, such as but not limited to, a human cannabinoid receptor or a rat cannabinoid receptor. In one aspect, the compounds of the invention having the structure of formula I are cannabinoid receptor agonists that activate a cannabinoid receptor.

In some embodiments, a particular dose and route of administration of the compound can be chosen by a clinician to completely prevent or cure the disease, condition or disorder. In other embodiments a particular dose and route of administration of the compound chosen by the clinician ameliorates or reduces one or more symptoms of the disease, condition or disorder.

As used herein, "effective amount" or "sufficient amount" of a compound of the invention refers to an amount of the compound as described herein that may be therapeutically effective to inhibit, prevent, or treat a symptom of a particular disease, disorder, condition, or side effect.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

As used herein, a "pharmaceutically acceptable salt" refers to a derivative of a compound wherein the parent compound is modified by making an acid or a base salt thereof. Examples of pharmaceutically acceptable salts include, but are not limited to, mineral or organic acid salts of basic residues such as amines; alkali or organic salts of acidic residues such as carboxylic acids and the like.

The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt of a compound of the invention can be formed from any such compound of formula I having either acidic, basic or both functional groups. For example, a compound of formula I having a carboxylic acid group, may in the presence of a pharmaceutically suitable base, form a carboxylate anion paired with a cation such as a sodium or potassium cation. Similarly, a compound of the invention having an amine functional group may, in the presence of a pharmaceutically suitable acid such as HCl, form a salt.

Pharmaceutically acceptable carriers used in parenteral preparations of the compounds of formula I include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride for injection, Ringers solution for injection, isotonic dextrose for injection, sterile water for injection, dextrose and lactated Ringers solution for injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose.

Buffers include phosphate and citrate. Antioxidants include sodium bisulfite. Local anesthetics include procaine hydrochloride.

Suspending and dispersing agents include sodium carboxymethylcelluose, hydroxypropyl methylcellulose and polyvinylpyrrolidone.

Emulsifying agents include Polysorbate 80 (Tween 80). A sequestering or chelating agent of metal ions such as EDTA can also be incorporated. Pharmaceutical carriers also include ethyl alcohol, polyethylene glycol and propylene glycol for water miscible vehicles and the pH can be adjusted to a physiologically compatible pH by addition of sodium hydroxide, hydrochloric acid, citric acid or lactic acid.

The pharmaceutical compositions that include the compounds of formula I of the invention can be delivered or administered intravenously, transdermally, transmucosally, intranasally, subcutaneously, intramuscularly, orally or topically (such as for example to the eye). The compositions can be administered for prophylaxis or treatment of individuals suffering from, or at risk of a disease or a disorder. Prophylaxis is defined as a measure designed to preserve the health of an individual.

For therapeutic applications, a pharmaceutical composition is typically administered to a subject suffering from a disease, condition or disorder, in an amount sufficient to inhibit, prevent, or ameliorate the disease or disorder. An amount adequate to accomplish this is defined as an effective amount or a therapeutically effective dose.

The pharmaceutical compositions of the invention can be administered to a mammal for prophylactic or therapeutic purposes in any of the above-described formulations and delivery modes. The mammal can be any mammal, such as a domesticated or feral mammal, or even a wild mammal. The mammal can be any mammal, such as for instance a primate, ungulate, canine or feline. For instance, and without limitation, the mammal can be a pet or companion animal, such as a dog or a cat; a high-value mammal such as a thoroughbred or show animal; a farm animal, such as a cow, a goat, a sheep or pig; or a primate such as an ape or monkey. In one embodiment, the mammalian cannabinoid receptor is a human cannabinoid receptor, such as a human CB1 receptor (hCB1) or a human CB2 receptor (hCB2).

Without wishing to be bound by any particular theory, it is believed that due to their ability to bind and modulate the activity of the CB1 receptor, the CB2 receptor, or both the CB1 and CB2 receptors, the compounds of the present invention are useful in the treatment of conditions or disorders that include, but are not limited to, inflammatory diseases such as rheumatoid arthritis, systemic lupus erythematosus, Crohn's disease, psoriasis, eczema, multiple sclerosis, diabetes and thyroiditis.

Certain compounds of the invention can also be used in the treatment of disorders that include, but are not limited to, pain (e.g. inflammatory pain, visceral pain, postoperative pain, cancer pain, neuropathic pain, musculoskeletal pain, dysmenorrhea, menstrual pain, migraine, headache); skin disorders (e.g. sunburn, dermatitis, pruritis); lung disorders (e.g. chronic obstructive pulmonary disease, cough, asthma, bronchitis); ophthalmic disorders (e.g. glaucoma, retinitis, reinopathies, uveitis, conjunctivitis); gastrointestinal disorders (e.g. ulcerative colitis, irritable bowel syndrome, coeliac disease, inflammatory bowel disease, gastroesophageal reflux disease, organ transplant, nausea, emesis); cardiovascular disorders (e.g. stroke, cardiac arrest, atherosclerosis, myocardial ischemia); neurodegenerative, neuroinflammatory or psychiatric disorders (e.g. senile dementia, Alzheimer's disease, vascular dementia, amyotrophic lateral sclerosis, neuroinflammation, tinnitus); bladder disorders (e.g. bladder hyper-reflexia, cystitis) and cancer, such as for instance, lymphoblastic leukemia and lymphoma, acute myelogenous leukemia, chronic lymphocytic leukemia, glioma, skin cancer, breast cancer, prostate cancer, liver cancer, kidney cancer, lung cancer and pancreatic cancer.

In addition, certain compounds of the invention can be used to modulate bone formation and/or resorption for treating conditions including, but not limited to, ankylosing spondylitis, gout, arthritis associated with gout, osteoarthritis and osteoporosis.

Certain compounds of the invention can also be used for the treatment of neuropathic pain including but not limited to diabetic neuropathy, fibromyalgia, lower back pain, sciatica, pain from physical trauma, cancer, amputation, toxins or chronic inflammatory conditions.

The compounds of the invention and their pharmaceutically acceptable salts can be administered in a standard manner, for example parentarally, orally (p.o.), intravenously (i.v.), intramuscularly (i.m.), sublingually, dermally, transdermally, rectally, or via inhalation, or by buccal, nasal, ocular or otic administration.

General Methods

All reactions involving moisture sensitive compounds were carried out under an anhydrous nitrogen or argon atmosphere. All reagents were purchased from commercial sources and used without further purification. Unless otherwise noted, the starting materials used in the examples were obtained from readily available commercial sources or synthesized by standard methods known to those skilled in the art of organic synthesis.

Reactions performed under microwave irradiation conditions were carried out in a Biotage Initiator® 60 microwave system (Charlottesville, Va.; model# 10986-22V) with a 300 watt magnetron. Normal phase chromatography and reverse phase chromatography was performed on an ISCO Combi-Flash® Companion® or CombiFlash® Companion/TS® system (Teledyne Isco, Inc., Lincoln, Nebr.). Preparative LC-MS was performed with a Waters (Waters Corporation, Milford, Mass.) HPLC-MS system equipped with a 2767 Sample Manager, 2545 Binary Gradient Module, SFO System Fluidics Organizer, 2996 Photodiode Array Detector and 3100 Mass Detector. Data was collected across a range of wavelengths from 220 nm to 280 nm and in positive electrospray-chemical ionization mode. The HPLC column used was a Waters XBridge C18 5 um 4.6×150 mm. Spectra were scanned from 100-1400 atomic mass units. The eluents were A: water with 0.1% formic acid and B: acetonitrile with 0.1% formic acid. Gradient elution from 5% B to 95% B over 10 minutes was used with an initial hold of 1.2 minutes and final hold at 95% B of 1.0 minutes at a flow rate of 20 mL/min.

Compounds were characterized by their LCMS-Electrospray/chemical ionization mass spectra (LC ESCI-MS) on one of the following systems:

1) Waters HPLC-MS system (Waters Corp., Milford, Mass.) equipped with a 2767 Sample Manager, 2545 Binary Gradient Module, SFO System Fluidics Organizer, 2996 Photodiode Array Detector and 3100 Mass Detector. Data were collected across a range of wavelengths from 220 nm to 280 nm in positive ESCI mode. Spectra were scanned from 100-1400 atomic mass units (amu). The HPLC column was a Waters XBridge C18 3.5 μm 4.6×30 mm; eluents were A: water with 0.1% formic acid and B: acetonitrile with 0.1% formic acid. Gradient elution was from 5% B to 95% B over 2.3 minutes with an initial hold of 0.2 minutes and a final hold at 95% B of 0.5 minutes. Total run time was 4 minutes.

2) Waters (Waters Corporation, Milford, Mass.) UPLC-MS system equipped with an Acquity Sample Manager, Acquity Binary Solvent Manager, Acquity Photodiode Array Detector, Acquity Evaporative Light Scattering Detector and SQ Detector. Data were collected at 220 nm and 254 nm and in positive electrospray-chemical ionization mode. The UPLC column used was a Waters Acquity UPLC BEH C18 1.7 um 2.1×50 mm. Spectra were scanned from 100-1400 amu. The eluents were A: water with 0.1% formic acid and B: acetonitrile with 0.1% formic acid. Gradient elution from 5% B to 95% B over 0.8 minutes was used with a final hold at 95% B of 0.2 minutes at a flow rate of 0.8 milliliters per minute. Total run time was 1.5 minutes.

Nuclear magnetic resonance spectra were recorded using a Bruker Avance III (400 MHz shielded) spectrometer equipped with a Gradient Multinuclear Broadband Fluorine Observe (BBFO) probe. Spectra were acquired in the indicated solvent. Chemical shifts (β) are given in ppm (parts per million upfield or downfield from TMS defined as 0 ppm). Coupling constants J are in hertz (Hz). Peak shapes in the NMR spectra are indicated by symbols 'q' (quartet), 't' (triplet), 'd' (doublet), 's' (singlet), 'br s' (broad singlet), 'br' (broad) 'm' (multiplet) and 'br d' (broad doublet).

Abbreviations used herein:

AcO (or OAc):—acetate; AcOH:—acetic acid; Boc:—tert-butoxycarbonyl; Cbz:—benzyl-oxycarbonyl; DCM:—dichloromethane; DIEA:—N,N-diisopropylethylamine; DMF:—dimethylformamide; DMSO:—dimethylsulfoxide; ESI:—electron spray ionization; EtOAc:—ethyl acetate; HCl:—hydrochloric acid; ¹H-NMR:—proton nuclear magnetic resonance; LAH:—lithium aluminum hydride; LC-MS:—liquid chromatography-mass spectrometry; LHMDS:—lithium hexamethyldisilazide; MeCN:—acetonitrile; MeOH:—methanol; NaHCO$_3$:—sodium bicarbonate; Na$_2$SO$_4$:—sodium sulfate; TFA:—trifluoroacetic acid; THF:—tetrahydrofuran; TLC:—thin layer chromatography.

Synthetic Schemes

Compounds of the present invention can be prepared according to the non-limiting synthetic methods detailed in the scheme 1 adapted from procedures described in *Organic Letters*, 2006, 8 (13), 2675-2678.

Commercially available cyclic ketones 1 are treated with a strong base such as lithium hexamethyldisilazide (LHMDS) and the resulting anionic species reacts with an acyl chloride R$_a$COCl to give the diketone intermediate 2. Without need for isolation or purification, the diketone intermediate 2 undergoes cyclization reactions with hydrazine to form the bicyclic pyrazole intermediate 3, which is then reacted with phosgene followed by amines to provide the desired compound 4.

Scheme 1

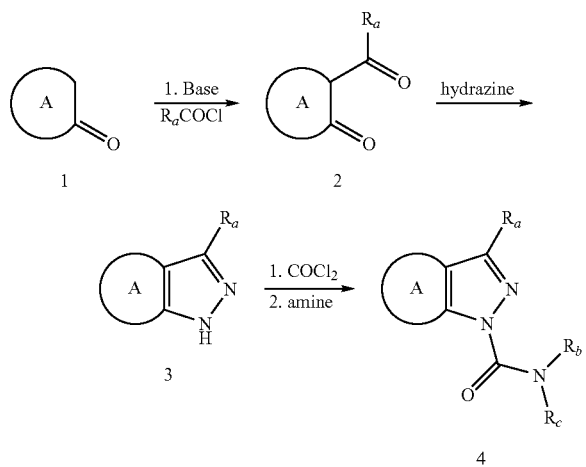

Compounds of the present invention, wherein ring moiety A is a six-membered

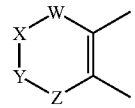

ring having the structure wherein X is NR$_1$ can be prepared according to the method outlined in Scheme 1 starting with 1-Boc-4-piperidone.

Scheme 2

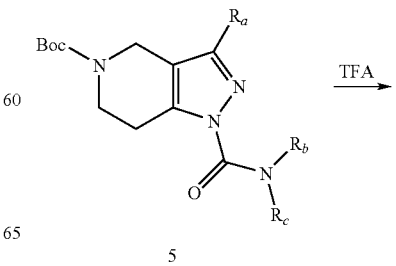

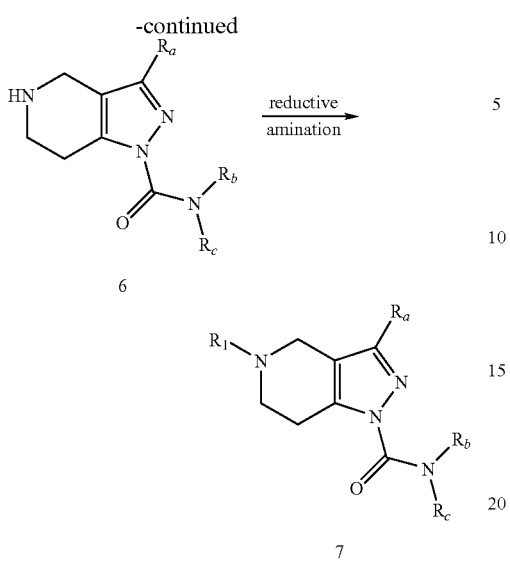

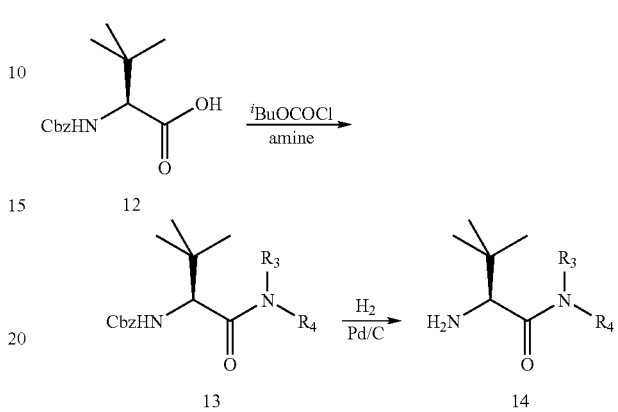

As shown in Scheme 2, the Boc protecting group of intermediate 5 is removed under standard acidic conditions, such as treatment with TFA, and the resulting amino intermediate 6 undergoes reductive amination in the presence of aldehydes or ketones to yield the desired compound 7.

Following the synthetic methods described in Schemes 1 and 2, target compounds 10 and 11 can be prepared from the diketone intermediates 8 and 9 respectively and subsequently separated as the bicyclic pyrazoles.

When 1-Boc-3-piperidone is used as a starting material for the synthetic sequence outlined in Scheme 1, two isomeric diketone intermediates 8 and 9 can be obtained (Scheme 3).

Tert-leucine amide derivatives used in the synthesis of the target compounds of the invention can be prepared from N-protected tert-leucine derivatives such as Cbz-tert-leucine 12 (Scheme 4).

Treatment of Cbz-tert-leucine with isobutyl chloroformate in the presence of an organic base such as DIEA, followed by in situ reaction with amines or ammonia can provide amide intermediate 13. Deprotection of the Cbz group under standard condition such as hydrogenation with palladium on carbon gives the desired tert-leucine amide 14.

EXAMPLES

Intermediate 15: Preparation of tert-butyl 3-(3,4-difluorophenyl)-6,7-dihydro-1H-pyrazolo[4,3-c]pyridine-5(4H)-carboxylate (15).

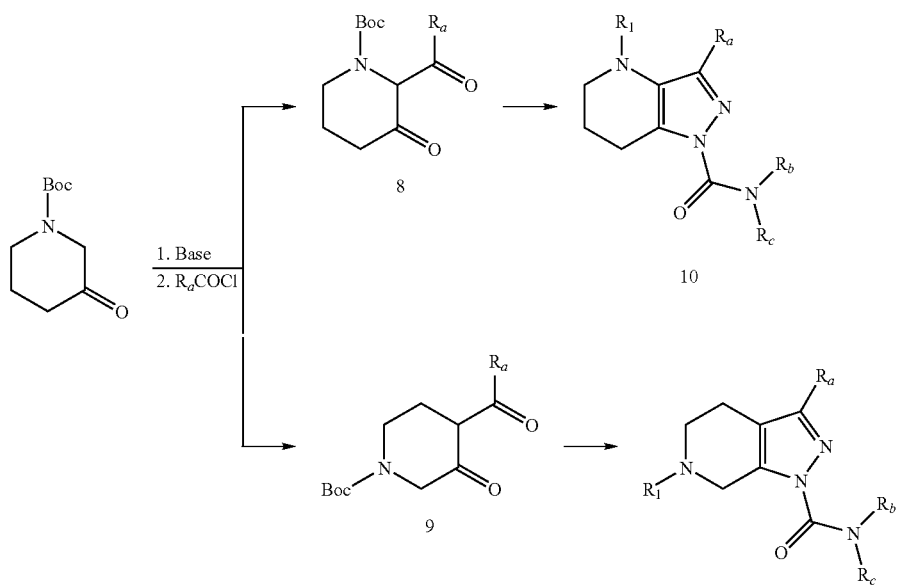

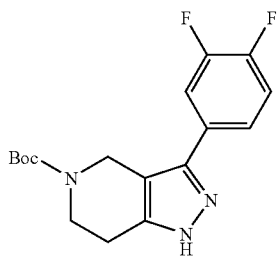

15

To a solution of 1-Boc-4-piperidone (3.0 g, 15.1 mmol) in anhydrous THF (30 mL) cooled in an ice-water bath was added LHMDS (1.0 M in THF, 16 mL). After stirring for 2 min, 3,4-difluorobenzoyl chloride (1.5 mL) was added and stirred for 2 min. Acetic acid (3 mL) was added and the reaction vessel was removed from the cooling bath. To the resulting white slurry was added MeOH (5 mL) followed by hydrazine monohydrate (3 mL) and stirred at room temperature for 30 min. After evaporation of THF, the residue was extracted with EtOAc and aqueous sodium bicarbonate. The organic phase was separated and evaporated under reduced pressure. The residue was purified by column chromatography using a gradient of from 30% to 50% EtOAc in hexanes to give a white solid product (2.56 g, 60% yield). LCMS (+ESI) m/z=336 [M+H]$^+$.

Intermediates 16-22: Following the procedures described for the synthesis of 15, intermediates 16-22 were prepared using the appropriate ketone starting material and corresponding acyl chloride. For example, intermediate 16 was prepared by replacing 1-Boc-4-piperidone with tetrahydro-4H-pyran-4-one; intermediate 17 was prepared by replacing 1-Boc-4-piperidone with tetrahydro-4H-pyran-4-one, and 3,4-difluorobenzoyl chloride with 2,4,5-trifluorobenzoyl chloride. 16-22 have the following structures:

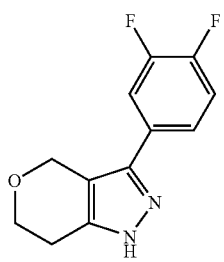

16

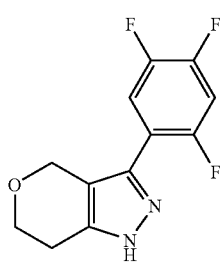

17

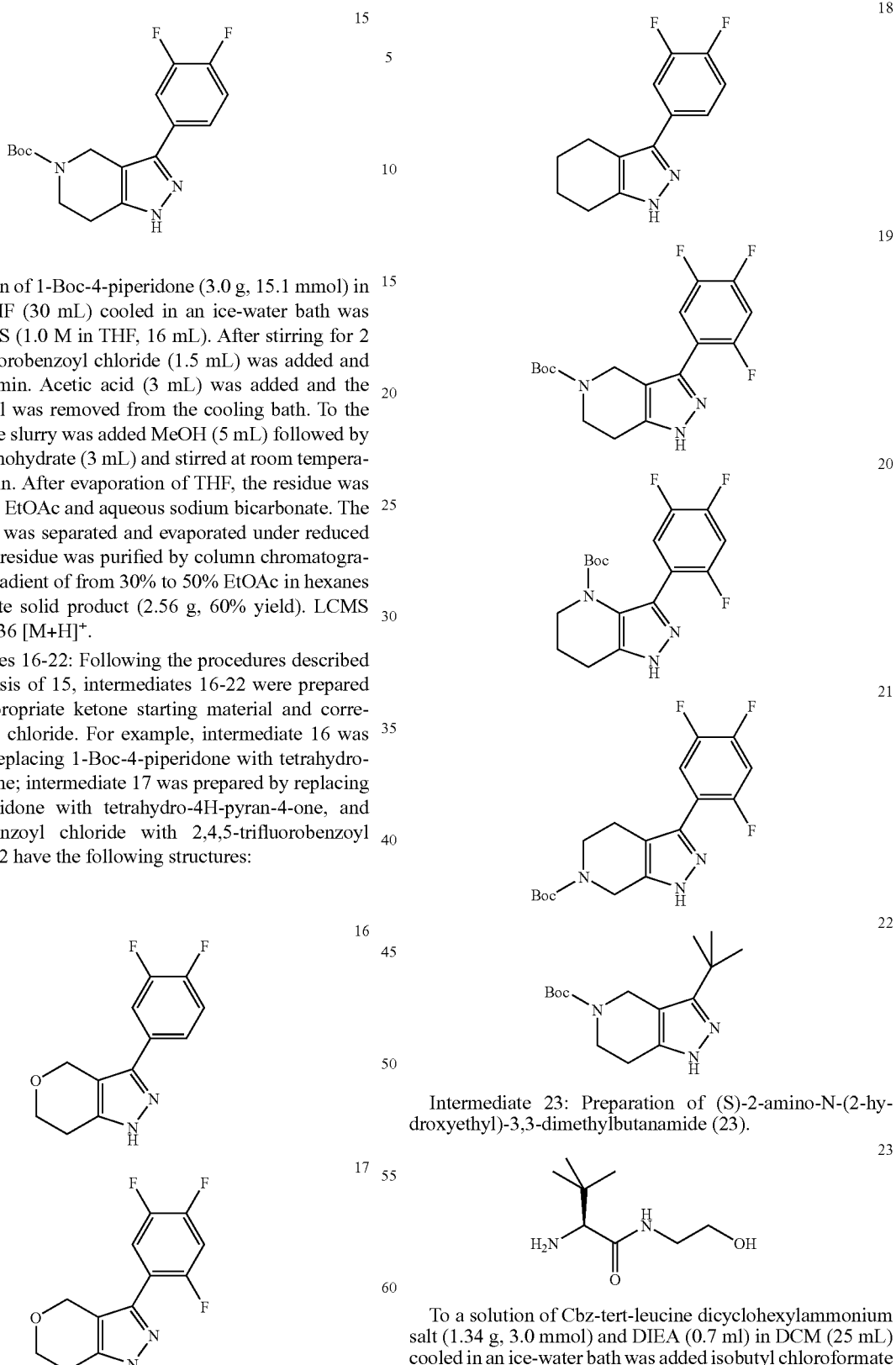

Intermediate 23: Preparation of (S)-2-amino-N-(2-hydroxyethyl)-3,3-dimethylbutanamide (23).

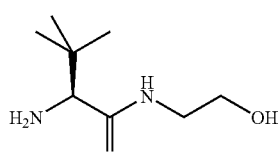

23

To a solution of Cbz-tert-leucine dicyclohexylammonium salt (1.34 g, 3.0 mmol) and DIEA (0.7 ml) in DCM (25 mL) cooled in an ice-water bath was added isobutyl chloroformate (0.47 mL, 3.6 mmol). After stirring at 0° C. for 1 h, ethanolamine was added (0.52 mL, 9.0 mmol) and stirred overnight. The reaction was quenched with saturated aqueous sodium bicarbonate. The organic phase was separated and dried over sodium sulfate. After evaporation under reduced pressure, the residue was dissolved in MeOH and passed through a SCX (Phenomenex®, Torrance, Calif.) cationic ion-exchange column to remove dicyclohexylamine and DIEA. The filtrate was evaporated and hydrogenated with Pd/C (0.5 g) under 45 psi hydrogen in MeOH for 4 h. Palladium catalyst was removed by filtration through celite. The filtrate was concentrated and dried under vacuum overnight to give intermediate 23 (0.35 g), which was used without further purification. LCMS (+ESI) m/z=175 [M+H]+.

Intermediates 24-27: Following the procedures described for the synthesis of 23, intermediates 24-27 were prepared using the appropriate amine. For example, intermediate 26 was prepared by replacing ethanolamine with 4-hydroxypiperidine.

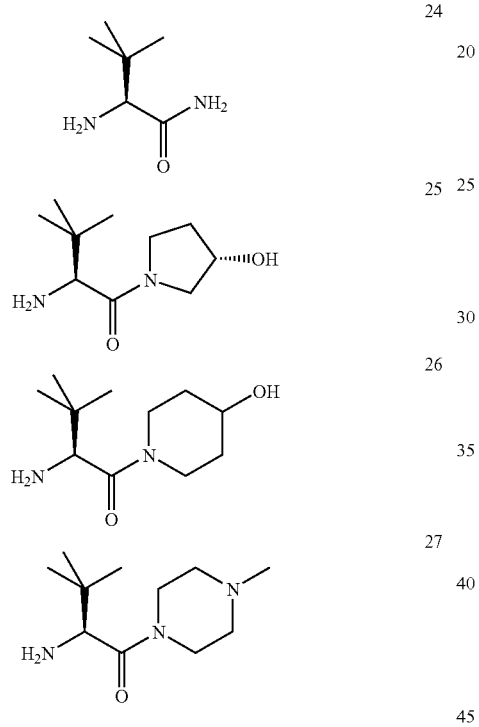

The following compounds were synthesized as described in the detailed methods exemplified below:

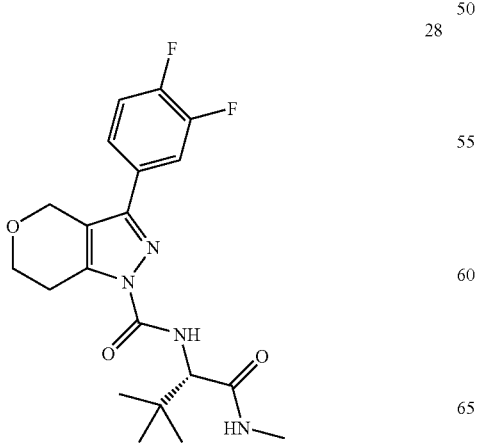

-continued

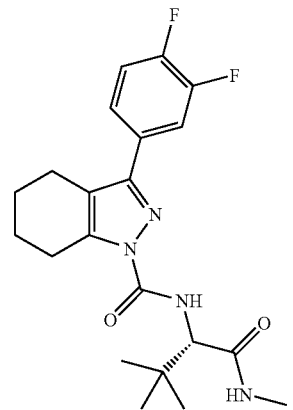

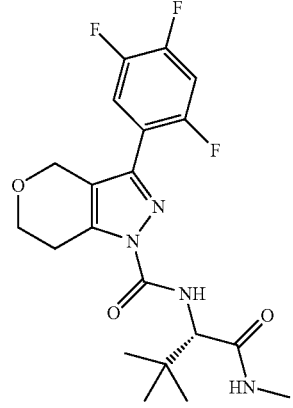

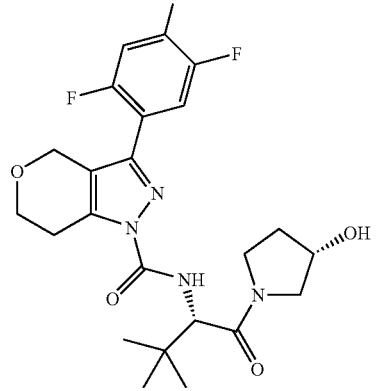

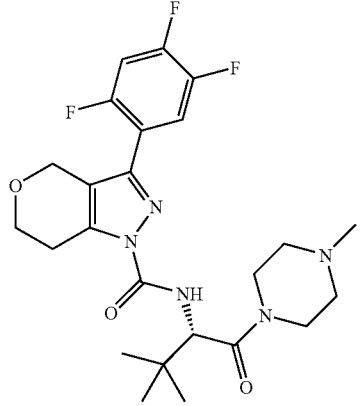

33
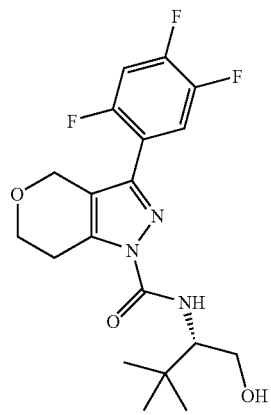
34
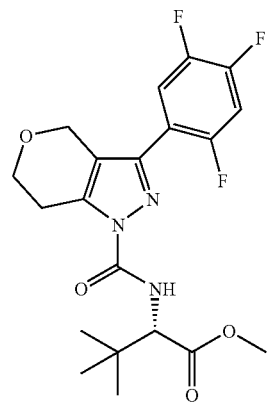
35
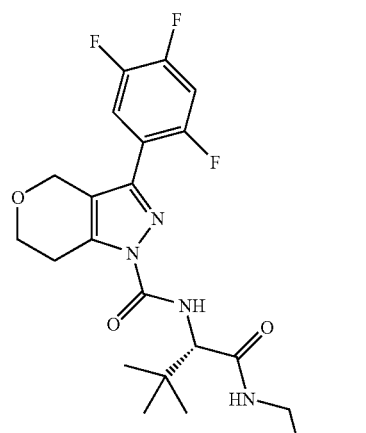
36
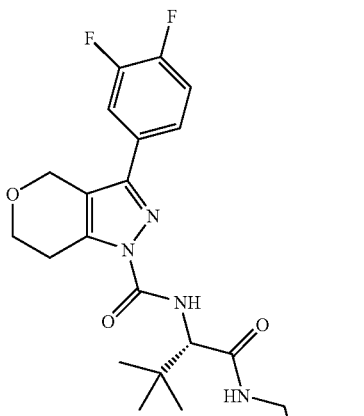
37
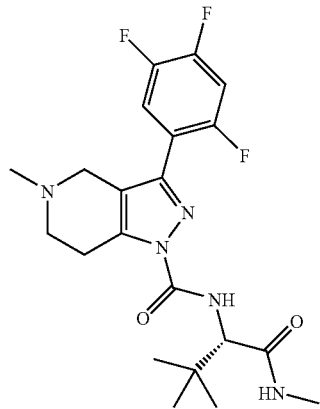
38
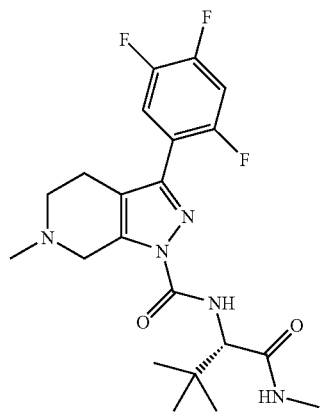

39
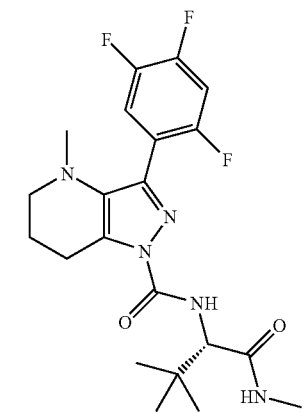
40
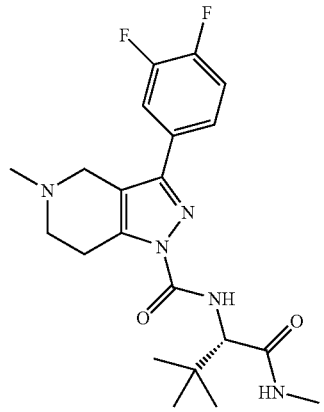
41
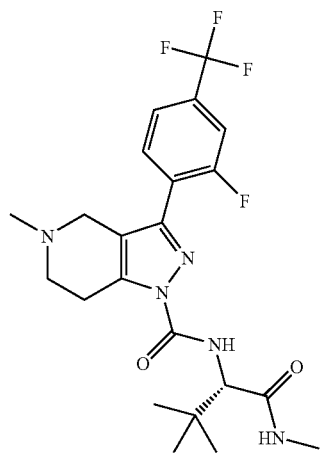
42
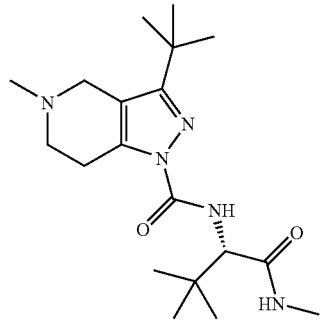
43
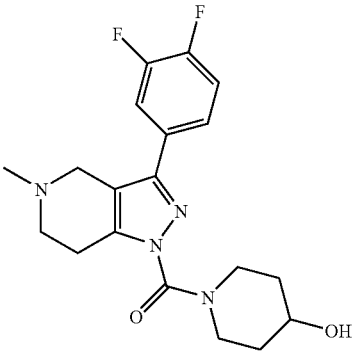
44
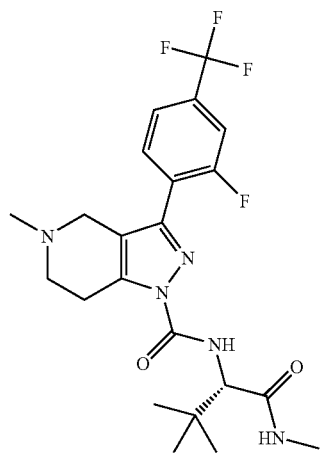
45
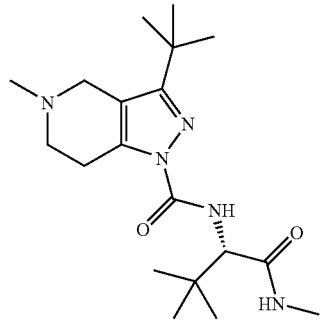

46
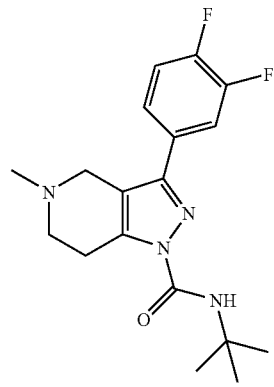
47
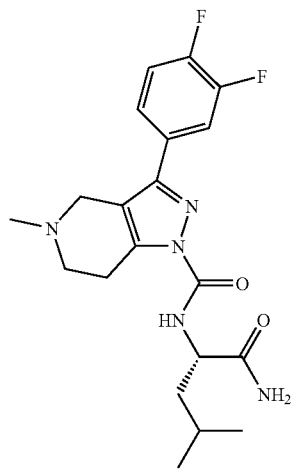
48
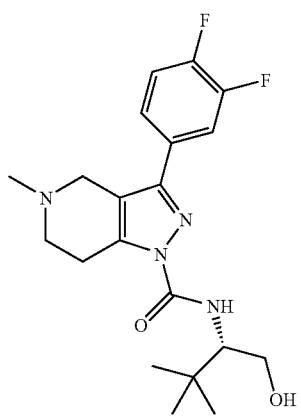
49
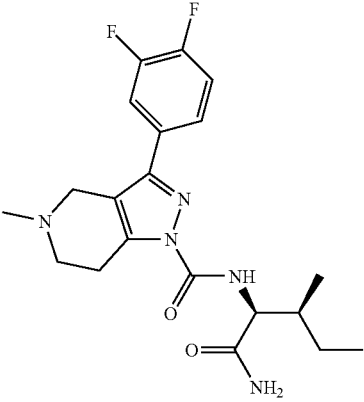
50
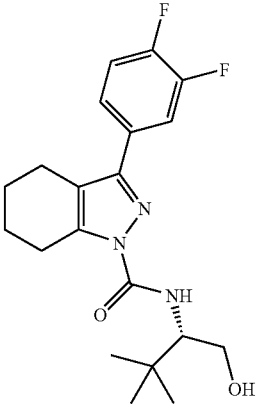
51

52 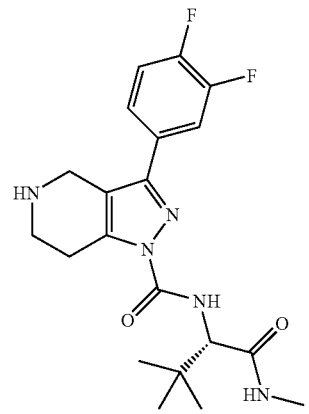
53 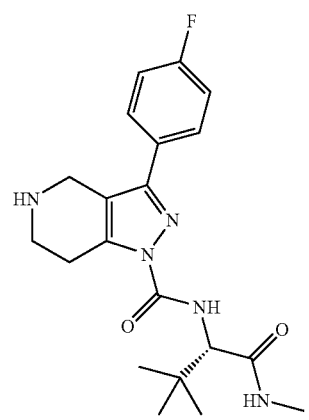
54 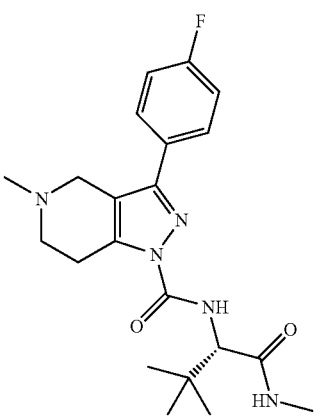
55 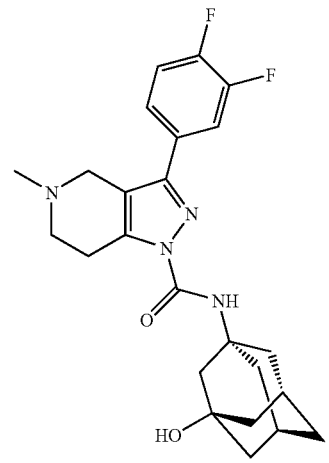
56 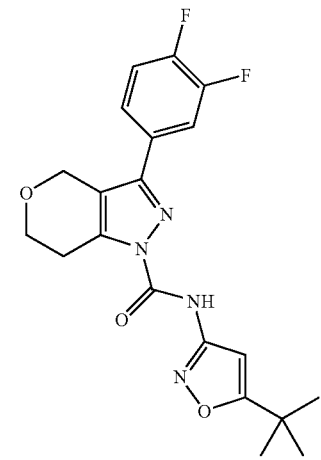
57

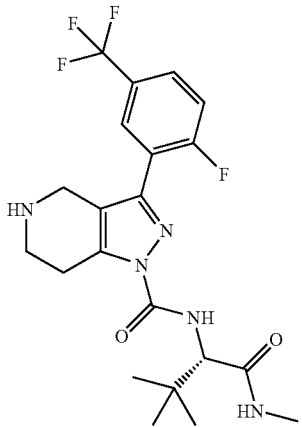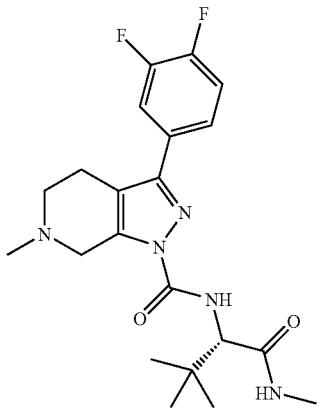

65
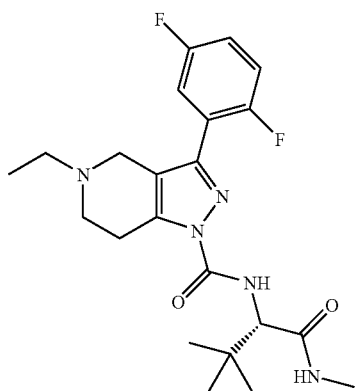
66
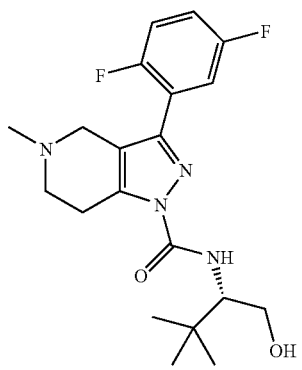
67
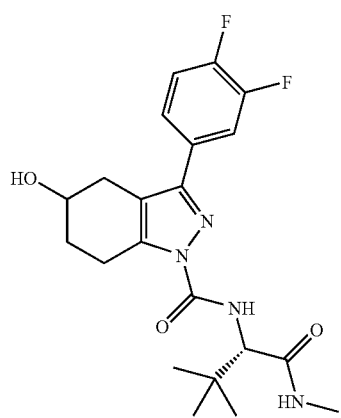
68
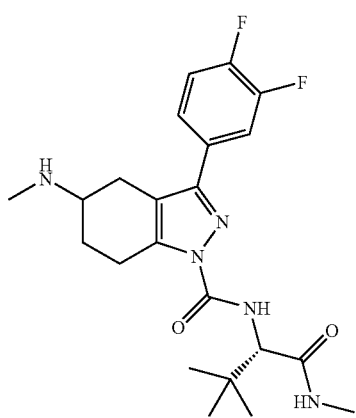
69
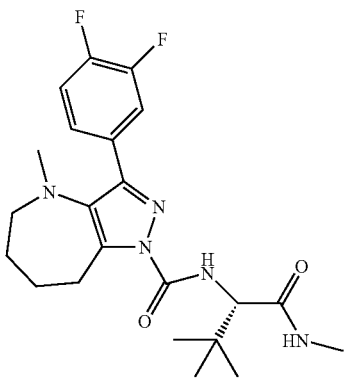
70
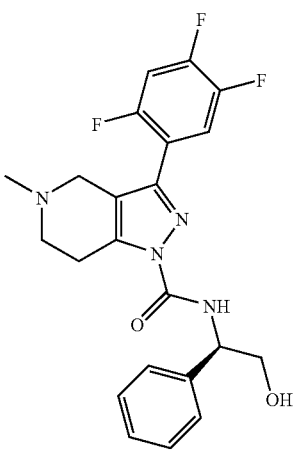
71

72 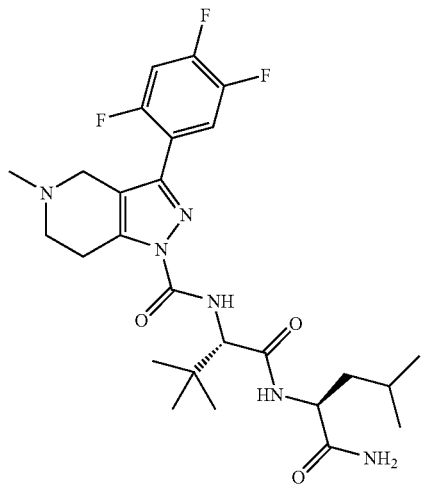
73 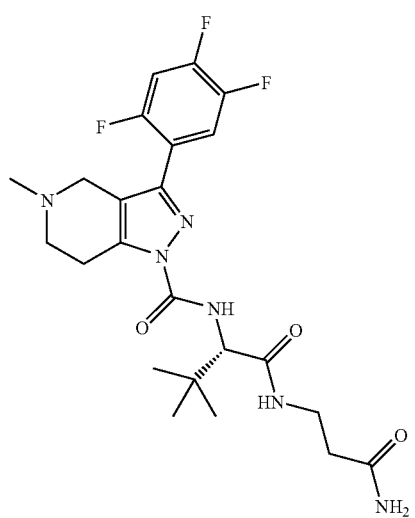
74 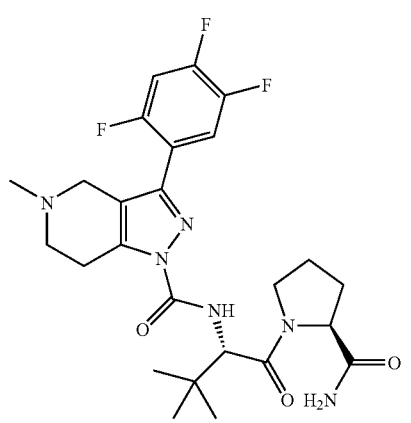
75 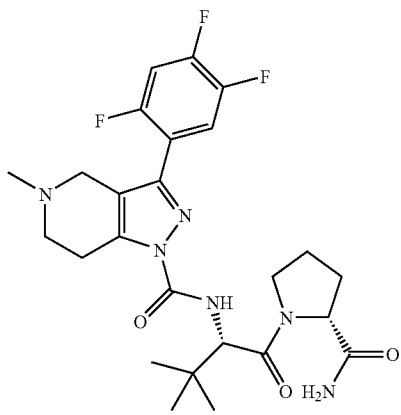
76 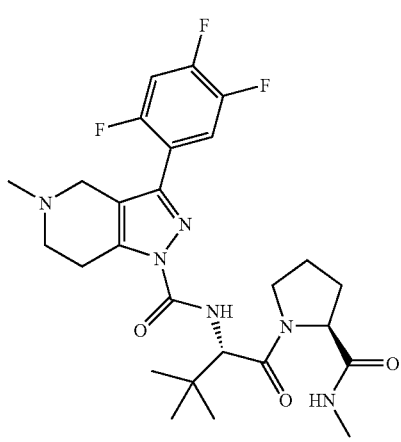
77 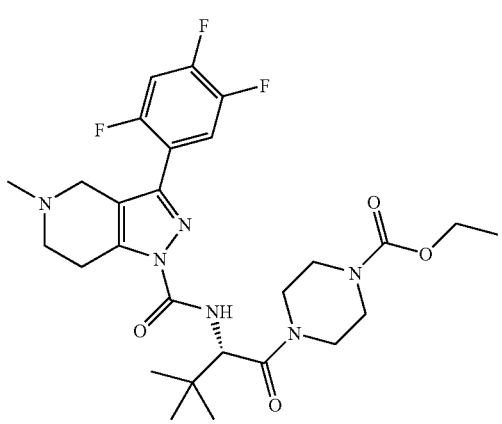

78
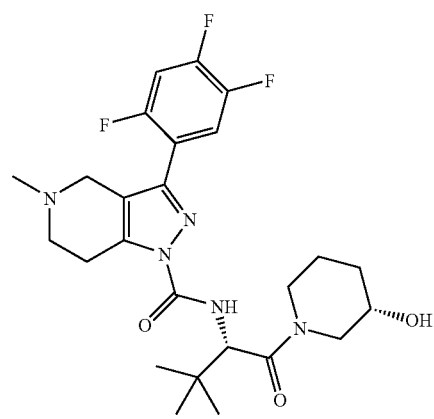
79
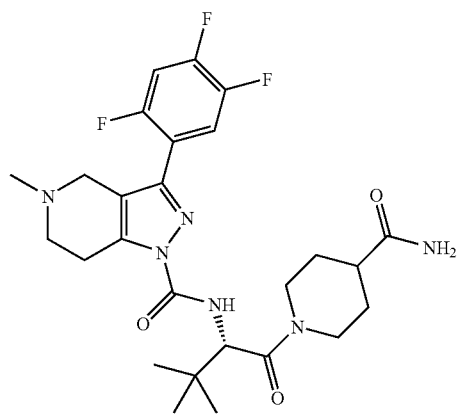
80
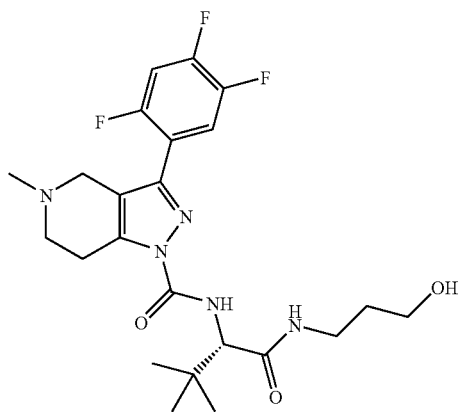
81
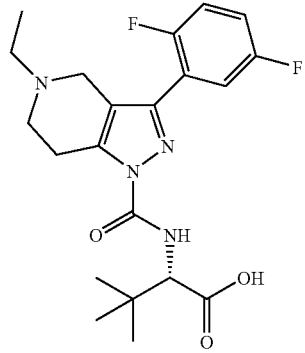
82
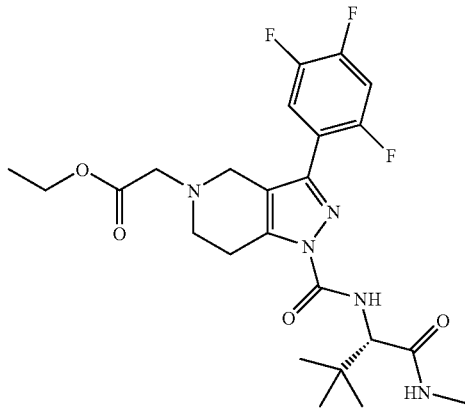
83
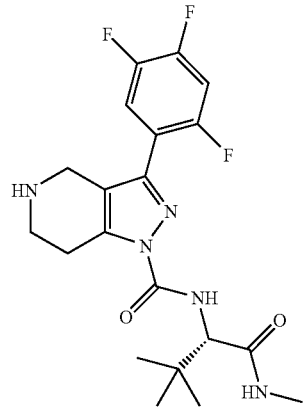
84
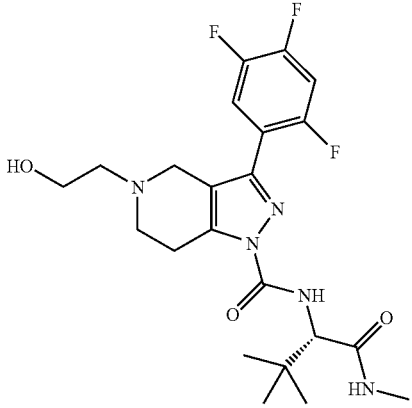
85

39
-continued
86
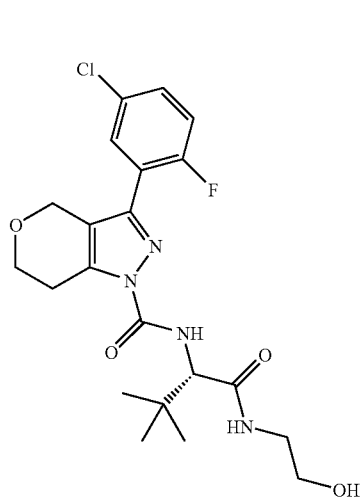
87
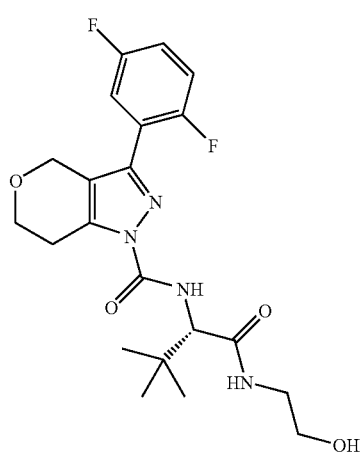
88
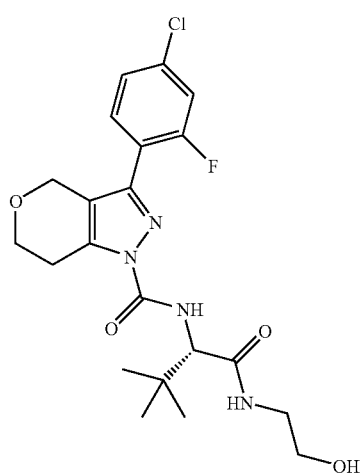
40
-continued
89
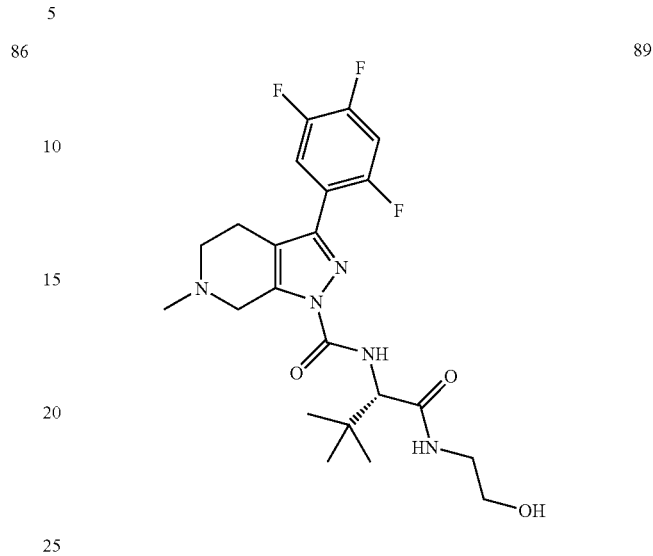
90
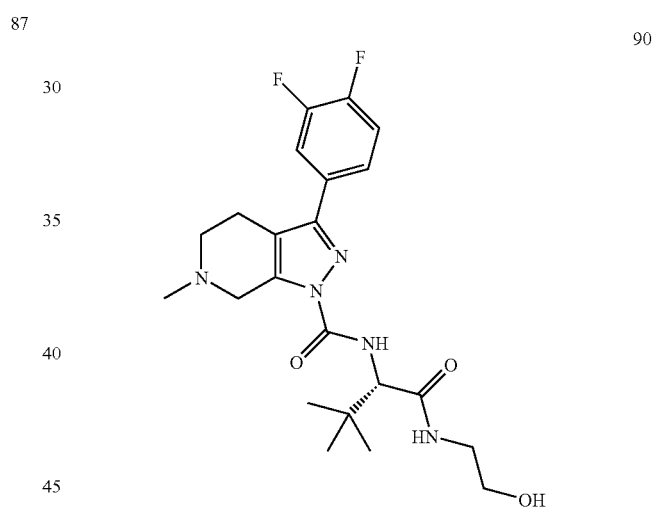
91
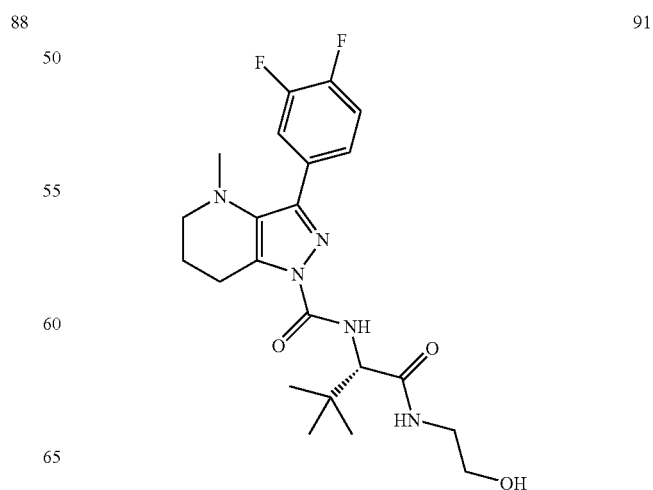

-continued
92
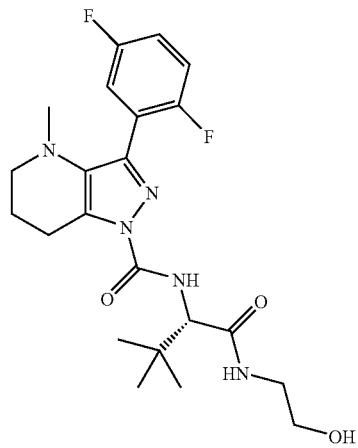
93
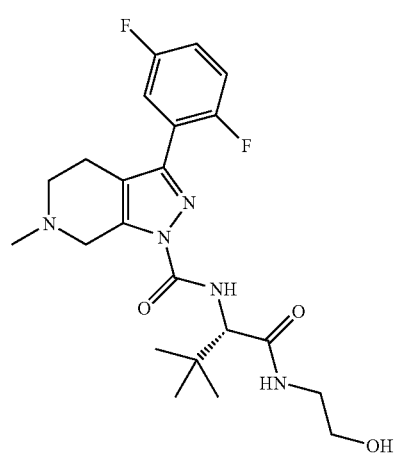
94
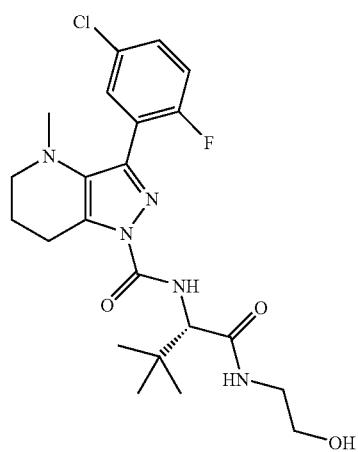
-continued
95
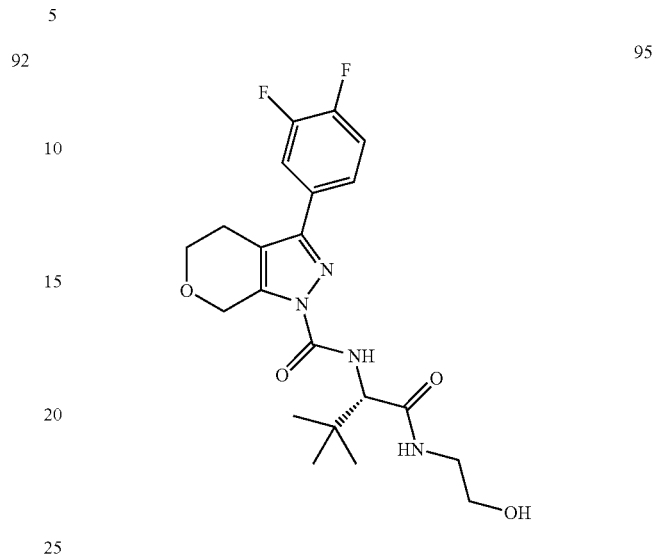
96
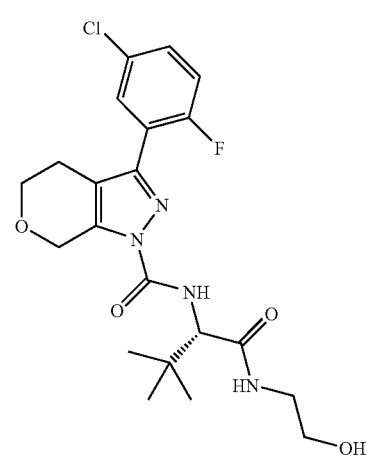
97
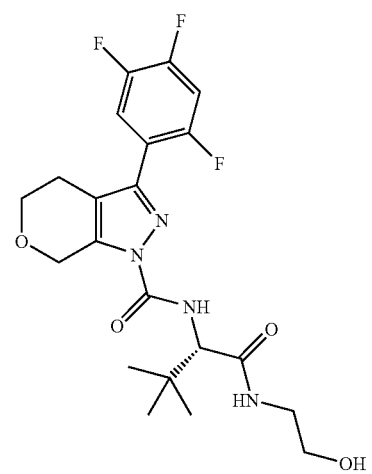

-continued

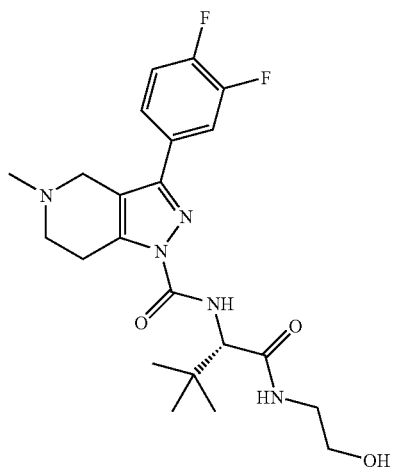

98

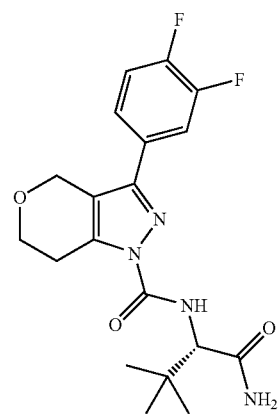

99

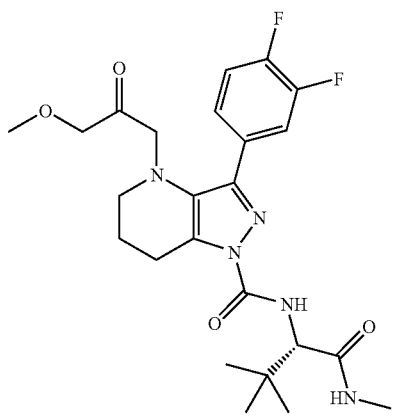

100

-continued

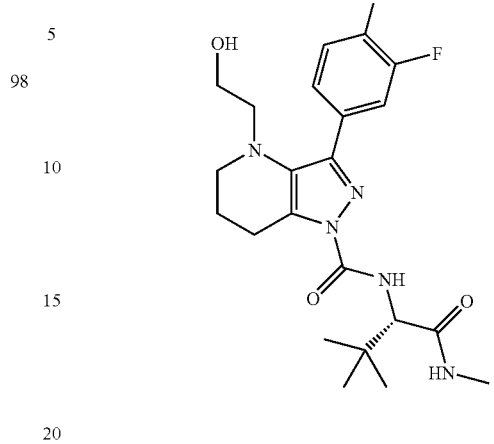

101

Example 1

Preparation of (S)-3-(3,4-difluorophenyl)-N-(3,3-dimethyl-1-(methyl-amino)-1-oxobutan-2-yl)-6,7-dihydropyrano[4,3-c]pyrazole-1(4H)-carboxamide (28). To a solution of intermediate 16 (225 mg, 0.95 mmol) in DCM was added DIEA (2.5 equiv) followed by phosgene (20% in toluene, 0.7 mL) at 0° C. After stirring for 15 min, tert-leucine methylamide (160 mg, 1.11 mmol) was added and stirred for 15 min. The reaction was quenched with saturated aqueous sodium bicarbonate. The organic phase was separated and dried over solid sodium sulfate. After evaporation under reduced pressure, the residue was purified by column chromatography with 35% to 70% EtOAc/hexanes to give solid product 28 (368 mg, 93% yield). $^1$H NMR (CDCl$_3$) δ 7.90 (d, J=9.4 Hz, 1H), 7.47-7.52 (m, 1H), 7.29-7.33 (m, 1H), 7.19-7.24 (m, 1H), 5.70 (br, 1H), 4.83 (s, 2H), 4.10 (d, J=9.4 Hz, 1H), 3.94 (t, J=5.6 Hz, 2H), 3.20 (br, 2H), 2.85 (d, J=4.4 Hz, 3H), 1.08 (s, 9H). LCMS (+ESI) m/z=407 [M+H]$^+$.

Example 2

Preparation of (S)-3-(3,4-difluorophenyl)-N-(3,3-dimethyl-1-(methylamino)-1-oxobutan-2-yl)-4,5,6,7-tetrahydro-1H-indazole-1-carboxamide (29). Compound 29 was prepared according to the procedure described for the synthesis of compound 28 by replacing intermediate 16 with intermediate 18. $^1$H NMR (CDCl$_3$) δ 7.91 (d, J=9.4 Hz, 1H), 7.58-7.63 (m, 1H), 7.49-7.53 (m, 1H), 7.18-7.25 (m, 1H), 5.78 (br, 1H), 4.10 (d, J=9.4 Hz, 1H), 3.01-3.07 (m, 2H), 2.84 (d, J=4.9 Hz, 3H), 2.65-2.68 (m, 2H), 1.75-1.86 (m, 4H), 1.08 (s, 9H). LCMS (+ESI) m/z=405 [M+H]$^+$.

Example 3

Preparation of (S)—N-(3,3-dimethyl-1-(methylamino)-1-oxobutan-2-yl)-3-(2,4,5-trifluorophenyl)-6,7-dihydropyrano[4,3-c]pyrazole-1(4H)-carboxamide (30). Compound 30 was prepared according to the procedure described for the synthesis of compound 28 by replacing intermediate 16 with intermediate 17. $^1$H NMR (CDCl$_3$) δ 7.88 (d, J=9.4 Hz, 1H), 7.56-7.63 (m, 1H), 6.98-7.04 (m, 1H), 5.75 (br, 1H), 4.65 (s, 2H), 4.12 (d, J=9.4 Hz, 1H), 3.94-4.00 (m, 2H), 3.16-3.20 (m, 2H), 2.87 (d, J=4.4 Hz, 3H), 1.09 (s, 9H). LCMS (+ESI) m/z=425 [M+H]$^+$.

Example 4

Preparation of N—((S)-1-((S)-3-hydroxypyrrolidin-1-yl)-3,3-dimethyl-1-oxobutan-2-yl)-3-(2,4,5-trifluorophenyl)-6,7-dihydropyrano[4,3-c]pyrazole-1(4H)-carboxamide (31). Compound 31 was prepared according to the procedure described for the synthesis of compound 28 by replacing intermediate 16 with intermediate 17, and replacing tert-leucine methylamide with intermediate 25.

$^1$H NMR (CDCl$_3$) δ 7.85 (d, J=9.7 Hz, 1H), 7.57-7.63 (m, 1H), 6.97-7.04 (m, 1H), 4.50-4.65 (m, 3H), 3.88-3.96 (m, 3H), 3.49-3.77 (m, 4H), 3.18 (br, 2H), 1.95-2.10 (m, 2H), 1.10 (s, 9H). LCMS (+ESI) m/z=481 [M+H]$^+$.

Example 5

Preparation of (S)—N-(3,3-dimethyl-1-(4-methylpiperazin-1-yl)-1-oxobutan-2-yl)-3-(2,4,5-trifluorophenyl)-6,7-dihydropyrano[4,3-c]pyrazole-1(4H)-carboxamide (32). Compound 32 was prepared according to the procedure described for the synthesis of compound 28 by replacing intermediate 16 with intermediate 17, and replacing tert-leucine methylamide with intermediate 27. $^1$H NMR (CDCl$_3$) δ 8.26 (s, 1H), 7.89 (d, J=9.5 Hz, 1H), 7.55-7.62 (m, 1H), 6.98-7.04 (m, 1H), 4.80 (d, J=9.5 Hz, 1H), 4.65 (s, 2H), 4.08 (br, 1H), 3.92-3.99 (m, 3H), 3.74-3.79 (m, 1H), 3.54-3.60 (m, 1H), 3.17-3.20 (br, 2H), 2.83-2.92 (br, 2H), 2.59-2.72 (br, 2H), 2.49 (s, 3H), 1.08 (s, 9H). LCMS (+ESI) m/z=494 [M+H]$^+$.

Example 6

Preparation of (S)—N-(1-hydroxy-3,3-dimethylbutan-2-yl)-3-(2,4,5-trifluorophenyl)-6,7-dihydropyrano[4,3-c]pyrazole-1(4H)-carboxamide (33). Compound 33 was prepared according to the procedure described for the synthesis of compound 28 by replacing intermediate 16 with intermediate 17, and replacing tert-leucine methylamide with tert-leucinol. $^1$H NMR (CDCl$_3$) δ 7.49-7.56 (m, 1H), 7.36 (d, J=9.6 Hz, 1H), 6.98-7.05 (m, 1H), 4.65 (s, 2H), 3.92-4.00 (m, 3H), 3.82-3.87 (m, 1H), 3.70 (s, 1H), 3.68-3.72 (m, 1H), 3.19-3.23 (br, 2H), 1.04 (s, 9H). LCMS (+ESI) m/z=398 [M+H]$^+$.

Example 7

Preparation of (S)-methyl 3,3-dimethyl-2-(3-(2,4,5-trifluorophenyl)-1,4,6,7-tetrahydropyrano[4,3-c]pyrazole-1-carboxamido)butanoate (34). Compound 34 was prepared according to the procedure described for the synthesis of compound 28 by replacing intermediate 16 with intermediate 17, and replacing tert-leucine methylamide with tert-leucine methyl ester. $^1$H NMR (CDCl$_3$) δ 7.72 (d, J=9.6 Hz, 1H), 7.53-7.60 (m, 1H), 6.99-7.05 (m, 1H), 4.65 (s, 2H), 4.42 (d, J=9.6 Hz, 1H), 3.95 (t, J=5.7 Hz, 2H), 3.78 (s, 3H), 3.17-3.21 (m, 2H), 1.08 (s, 9H). LCMS (+ESI) m/z=426 [M+H]$^+$.

Example 8

Preparation of (S)—N-(1-(2-hydroxyethylamino)-3,3-dimethyl-1-oxobutan-2-yl)-3-(2,4,5-trifluorophenyl)-6,7-dihydropyrano[4,3-c]pyrazole-1(4H)-carboxamide (35). Compound 35 was prepared according to the procedure described for the synthesis of compound 28 by replacing intermediate 16 with intermediate 17, and replacing tert-leucine methylamide with intermediate 23. $^1$H NMR (CDCl$_3$) δ 7.87 (d, J=9.1 Hz, 1H), 7.54-7.61 (m, 1H), 6.98-7.05 (m, 1H), 6.66 (t, J=5.6 Hz, 1H), 4.64 (s, 2H), 4.20 (d, J=9.2 Hz, 1H), 3.94 (t, J=5.7 Hz, 2H), 3.73 (br, 2H), 3.44-3.48 (m, 2H), 3.14-3.18 (m, 2H), 1.10 (s, 9H). LCMS (+ESI) m/z=455 [M+H]$^+$.

Example 9

Preparation of (S)—N-(1-(2-hydroxyethylamino)-3,3-dimethyl-1-oxobutan-2-yl)-3-(3,4-difluorophenyl)-6,7-dihydropyrano[4,3-c]pyrazole-1(4H)-carboxamide (36). Compound 36 was prepared according to the procedure described for the synthesis of compound 28 by replacing tert-leucine methylamide with intermediate 23. $^1$H NMR (CDCl$_3$) δ 7.89 (d, J=9.1 Hz, 1H), 7.46-7.51 (m, 1H), 7.21-7.30 (m, 2H), 4.82 (s, 2H), 4.20 (d, J=9.0 Hz, 1H), 3.94 (t, J=5.5 Hz, 2H), 3.74 (br, 2H), 3.44-3.49 (m, 2H), 3.17 (br, 2H), 1.11 (s, 9H). LCMS (+ESI) m/z=437 [M+H]$^+$.

Example 10

Preparation of (S)—N-(3,3-dimethyl-1-(methylamino)-1-oxobutan-2-yl)-5-methyl-3-(2,4,5-trifluorophenyl)-4,5,6,7-tetrahydro-1H-pyrazolo[4,3-c]pyridine-1-carboxamide (37).

Step 1: To a solution of intermediate 19 (0.89 g, 2.52 mmol) in DCM was added DIEA (1.1 mL) followed by phosgene (20% in toluene, 2.0 mL) at 0° C. After stirring for 30 min, tert-leucine methylamide (0.54 g, 3.74 mmol) was added and stirred for 30 min. The reaction was quenched with saturated aqueous sodium bicarbonate. The organic phase was decanted and dried over sodium sulfate. After evaporation under vacuum, the residue was purified by column chromatography with a gradient of from 20% to 50% EtOAc in hexanes to give (S)-tert-butyl 1-(3,3-dimethyl-1-(methylamino)-1-oxobutan-2-ylcarbamoyl)-3-(2,4,5-trifluorophenyl)-6,7-dihydro-1H-pyrazolo[4,3-c]pyridine-5(4H)-carboxylate (0.92 g, 70% yield). LCMS (+ESI) m/z=524 [M+H]$^+$.

Step 2: A solution of (S)-tert-butyl 1-(3,3-dimethyl-1-(methylamino)-1-oxobutan-2-ylcarbamoyl)-3-(2,4,5-trifluorophenyl)-6,7-dihydro-1H-pyrazolo[4,3-c]pyridine-5(4H)-carboxylate (0.92 g, 1.76 mmol) in TFA/DCM (1:1) was stirred at room temperature for 30 min. The reaction mixture was diluted with toluene and evaporated under vacuum. The resulting residue was dissolved in THF, to which formaldehyde (37%, 0.65 mL) and sodium triacetoxyborohydride (424 mg) was added sequentially. After stifling at room temperature for 2 h, THF was evaporated under vacuum. The residue was extracted between EtOAc and saturated aqueous sodium bicarbonate. The organic phase was dried over sodium sulfate and evaporated to dryness. The crude mixture was purified by column with a gradient of from 10% to 40% ethanol in MeCN to give (S)—N-(3,3-dimethyl-1-(methylamino)-1-oxobutan-2-yl)-5-methyl-3-(2,4,5-trifluoro-phenyl)-4,5,6,7-tetrahydro-1H-pyrazolo[4,3-c]pyridine-1-carboxamide 37 as a solid (412 mg, 49% yield for two steps). $^1$H NMR (CDCl$_3$) δ 7.86 (d, J=9.4 Hz, 1H), 7.47-7.54 (m, 1H), 6.98-7.04 (m, 1H), 5.85 (br, 1H), 4.11 (d, J=9.4 Hz, 1H), 3.39 (s, 2H), 3.16-3.20 (m, 2H), 2.84 (d, J=4.8 Hz, 3H), 2.73 (t, J=6.2 Hz, 2H), 2.47 (s, 3H), 1.05 (s, 9H). LCMS (+ESI) m/z=438 [M+H]$^+$.

Example 11

Preparation of (S)—N-(3,3-dimethyl-1-(methylamino)-1-oxobutan-2-yl)-6-methyl-3-(2,4,5-trifluorophenyl)-4,5,6,7-tetrahydro-1H-pyrazolo[3,4-c]pyridine-1-carboxamide (38)

Compound 38 was prepared according to the procedure described for the synthesis of compound 37 by replacing intermediate 19 with intermediate 21. $^1$H NMR (CDCl$_3$) δ 7.85 (d, J=9.4 Hz, 1H), 7.46-7.53 (m, 1H), 6.98-7.05 (m, 1H), 6.00 (br, 1H), 4.13 (d, J=9.4 Hz, 1H), 3.94-4.13 (m, 1H), 2.83 (d, J=4.8 Hz, 3H), 2.63-2.74 (m, 4H), 2.53 (s, 3H), 1.08 (s, 9H). LCMS (+ESI) m/z=438 [M+H]$^+$.

Example 12

Preparation of (S)—N-(3,3-dimethyl-1-(methylamino)-1-oxobutan-2-yl)-4-methyl-3-(2,4,5-trifluorophenyl)-4,5,6,7-tetrahydro-1H-pyrazolo[4,3-b]pyridine-1-carboxamide (39) Compound 39 was prepared according to the procedure described for the synthesis of compound 37 by replacing intermediate 19 with intermediate 20. $^1$H NMR (CDCl$_3$) δ 7.78 (d, J=9.2 Hz, 1H), 7.52-7.58 (m, 1H), 6.99-7.05 (m, 1H), 5.77 (br, 1H), 4.08 (d, J=9.3 Hz, 1H), 3.01-3.10 (m, 2H), 2.96-3.00 (m, 2H), 2.82 (d, J=4.8 Hz, 3H), 2.42 (s, 3H), 1.88-2.00 (m, 2H), 1.07 (s, 9H). LCMS (+ESI) m/z=438 [M+H]$^+$.

Example 13

Preparation of (S)—N-(1-(2-hydroxyethylamino)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (40) Compound 40 was prepared according to the procedure described for the synthesis of compound 37 by replacing tert-leucine methyl amide with intermediate 23. $^1$H NMR (CDCl$_3$) δ 7.87 (d, J=9.2 Hz, 1H), 7.47-7.53 (m, 1H), 6.98-7.05 (m, 1H), 6.81 (br, 1H), 4.21 (d, J=9.2 Hz, 1H), 3.69 (br, 2H), 3.39-3.43 (m, 4H), 3.17 (br, 2H), 2.74 (t, J=5.9 Hz, 2H), 2.46 (s, 3H), 1.08 (s, 9H). LCMS (+ESI) m/z=468 [M+H]$^+$.

Example 14

Preparation of (S)—N-(1-amino-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (41) Compound 41 was prepared according to the procedure described for the synthesis of compound 37 by replacing tert-leucine methyl amide with tert-leucine carboxamide 24. $^1$H NMR (CDCl$_3$) δ 7.83 (d, J=9.3 Hz, 1H), 7.55-7.62 (m, 1H), 7.00-7.07 (m, 1H), 6.86 (br, 1H), 5.88 (br, 1H), 4.31 (d, J=9.3 Hz, 1H), 3.57 (br, 4H), 2.93 (s, 3H), 1.08 (s, 9H). LCMS (+ESI) m/z=424 [M+H]$^+$.

Example 15

Preparation of (S)-3-(3,4-difluorophenyl)-N-(3,3-dimethyl-1-(methylamino)-1-oxobutan-2-yl)-5-methyl-4,5,6,7-tetrahydro-1H-pyrazolo[4,3-c]pyridine-1-carboxamide (42) Compound 42 was prepared according to the procedure described for the synthesis of compound 37 by replacing intermediate 19 with intermediate 15. $^1$H NMR (CDCl$_3$) δ 7.89 (d, J=9.4 Hz, 1H), 7.49-7.55 (m, 1H), 7.39-7.43 (m, 1H), 7.19-7.25 (m, 1H), 5.80 (br, 1H), 4.11 (d, J=9.4 Hz, 1H), 3.57 (s, 2H), 3.16-3.20 (m, 2H), 2.84 (d, J=4.8 Hz, 3H), 2.73 (t, J=5.8 Hz, 2H), 2.53 (s, 3H), 1.08 (s, 9H). LCMS (+ESI) m/z=420 [M+H]$^+$.

Example 16

Preparation of (S)—N-(3,3-dimethyl-1-(methylamino)-1-oxobutan-2-yl)-3-(2-fluoro-4-(trifluoromethyl)phenyl)-5-methyl-4,5,6,7-tetrahydro-1H-pyrazolo[4,3-c]pyridine-1-carboxamide (43) Compound 43 was prepared according to the procedure described for the synthesis of compound 37 by replacing intermediate 19 with tert-butyl 3-(2-fluoro-4-(trifluoromethyl)phenyl)-6,7-dihydro-1H-pyrazolo[4,3-c]pyridine-5(4H)-carboxylate, which was prepared according to the procedure described for the synthesis of intermediate 15 by replacing 3,4-difluorobenzoyl chloride with 2-fluoro-4-trifluoro-benzoyl chloride. $^1$H NMR (CDCl$_3$) δ 7.92 (d, J=9.4 Hz, 1H), 7.83 (t, J=7.5 Hz, 1H), 7.50 (d, J=7.5 Hz, 1H), 7.42 (d, J=10.3 Hz, 1H), 6.17 (br, 1H), 4.17 (d, J=9.5 Hz, 1H), 3.52 (s, 2H), 3.21-3.28 (m, 2H), 2.79-2.89 (m, 5H), 2.51 (s, 3H), 1.08 (s, 9H). LCMS (+ESI) m/z=470 [M+H]$^+$.

Example 17

Preparation of (S)-3-tert-butyl-N-(3,3-dimethyl-1-(methylamino)-1-oxo-butan-2-yl)-5-methyl-4,5,6,7-tetrahydro-1H-pyrazolo[4,3-c]pyridine-1-carboxamide (44) Compound 44 was prepared according to the procedure described for the synthesis of compound 37 by replacing intermediate 19 with intermediate 22. LCMS (+ESI) m/z=364 [M+H]$^+$.

Example 18

Preparation of (3-(3,4-difluorophenyl)-5-methyl-4,5,6,7-tetrahydro-1H-pyrazolo[4,3-c]pyridin-1-yl)(4-hydroxypiperidin-1-yl)methanone (45) Compound 45 was prepared according to the procedure described for the synthesis of compound 37 by replacing intermediate 19 with intermediate 15, and replacing tert-leucine methyl amide with 4-hydroxypiperidine. $^1$H NMR (CDCl$_3$) δ 7.46-7.51 (m, 1H), 7.32-7.36 (m, 1H), 7.20 (q, J=8.9 Hz, 1H), 3.96-4.08 (m, 3H), 3.60 (s, 2H), 3.41-3.47 (m, 2H), 3.08 (t, J=5.6 Hz, 2H), 2.78 (t, J=5.8 Hz, 2H), 2.54 (s, 3H), 1.97-2.01 (m, 2H), 1.63-1.72 (m, 2H). LCMS (+ESI) m/z=377 [M+H]$^+$.

Example 19

Preparation of N-tert-butyl-3-(3,4-difluorophenyl)-5-methyl-4,5,6,7-tetrahydro-1H-pyrazolo[4,3-c]pyridine-1-carboxamide (46) Compound 46 was prepared according to the procedure described for the synthesis of compound 37 by replacing intermediate 19 with intermediate 15, and replacing tert-leucine methylamide with tert-butylamine. $^1$H NMR (CDCl$_3$) δ 7.47-7.52 (m, 1H), 7.21-7.31 (m, 2H), 4.06 (s, 2H), 3.43 (t, J=6.1 Hz, 2H), 3.20 (t, J=6.1 Hz, 2H0, 2.75 (3H), 1.48 (s, 9H). LCMS (+ESI) m/z=349.2 [M+H]$^+$.

Example 20

Preparation of 3-(3,4-difluorophenyl)-N—((S)-1-((S)-3-hydroxypyrrolidin-1-yl)-3,3-dimethyl-1-oxobutan-2-yl)-5-methyl-4,5,6,7-tetrahydro-1H-pyrazolo[4,3-c]pyridine-1-carboxamide (47) Compound 47 was prepared according to the procedure described for the synthesis of compound 37 by replacing intermediate 19 with intermediate 15, and replacing tert-leucine methylamide with intermediate 25. LCMS (+ESI) m/z=476.3 [M+H]$^+$.

Example 21

Preparation of (S)-3-(3,4-difluorophenyl)-N-(1-hydroxy-3,3-dimethylbutan-2-yl)-5-methyl-4,5,6,7-tetrahydro-1H-pyrazolo[4,3-c]pyridine-1-carboxamide (48) Compound 48 was prepared according to the procedure described for the synthesis of compound 37 by replacing intermediate 19 with intermediate 15, and replacing tert-leucine methylamide with tert-leucinol. $^1$H NMR (CDCl$_3$) δ 7.48-7.53 (m, 1H), 7.33-7.38 (m, 2H), 7.18-7.22 (m, 1H), 3.92-3.95 (m, 1H), 3.78-3.83 (m, 1H), 3.64-3.68 (m, 1H), 3.57 (s, 2H), 3.20 (m, 2H), 2.72-2.79 (m, 2H), 2.53 (s, 3H), 1.02 (s, 9H). LCMS (+ESI) m/z=393.2 [M+H]$^+$.

Example 22

Preparation of (S)—N-(1-amino-4-methyl-1-oxopentan-2-yl)-3-(3,4-difluorophenyl)-5-methyl-4,5,6,7-tetrahydro-1H-pyrazolo[4,3-c]pyridine-1-carboxamide (49) Compound 49 was prepared according to the procedure described for the synthesis of compound 37 by replacing intermediate 19 with intermediate 15, and replacing tert-leucine methylamide with L-leucine amide. $^1$H NMR (CDCl$_3$) δ 7.49-7.58 (m, 2H), 7.34-7.38 (m, 1H), 7.18-7.24 (m, 1H), 4.50 (m, 1H), 3.58 (s, 2H), 3.20 (s, 2H), 2.27 (s, 3H), 2.53 (s, 3H), 1.71-1.82 (m, 3H), 0.88-0.99 (m, 6H). LCMS (+ESI) m/z=406.3 [M+H]$^+$.

Example 23

Preparation of N-((2S,3S)-1-amino-3-methyl-1-oxopentan-2-yl)-3-(3,4-difluorophenyl)-5-methyl-4,5,6,7-tetrahydro-1H-pyrazolo[4,3-c]pyridine-1-carboxamide (50) Compound 50 was prepared according to the procedure described for the synthesis of compound 37 by replacing intermediate 19 with intermediate 15, and replacing tert-leucine methylamide with L-isoleucine amide.
$^1$H NMR (CDCl$_3$) δ 7.67 (d, J=8.8 Hz, 1H), 7.49-7.55 (m, 1H), 7.37-7.41 (m, 1H), 7.19-7.24 (m, 1H), 5.95 (s, 1H), 5.63 (s, 1H), 4.30-4.33 (m, 1H), 3.59 (s, 2H), 3.20 (s, 2H), 2.75-2.78 (m, 2H), 2.54 (s, 3H), 2.07-2.10 (m, 1H), 1.60-1.67 (m, 1H), 1.22-1.30 (m, 1H), 1.03 (d, J=6.8 Hz, 3H), 0.98 (t, J=7.4 Hz, 3H). LCMS (+ESI) m/z=406.2 [M+H]$^+$.

Example 24

Preparation of (S)-3-(3,4-difluorophenyl)-N-(1-hydroxy-3,3-dimethylbutan-2-yl)-4,5,6,7-tetrahydro-1H-indazole-1-carboxamide (51) Compound 51 was prepared according to the procedure described for the synthesis of compound 28 by replacing intermediate 16 with intermediate 18, and replacing tert-leucine methylamide with tert-leucinol. $^1$H NMR (CDCl$_3$) δ 7.54-7.60 (m, 1H), 7.41-7.47 (m, 2H), 7.17-7.23 (m, 1H), 6.95 (dd, J=7.3, 3.4 Hz, 1H), 3.80-3.86 (m, 1H), 3.65-3.70 (m, 1H), 3.04 (m, 2H), 2.64 (m, 2H), 1.74-1.84 (m, 4H), 1.04 (s, 9H). LCMS (+ESI) m/z=378.3 [M+H]$^+$.

Example 25

Preparation of (S)-3-(3,4-difluorophenyl)-N-(3,3-dimethyl-1-(methylamino)-1-oxobutan-2-yl)-4,5,6,7-tetrahydro-1H-pyrazolo[4,3-c]pyridine-1-carboxamide (52) Compound 52 was prepared according to the procedure described for the synthesis of compound 37 by replacing intermediate 19 with intermediate 15, without the reductive amination step with formaldehyde. $^1$H NMR (CDCl$_3$) δ 7.92 (d, J=9.4 Hz, 1H), 7.50-7.55 (m, 1H), 7.37-7.40 (m, 1H), 7.19-7.26 (m, 1H), 6.10 (br, 1H), 4.15 (d, J=9.4 Hz, 1H), 4.04 (s, 1H), 3.09-3.15 (m, 4H), 2.85 (d, J=4.8 Hz, 3H), 1.06 (s, 9H). LCMS (+ESI) m/z=406.2 [M+H]$^+$.

Example 26

Preparation of (S)—N-(3,3-dimethyl-1-(methylamino)-1-oxobutan-2-yl)-3-(4-fluorophenyl)-4,5,6,7-tetrahydro-1H-pyrazolo[4,3-c]pyridine-1-carboxamide (53) Compound 53 was prepared according to the procedure described for the synthesis of compound 52 by replacing 3,4-difluorobenzoyl chloride with 4-fluorobenzoyl chloride in the synthesis of intermediate 15. $^1$H NMR (CDCl$_3$) δ 7.96 (d, J=9.5 Hz, 1H), 7.65-7.69 (m, 2H), 7.10-7.15 (m, 2H), 6.27 (br, 1H), 4.18 (d, J=9.4 Hz, 1H), 4.02 (s, 2H), 3.05-3.15 (m, 4H), 2.85 (d, J=4.8 Hz, 3H), 1.10 (s, 9H). LCMS (+ESI) m/z=388.2 [M+H]$^+$.

Example 27

Preparation of (S)—N-(3,3-dimethyl-1-(methylamino)-1-oxobutan-2-yl)-3-(4-fluorophenyl)-5-methyl-4,5,6,7-tetrahydro-1H-pyrazolo[4,3-c]pyridine-1-carboxamide (54) Compound 54 was prepared by reductive amination of compound 53 with formaldehyde following the procedure as described for the synthesis of compound 37. $^1$H NMR (CDCl$_3$) δ 7.94 (d, J=9.5 Hz, 1H), 7.65-7.68 (m, 2H), 7.11-7.27 (m, 2H), 6.15 (br, 1H), 4.16 (d, J=9.5 Hz, 1H), 3.63 (s, 2H), 3.17-3.22 (m, 2H), 2.83 (d, J=4.8 Hz, 3H), 2.78 (br, 1H), 2.55 (s, 3H), 1.06 (s, 9H). LCMS (+ESI) m/z=402.3 [M+H]$^+$.

Example 28

Preparation of compound (55) Compound 55 was prepared according to the procedure described for the synthesis of compound 48 by replacing tert-leucinol with 3-aminoadmantan-1-ol. LCMS (+ESI) m/z=443.3 [M+H]$^+$.

Example 29

Preparation of N-(4-tert-butylthiazol-2-yl)-3-(3,4-difluorophenyl)-6,7-dihydropyrano[4,3-c]pyrazole-1(4H)-carboxamide (56) Compound 56 was prepared according to the procedure described for the synthesis of compound 28 by replacing tert-leucine methylamide with 2-amino-4-tert-butylthiazole. LCMS (+ESI) m/z=419.2 [M+H]$^+$.

Example 30

Preparation of N-(4-tert-butylthiazol-2-yl)-3-(3,4-difluorophenyl)-6,7-dihydropyrano[4,3-c]pyrazole-1(4H)-carboxamide (57) Compound 57 was prepared according to the procedure described for the synthesis of compound 28 by replacing tert-leucine methylamide with 3-amino-5-tert-butylisoxazole. LCMS (+ESI) m/z=403.2 [M+H]$^+$.

Example 31

Preparation of (S)—N-(3,3-dimethyl-1-(methylamino)-1-oxobutan-2-yl)-3-(2-fluoro-5-(trifluoromethyl)phenyl)-4,5,6,7-tetrahydro-1H-pyrazolo[4,3-c]pyridine-1-carboxamide (58) Compound 58 was prepared according to the procedure described for the synthesis of compound 52 by replacing 3,4-difluorobenzoyl chloride with 2-fluoro-5-trifluorobenzoyl chloride in the synthesis of intermediate 15. LCMS (+ESI) m/z=456.2 [M+H]$^+$.

Example 32

Preparation of (S)—N-(3,3-dimethyl-1-(methylamino)-1-oxobutan-2-yl)-3-(2-fluoro-5-(trifluoromethyl)phenyl)-5-methyl-4,5,6,7-tetrahydro-1H-pyrazolo[4,3-c]pyridine-1-carboxamide (59) Compound 59 was prepared reductive amination of compound 58 with formaldehyde following the procedure as described for the synthesis of compound 37. LCMS (+ESI) m/z=456.2 [M+H]$^+$.

Example 33

Preparation of 3-(3,4-difluorophenyl)-N—((S)-1-((S)-3-hydroxypyrrolidin-1-yl)-3,3-dimethyl-1-oxobutan-2-yl)-6,7-dihydropyrano[4,3-c]pyrazole-1(4H)-carboxamide (60) Compound 60 was prepared according to the procedure described for the synthesis of compound 28 by replacing tert-leucine methylamide with intermediate 25. LCMS (+ESI) m/z=463.3 [M+H]+.

Example 34

Preparation of (S)-3-(3,4-difluorophenyl)-N-(3,3-dimethyl-1-(methylamino)-1-oxobutan-2-yl)-6-methyl-4,5,6,7-tetrahydro-1H-pyrazolo[3,4-c]pyridine-1-carboxamide (61) Compound 61 was prepared according to the procedure described for the synthesis of compound 37 by replacing intermediate 19 with intermediate 21B (shown in Example 64). LCMS (+ESI) m/z=420.2 [M+H]+.

Example 35

Preparation of (S)-3-(3,4-difluorophenyl)-N-(3,3-dimethyl-1-(methylamino)-1-oxobutan-2-yl)-4-methyl-4,5,6,7-tetrahydro-1H-pyrazolo[4,3-b]pyridine-1-carboxamide (62) Compound 62 was prepared according to the procedure described for the synthesis of compound 37 by replacing intermediate 19 with intermediate 20B (shown in Example 64). LCMS (+ESI) m/z=420.2 [M+H]+.

Example 36

Preparation of (S)-3'-(3,4-difluorophenyl)-N-(3,3-dimethyl-1-(methylamino)-1-oxobutan-2-yl)-6',7'-dihydrospiro[[1,3]dioxolane-2,5'-indazole]-1'(4'H)-carboxamide (63) Compound 63 was prepared according to the procedure described for the synthesis of compound 28 by replacing tetrahydro-4H-pyran-4-one with 1,4-dioxaspiro[4.5]decan-8-one in the synthesis of intermediate 16. LCMS (+ESI) m/z=463.2 [M+H]+.

Example 37

Preparation of (S)-3-(2,5-difluorophenyl)-N-(3,3-dimethyl-1-(methylamino)-1-oxobutan-2-yl)-5-methyl-4,5,6,7-tetrahydro-1H-pyrazolo[4,3-c]pyridine-1-carboxamide (64) Compound 64 was prepared according to the procedure described for the synthesis of compound 37 by replacing 2,4,5-trifluorobenzoyl chloride with 2,5-difluorobenzoyl chloride in the synthesis of intermediate 19. LCMS (+ESI) m/z=420.2 [M+H]+.

Example 38

Preparation of (S)-3-(2,5-difluorophenyl)-N-(3,3-dimethyl-1-(methylamino)-1-oxobutan-2-yl)-5-ethyl-4,5,6,7-tetrahydro-1H-pyrazolo[4,3-c]pyridine-1-carboxamide (65) Compound 65 was prepared according to the procedure described for the synthesis of compound 64 by replacing formaldehyde with acetaldehyde. LCMS (+ESI) m/z=434.3 [M+H]+.

Example 39

Preparation of (S)-3-(2,5-difluorophenyl)-N-(1-hydroxy-3,3-dimethylbutan-2-yl)-5-methyl-4,5,6,7-tetrahydro-1H-pyrazolo[4,3-c]pyridine-1-carboxamide (66) Compound 66 was prepared according to the procedure described for the synthesis of compound 64 by replacing tert-leucine methylamide with tert-leucinol. LCMS (+ESI) m/z=393.3 [M+H]+.

Example 40

Preparation of 3-(3,4-difluorophenyl)-N—((S)-3,3-dimethyl-1-(methylamino)-1-oxobutan-2-yl)-5-hydroxy-4,5,6,7-tetrahydro-1H-indazole-1-carboxamide (67) A mixture of compound 63 (0.91 g) and p-toluenesulfonic acid (1.3 g) was heated in acetone and water at 50° C. until starting material was consumed. After evaporation of acetone, the residue was extracted between EtOAc and saturated sodium bicarbonate. The organic phase was dried over sodium sulfate and evaporated to dryness. The crude product was purified by column chromatography with 70% to 80% EtOAc/Hex to give (S)-3-(3,4-difluorophenyl)-N-(3,3-dimethyl-1-(methylamino)-1-oxobutan-2-yl)-5-oxo-4,5,6,7-tetrahydro-1H-indazole-1-carboxamide (0.75 g, 91% yield), which was reduced with sodium borohydride (1.0 equiv.) in MeOH to give compound 67 as a mixture of two diastereomers after purification with a preparative LC-MS. LCMS (+ESI) m/z=421.2 [M+H]+.

Example 41

Preparation of 3-(3,4-difluorophenyl)-N—((S)-3,3-dimethyl-1-(methylamino)-1-oxobutan-2-yl)-5-(methylamino)-4,5,6,7-tetrahydro-1H-indazole-1-carboxamide (68) A mixture of (S)-3-(3,4-difluorophenyl)-N-(3,3-dimethyl-1-(methylamino)-1-oxobutan-2-yl)-5-oxo-4,5,6,7-tetrahydro-1H-indazole-1-carboxamide (62 mg), methylamine (2.0 M in THF, 2.0 mL), acetic acid (15 uL) and sodium triacetoxyborohydride (30 mg) was stirred overnight. After evaporation of THF, the residue was extracted between EtOAc and saturated sodium bicarbonate. The organic phase was dried over sodium sulfate and evaporated to dryness. The crude product was purified with a preparative LC-MS to give compound 68. LCMS (+ESI) m/z=434.3 [M+H]+.

Example 42

Preparation of (S)-3-(3,4-difluorophenyl)-N-(3,3-dimethyl-1-(methylamino)-1-oxobutan-2-yl)-4-methyl-5,6,7,8-tetrahydropyrazolo[4,3-b]azepine-1(4H)-carboxamide (69) Compound 69 was prepared according to the procedure described for the synthesis of compound 37 except that 1-Boc-4-piperidone was replaced with tert-butyl 3-oxoazepane-1-carboxylate and 2,4,5-trifluorobenzoylchloride was replaced with 3,4-difluorobenzoylchloride. LCMS (+ESI) m/z=434.2 [M+H]+.

Example 43

Preparation of (R)—N-(2-hydroxy-1-phenylethyl)-5-methyl-3-(2,4,5-trifluorophenyl)-4,5,6,7-tetrahydro-1H-pyrazolo[4,3-c]pyridine-1-carboxamide (70) Compound 70 was prepared according to the procedure described for the synthesis of compound 37 by replacing tert-leucine methylamide with (R)-2-amino-2-phenylethanol. LCMS (+ESI) m/z=431.2 [M+H]+.

Example 44

Preparation of (S)-3,3-dimethyl-2-(5-methyl-3-(2,4,5-trifluorophenyl)-4,5,6,7-tetrahydro-1H-pyrazolo[4,3-c]pyridine-1-carboxamido)butanoic acid (71) To a solution of intermediate 19 (353 mg) in DCM was added DIEA (0.35 mL)

followed by phosgene (20% in toluene, 0.8 mL). After stirring at room temperature for 30 min, tert-leucine tert-butyl ester hydrochloride (268 mg) and DIEA (0.2 mL) was added. The reaction was stirred for 1.5 h at room temperature and quenched with aqueous sodium bicarbonate. The organic phase was separated and dried over sodium sulfate. After evaporation of DCM, the crude product was purified by column chromatography with 10% to 30% EtOAc/Hex to give (S)-tert-butyl 1-(1-tert-butoxy-3,3-dimethyl-1-oxobutan-2-ylcarbamoyl)-3-(2,4,5-trifluorophenyl)-6,7-dihydro-1H-pyrazolo[4,3-c]pyridine-5(4H)-carboxylate (0.45 g), which was stirred in TFA/DCM (1:1) for 2 h. After evaporation of TFA/DCM, the residue was dissolved in THF, to which formaldehyde (37% in water, 0.3 mL) was added followed by the addition sodium triacetoxyborohydride (300 mg). The reaction mixture was stirred at room temperature overnight. After evaporation of THF, the residue was dissolved in MeOH (10.0 mL) and 0.8 mL of the solution was purified by a preparative LC-MS to give compound 71. LCMS (+ESI) m/z=425.2 [M+H]+.

Example 45

Preparation of N—((S)-1-((S)-1-amino-4-methyl-1-oxopentan-2-ylamino)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (72) To a solution of compound 71 (40 mg) in DCM was added DIEA (45 uL) followed by isobutylchloroformate (26 uL). After stirring at room temperature for 30 min, leucine amide (18 mg) and DIEA (25 uL) was added and stirred for 1 h. The reaction mixture was evaporated and dissolved in MeOH, and purified with a preparative LC-MS to give compound 72. LCMS (+ESI) m/z=537.3 [M+H]+.

Example 46

Preparation of (S)—N-(1-(3-amino-3-oxopropylamino)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (73) Compound 73 was prepared according to the procedure described for the synthesis of compound 72 by replacing leucine amide with 3-aminopropanamide. LCMS (+ESI) m/z=495.4 [M+H]+.

Example 47

Preparation of N—((S)-1-((S)-2-carbamoylpyrrolidin-1-yl)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (74) Compound 74 was prepared according to the procedure described for the synthesis of compound 72 by replacing leucine amide with (S)-pyrrolidine-2-carboxamide. LCMS (+ESI) m/z=521.2 [M+H]+.

Example 48

Preparation of N—((S)-1-((R)-2-carbamoylpyrrolidin-1-yl)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (75) Compound 75 was prepared according to the procedure described for the synthesis of compound 72 by replacing leucine amide with (R)-pyrrolidine-2-carboxamide. LCMS (+ESI) m/z=521.5 [M+H]+.

Example 49

Preparation of N—((S)-3,3-dimethyl-1-((S)-2-(methylcarbamoyl)pyrrolidin-1-yl)-1-oxobutan-2-yl)-5-methyl-3-(2,4,5-trifluorophenyl)-4,5,6,7-tetrahydro-1H-pyrazolo[4,3-c]pyridine-1-carboxamide (76) Compound 76 was prepared according to the procedure described for the synthesis of compound 72 by replacing leucine amide with (S)—N-methylpyrrolidine-2-carboxamide. LCMS (+ESI) m/z=535.2 [M+H]+.

Example 50

Preparation of (S)-ethyl 4-(3,3-dimethyl-2-(5-methyl-3-(2,4,5-trifluorophenyl)-4,5,6,7-tetrahydro-1H-pyrazolo[4,3-c]pyridine-1-carboxamido) butanoyl)piperazine-1-carboxylate (77) Compound 77 was prepared according to the procedure described for the synthesis of compound 72 by replacing leucine amide with ethyl piperazine-1-carboxylate. LCMS (+ESI) m/z=565.4 [M+H]+.

Example 51

Preparation of N—((S)-1-(S)-3-hydroxypiperidin-1-yl)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (78) Compound 78 was prepared according to the procedure described for the synthesis of compound 72 by replacing leucine amide with (S)-3-hydroxyl-piperidine. LCMS (+ESI) m/z=508.3 [M+H]+.

Example 52

Preparation of (S)—N-(1-(4-carbamoylpiperidin-1-yl)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (79) Compound 79 was prepared according to the procedure described for the synthesis of compound 72 by replacing leucine amide with piperidine-4-carboxamide. LCMS (+ESI) m/z=535.4 [M+H]+.

Example 53

Preparation of (S)—N-(1-(3-hydroxypropylamino)-3,3-dimethyl-1-oxobutan-2-yl)-5-methyl-3-(2,4,5-trifluorophenyl)-4,5,6,7-tetrahydro-1H-pyrazolo[4,3-c]pyridine-1-carboxamide (80) Compound 80 was prepared according to the procedure described for the synthesis of compound 72 by replacing leucine amide with 3-amino-propan-1-ol. LCMS (+ESI) m/z=482.3 [M+H]+.

Example 54

Preparation of (S)-2-(3-(2,5-difluorophenyl)-5-methyl-4,5,6,7-tetrahydro-1H-pyrazolo[4,3-c]pyridine-1-carboxamido)-3,3-dimethylbutanoic acid (81) Compound 81 was prepared according to the procedure described for the synthesis of compound 71 by replacing 2,4,5-trifluorobenzoyl chloride with 2,5-difluorobenzoyl chloride in the synthesis of intermediate 19. LCMS (+ESI) m/z=407.2 [M+H]+.

Example 55

Preparation of (S)-2-(3-(2,5-difluorophenyl)-5-ethyl-4,5,6,7-tetrahydro-1H-pyrazolo[4,3-c]pyridine-1-carboxamido)-3,3-dimethylbutanoic acid (82) Compound 82 was prepared according to the procedure described for the synthesis of compound 81 by replacing formaldehyde with acetadehyde. LCMS (+ESI) m/z=421.2 [M+H]+.

Example 56

Preparation of (S)-ethyl 2-(1-(3,3-dimethyl-1-(methylamino)-1-oxobutan-2-ylcarbamoyl)-3-(2,4,5-trifluorophenyl)-6,7-dihydro-1H-pyrazolo[4,3-c]pyridin-5(4H)-yl)acetate (83)

Step 1: Preparation of (S)—N-(3,3-dimethyl-1-(methylamino)-1-oxobutan-2-yl)-3-(2,4,5-trifluorophenyl)-4,5,6,7-tetrahydro-1H-pyrazolo[4,3-c]pyridine-1-carboxamide (84) Intermediate 84 was prepared according to the procedure described for the synthesis of compound 37 by omitting the reductive amination step with formaldehyde. LCMS (+ESI) m/z=424 [M+H]+.

Step 2: A mixture of intermediate 84 (0.39 g), DIEA (0.35 mL) and ethyl bromoacetate (0.22 mL) in acetonitrile was heated at 60° C. for 1.5 h. After evaporation of MeCN, the residue was extracted between EtOAc and saturated sodium bicarbonate. The organic phase was dried over sodium sulfate and evaporated to dryness. The crude product was purified by column chromatography with 70% to 90% EtOAc/Hex to give compound 83 (0.27 g, 57%). LCMS (+ESI) m/z=510.3 [M+H]+.

Example 57

Preparation of (S)—N-(3,3-dimethyl-1-(methylamino)-1-oxobutan-2-yl)-5-(2-hydroxyethyl)-3-(2,4,5-trifluorophenyl)-4,5,6,7-tetrahydro-1H-pyrazolo[4,3-c]pyridine-1-carboxamide (85) To a suspension of LAH powder (8 mg) in THF was added a solution of compound 83 (45 mg) in THF at 0° C. under nitrogen. After stirring for 30 min, the reaction was quenched with brine and extracted with EtOAc. The combined organic phase was dried over sodium sulfate and evaporated to dryness. The residue was dissolved in MeOH and purified with a preparative LC-MS to give compound 85 (27 mg). LCMS (+ESI) m/z=468.3 [M+H]+.

Example 58

An alternative method to synthesize intermediate 23.

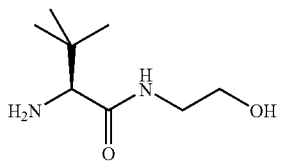

23

To a solution of Boc-tert-leucine (4.62 g, 20.0 mmol) and N-methyl-morpholine (25 mmol) in THF (50 mL) was added isobutyl chloroformate (2.8 mL, 21.3 mmol) at 0° C. After stifling for 20 min, ethanolamine (3.6 mL, 60.0 mmol) was added and stirred for 1 hr. THF was evaporated under vacuum and the residue was extracted between EtOAc and saturated sodium bicarbonate solution twice. The organic phase was dried over sodium sulfate and evaporated to dryness to give an oil intermediate, which was stirred in 4N HCl/dioxane for 0.5 hr. The reaction mixture was diluted with diethyl ether and filtered to collect the white precipitate of the HCl salt of intermediate 23. LCMS (+ESI) m/z=175 (M+H).

Example 59

Preparation of (S)-3-(5-chloro-2-fluorophenyl)-N-(1-(2-hydroxyethylamino)-3,3-dimethyl-1-oxobutan-2-yl)-6,7-dihydropyrano[4,3-c]pyrazole-1(4H)-carboxamide (86) Compound 86 was prepared according to the procedure for the synthesis of compound 36 by replacing 3,4-difluorobenzoyl chloride with 5-chloro-2-fluorobenzoyl chloride. LCMS (+ESI) m/z=453.3 [M+H]+. 1H NMR (CDCl3) δ 7.81 (d, J=9.1 Hz, 1H), 7.60-7.62 (dd, J=2.7, 6.21 Hz, 1H), 7.27-7.32 (m, 1H), 7.07 (t, J=9.3 Hz, 1H), 6.56 (br, 1H), 4.57 (s 2H), 4.12 (d, J=9.2 Hz, 1H), 3.87 (t, J=5.6 Hz, 2H), 3.66 (s, 3H), 3.36-3.41 (m, 2H), 3.08-3.12 (m, 2H), 1.03 (s, 9H). Purity: 97%.

Example 60

(S)-3-(2,5-difluorophenyl)-N-(1-(2-hydroxyethylamino)-3,3-dimethyl-1-oxobutan-2-yl)-6,7-dihydropyrano[4,3-c]pyrazole-1(4H)-carboxamide (87) Compound 87 was prepared according to the procedure for the synthesis of compound 36 by replacing 3,4-difluorobenzoyl chloride with 2,5-difluorobenzoyl chloride. LCMS (+ESI) m/z=437.4 [M+H]+. 1H NMR (CDCl3) δ 7.88 (d, J=9.0 Hz, 1H), 7.41-7.45 (m, 1H), 7.07-7.11 (m, 2H), 6.34 (br, 1H), 4.67 (s, 2H), 4.15 (d, J=9.0 Hz, 1H), 3.95 (t, J=5.6 Hz, 2H), 3.72-3.76 (m, 2H), 3.45-3.49 (m, 2H), 3.17 (br, 2H), 1.05 (s, 9H). Purity: 97%.

Example 61

Preparation of (S)-3-(4-chloro-2-fluorophenyl)-N-(1-(2-hydroxyethylamino)-3,3-dimethyl-1-oxobutan-2-yl)-6,7-dihydropyrano[4,3-c]pyrazole-1(4H)-carboxamide (88) Compound 88 was prepared according to the procedure for the synthesis of compound 36 by replacing 3,4-difluorobenzoyl chloride with 4-chloro-2-fluorobenzoyl chloride. LCMS (+ESI) m/z=453.3 [M+H]+. 1H NMR (CDCl3) δ 7.90 (d, J=9.0 Hz, 1H), 7.67 (t, J=8.1 Hz, 1H), 7.16-7.24 (m, 2H), 6.45 (br, 1H), 4.65 (s, 2H), 4.18 (d, J=9.1 Hz, 1H), 3.94 (t, J=5.6 Hz, 2H), 3.73 (br, 2H), 3.45 (br, 2H), 3.17 (br, 2H), 1.10 (s, 9H). Purity: 98%.

Example 63

Preparation of tert-butyl 3-(2,4,5-trifluorophenyl)-6,7-dihydro-1H-pyrazolo[4,3-b]pyridine-4(5H)-carboxylate (intermediate 20) and tert-butyl 3-(2,4,5-trifluorophenyl)-4,5-dihydro-1H-pyrazolo[3,4-c]pyridine-6(7H)-carboxylate (intermediate 21)

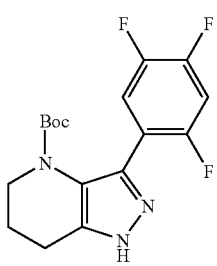

20

21

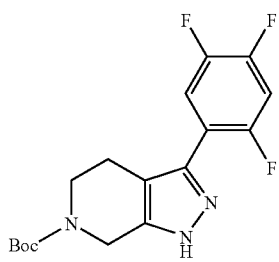

To a solution of 3-N(Boc)-piperidone (615 mg, 3.1 mmol) in THF (8 mL) was add LHMDS (1.0 M in THF, 3.1 mL) at 0° C. After stirring for 5 min, 2,4,5-trifluorobenzoyl chloride was added and stirred for additional 5 min. Acetic acid (1 mL) was added followed by addition of hydrazine monohydrate (1 mL). The reaction was stirred for 10 min and evaporated under vacuum. The crude mixture was extracted between EtOAc and aqueous sodium bicarbonate. The organic phase was dried over sodium sulfate and evaporated to dryness. The crude product was purified with 20% to 60% EtOAc/Hex to give intermediate 20 (slow eluting component, 0.32 g) and intermediate 21 (fast eluting component, 0.18 g). LCMS (+ESI) m/z=354 [M+H]⁺.

Example 64

Preparation of tert-butyl 3-(3,4,-difluorophenyl)-6,7-dihydro-1H-pyrazolo[4,3-b]pyridine-4(5H)-carboxylate (intermediate 20B) and tert-butyl 3-(3,4,-difluorophenyl)-4,5-dihydro-1H-pyrazolo[3,4-c]pyridine-6(7H)-carboxylate (intermediate 21B)

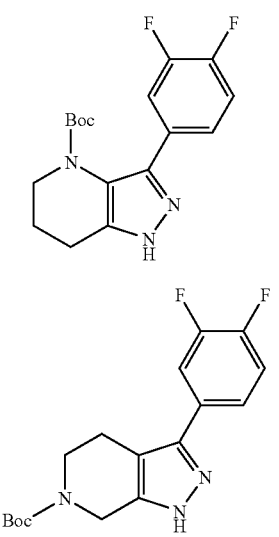

Intermediates 20B and 21B were prepared according to the procedure for the synthesis of intermediates 20 and 21 by replacing 2,4,5-trifluorobenzoyl chloride with 3,4-difluorobenzoyl chloride. LCMS (+ESI) m/z=336 [M+H]⁺.

Example 65

Preparation of tert-butyl 3-(2,5,-difluorophenyl)-6,7-dihydro-1H-pyrazolo[4,3-b]pyridine-4(5H)-carboxylate (intermediate 20C) and tert-butyl 3-(2,5,-difluorophenyl)-4,5-dihydro-1H-pyrazolo[3,4-c]pyridine-6(7H)-carboxylate (intermediate 21C)

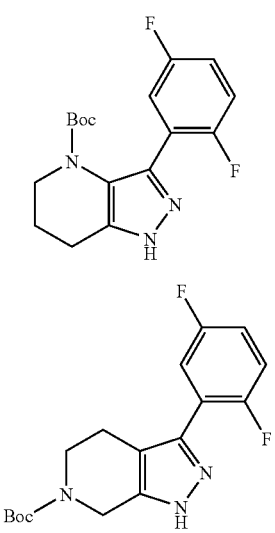

Intermediates 20C and 21C were prepared according to the procedure for the synthesis of intermediates 20 and 21 by replacing 2,4,5-trifluorobenzoyl chloride with 2,5-difluorobenzoyl chloride. LCMS (+ESI) m/z=336 [M+H]⁺.

Example 66

Preparation of tert-butyl 3-(5-chloro-2-fluorophenyl)-6,7-dihydro-1H-pyrazolo[4,3-b]pyridine-4(5H)-carboxylate (intermediate 20D).

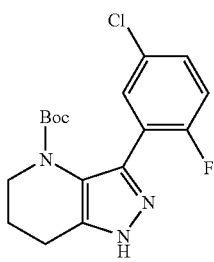

Intermediates 20D was prepared according to the procedure for the synthesis of intermediates 20 and 21 by replacing 2,4,5-trifluorobenzoyl chloride with 5-chloro-2-fluorobenzoyl chloride. LCMS (+ESI) m/z=352 [M+H]⁺.

Example 67

Preparation of (S)—N-(1-(2-hydroxyethylamino)-3,3-dimethyl-1-oxobutan-2-yl)-6-methyl-3-(2,4,5-trifluorophenyl)-4,5,6,7-tetrahydro-1H-pyrazolo[3,4-c]pyridine-1-carboxamide (89) Compound 89 was prepared according to the procedure for the synthesis of compound 37 by replacing intermediate 19 with intermediate 21, and replacing tert-leucine methylamide with intermediate 23. LCMS (+ESI) m/z=468.4 [M+H]⁺. ¹H NMR (CDCl₃) δ 7.84 (d, J=9.1 Hz, 1H), 7.46-7.53 (m, 1H), 6.98-7.05 (m, 1H), 6.73 (br, 1H) 4.18

(d, J=9.1 Hz, 1H), 3.99 (br, 2H), 3.68 (br, 2H), 3.42 (br, 2H), 2.67-2.73 (m, 4H), 2.51 (s, 3H), 1.06 (s, 9H). Purity: 89%.

Example 68

Preparation of (S)-3-(3,4-difluorophenyl)-N-(1-(2-hydroxyethylamino)-3,3-dimethyl-1-oxobutan-2-yl)-6-methyl-4,5,6,7-tetrahydro-1H-pyrazolo[3,4-c]pyridine-1-carboxamide (90) Compound 90 was prepared according to the procedure for the synthesis of compound 37 by replacing intermediate 19 with intermediate 21B, and replacing tert-leucine methylamide with intermediate 23. LCMS (+ESI) m/z=450.4 [M+H]$^+$. $^1$H NMR (CDCl$_3$) δ 7.88 (d, J=9.1 Hz, 1H), 7.58-7.63 (m, 1H), 7.49-7.52 (m, 1H), 7.22 (q, J=8.9 Hz, 1H), 6.65 (br, 1H) 4.18 (d, J=9.2 Hz, 1H), 3.88 (m, 2H), 3.69 (br, 2H), 3.42-3.46 (m, 2H), 2.81 (br, 2H), 2.68-2.77 (m, 2H), 2.49 (s, 3H), 1.06 (s, 9H). Purity: 97%.

Example 69

Preparation of (S)-3-(3,4-difluorophenyl)-N-(1-(2-hydroxyethylamino)-3,3-dimethyl-1-oxobutan-2-yl)-4-methyl-4,5,6,7-tetrahydro-1H-pyrazolo[4,3-b]pyridine-1-carboxamide (91) Compound 91 was prepared according to the procedure for the synthesis of compound 37 by replacing intermediate 19 with intermediate 20B, and replacing tert-leucine methylamide with intermediate 23. LCMS (+ESI) m/z=450.4 [M+H]$^+$. $^1$H NMR (CDCl$_3$) δ 7.81-7.84 (m, 2H), 7.71-7.75 (m, 1H), 7.17-7.124 (m, 1H), 6.58 (br, 1H), 4.14 (d, J=8.9 Hz, 1H), 3.72 (br, 2H), 3.42-3.47 (m, 2H), 3.00-3.07 (m, 4H), 2.51 (s, 3H), 1.80-1.86 (m, 2H), 1.05 (s, 9H). Purity: 98%.

Example 70

Preparation of (S)-3-(2,5-difluorophenyl)-N-(1-(2-hydroxyethylamino)-3,3-dimethyl-1-oxobutan-2-yl)-4-methyl-4,5,6,7-tetrahydro-1H-pyrazolo[4,3-b]pyridine-1-carboxamide (92) Compound 92 was prepared according to the procedure for the synthesis of compound 37 by replacing intermediate 19 with intermediate 20C, and replacing tert-leucine methylamide with intermediate 23. LCMS (+ESI) m/z=450.4 [M+H]$^+$. $^1$H NMR (CDCl$_3$) δ 7.80 (d, J=8.9 Hz, 1H), 7.37-7.42 (m, 1H), 7.06-7.12 (m, 2H), 6.63 (br, 1H) 4.14 (d, J=8.9 Hz, 1H), 3.71 (br, 2H), 3.41-3.45 (m, 2H), 3.02-3.06 (m, 2H), 2.96 (br, 2H), 2.42 (s, 3H), 1.92 (br, 2H), 1.05 (s, 9H). Purity: 98%.

Example 71

Preparation of (S)-3-(2,5-difluorophenyl)-N-(1-(2-hydroxyethylamino)-3,3-dimethyl-1-oxobutan-2-yl)-6-methyl-4,5,6,7-tetrahydro-1H-pyrazolo[3,4-c]pyridine-1-carboxamide (93) Compound 93 was prepared according to the procedure for the synthesis of compound 37 by replacing intermediate 19 with intermediate 21C, and replacing tert-leucine methylamide with intermediate 23. LCMS (+ESI) m/z=450.4 [M+H]$^+$. $^1$H NMR (CDCl$_3$) δ 7.86 (d, J=9.0 Hz, 1H), 7.33-7.37 (m, 1H), 7.06-7.12 (m, 2H), 6.61 (m, 1H), 4.17 (d, J=9.0 Hz, 1H), 3.88-3.99 (m, 2H), 3.68-3.71 (m, 2H), 3.41-3.45 (m, 2H), 2.68 (br, 4H), 2.52 (s, 3H), 1.06 (s, 9H). Purity: 98%.

Example 72

Preparation of (S)-3-(5-chloro-2-fluorophenyl)-N-(1-(2-hydroxyethylamino)-3,3-dimethyl-1-oxobutan-2-yl)-4-methyl-4,5,6,7-tetrahydro-1H-pyrazolo[4,3-b]pyridine-1-carboxamide (94) Compound 94 was prepared according to the procedure for the synthesis of compound 37 by replacing intermediate 19 with intermediate 20D, and replacing tert-leucine methylamide with intermediate 23. LCMS (+ESI) m/z=466.3 [M+H]$^+$. $^1$H NMR (CDCl$_3$) δ 7.80 (d, J=8.9 Hz, 1H), 7.62-7.65 (m, 1H), 7.32-7.37 (m, 1H), 7.10 (t, J=9.0 Hz, 1H), 4.14 (d, J=8.9 Hz, 1H), 3.71 (br, 2H), 3.42-3.46 (m, 2H), 3.02-3.06 (m, 2H), 2.96 (br, 2H), 2.41 (s, 3H), 1.92 (br, 2H), 1.06 (s, 9H). Purity: 99%.

Example 73

Preparation of 3-(3,4-difluorophenyl)-1,4,5,7-tetrahydropyrano[3,4-c]pyrazole (16B).

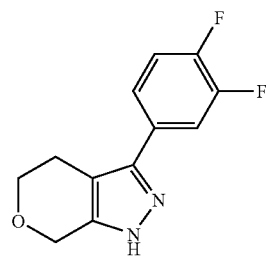

16B

Intermediate 16B was prepared according to the procedure for the synthesis of intermediate 15 by replacing 1-Boc-4-piperidone with dihydro-2H-pyran-3(4H)-one LCMS (+ESI) m/z=236 [M+H]$^+$. $^1$H NMR (CDCl$_3$) δ 7.37-7.41 (m, 1H), 7.29-7.32 (m, 1H) 7.17-7.24 (m, 1H), 4.76 (s, 2H), 3.95 (t, J=5.5 Hz, 2H), 2.84 (t, J=5.5 Hz, 2H).

Example 74

Preparation of 3-(5-chloro-2-fluorophenyl)-1,4,5,7-tetrahydropyrano[3,4-c]pyrazole (16C).

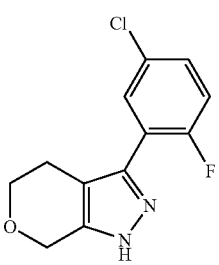

16C

Intermediate 16C was prepared according to the procedure for the synthesis of intermediate 15 by replacing 1-Boc-4-piperidone with dihydro-2H-pyran-3(4H)-one, and replacing 3,4-difluorobenzoyl chloride with 5-chloro-2-fluorobenzoyl chloride. LCMS (+ESI) m/z=253 [M+H]$^+$.

Example 75

Preparation of 3-(2,4,5-trifluorophenyl)-1,4,5,7-tetrahydropyrano[3,4-c]pyrazole (16D).

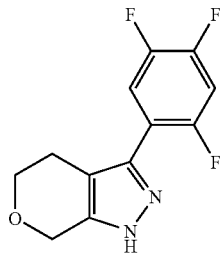

Intermediate 16D was prepared according to the procedure for the synthesis of intermediate 15 by replacing 1-Boc-4-piperidone with dihydro-2H-pyran-3(4H)-one, and replacing 3,4-difluorobenzoyl chloride with 2,4,5-trifluorobenzoyl chloride. LCMS (+ESI) m/z=255 [M+H]$^+$.

Example 76

Preparation of (S)-3-(3,4-difluorophenyl)-N-(1-(2-hydroxyethylamino)-3,3-dimethyl-1-oxobutan-2-yl)-4,5-dihydropyrano[3,4-c]pyrazole-1(7H)-carboxamide (95) Compound 95 was prepared according to the procedure for the synthesis of compound 28 by replacing intermediate 16 with intermediate 16B, and replacing tert-leucine methylamide with intermediate 23. LCMS (+ESI) m/z=437.4 [M+H]$^+$. $^1$H NMR (CDCl$_3$) δ 7.84 (d, J=9.2 Hz, 1H), 7.59-7.64 (m, 1H), 7.50 (br, 1H), 7.22 (q, J=9.0 Hz, 1H), 4.99 (d, J=8.1 Hz, 2H), 4.20 (d, J=9.3 Hz, 1H), 3.85-3.94 (m, 2H), 3.72 (s, 2H), 3.43 (m, 2H), 2.80 (br, 2H), 1.06 (s, 9H). Purity: 96%.

Example 77

Preparation of (S)-3-(5-chloro-2-fluorophenyl)-N-(1-(2-hydroxyethylamino)-3,3-dimethyl-1-oxobutan-2-yl)-4,5-dihydropyrano[3,4-c]pyrazole-1(7H)-carboxamide (96) Compound 96 was prepared according to the procedure for the synthesis of compound 28 by replacing intermediate 16 with intermediate 16C, and replacing tert-leucine methylamide with intermediate 23. LCMS (+ESI) m/z=453.3 [M+H]$^+$. $^1$H NMR (CDCl$_3$) δ 7.82 (d, J=9.3 Hz, 1H), 7.61-7.63 (m, 1H), 7.32-7.36 (m, 1H) 7.09 (t, J=9.2 Hz, 1H), 4.99 (d, J=8.0 Hz, 2H), 4.19 (d, J=9.3 Hz, 1H), 3.78-3.88 (m, 2H), 3.69 (s, 2H), 3.43 (m, 2H), 2.63 (br, 2H), 1.06 (s, 9H). Purity: 91%.

Example 78

Preparation of (S)—N-(1-(2-hydroxyethylamino)-3,3-dimethyl-1-oxobutan-2-yl)-3-(2,4,5-trifluorophenyl)-4,5-dihydropyrano[3,4-c]pyrazole-1(7H)-carboxamide (97) Compound 97 was prepared according to the procedure for the synthesis of compound 28 by replacing intermediate 16 with intermediate 16D, and replacing tert-leucine methylamide with intermediate 23. LCMS (+ESI) m/z=453.3 [M+H]$^+$. $^1$H NMR (CDCl$_3$) δ 7.81 (d, J=9.1 Hz, 1H), 7.51-7.54 (m, 1H), 7.02-7.05 (m, 1H), 6.37 (br, 1H), 5.03 (d, J=8.9 Hz, 2H), 4.14 (d, J=9.2 Hz, 1H), 3.83-3.90 (m, 2H), 3.74 (br, 2H), 3.45 (br, 2H), 3.35 (br, 1H), 2.64 (br, 1H), 1.06 (s, 9H). Purity: 97%.

Example 79

Preparation of (S)-3-(3,4-difluorophenyl)-N-(1-(2-hydroxyethylamino)-3,3-dimethyl-1-oxobutan-2-yl)-5-methyl-4,5,6,7-tetrahydro-1H-pyrazolo[4,3-c]pyridine-1-carboxamide (98) Compound 98 was prepared according to the procedure for the synthesis of compound 37 by replacing intermediate 19 with intermediate 15, and replacing tert-leucine methylamide with intermediate 23. LCMS (+ESI) m/z=450.3 [M+H]$^+$. $^1$H NMR (CDCl$_3$) δ 7.89 (d, J=9.1 Hz, 1H), 7.52 (t, J=4 Hz, 1H), 7.40 (br, 1H), 7.23 (q, J=8.9 Hz, 1H), 4.20 (d, J=9.1 Hz, 1H), 3.69 (s, 2H), 3.56 (s, 2H), 3.42 (s, 2H), 3.16 (s, 2H), 2.74 (t, J=5.5 Hz, 2H), 2.52 (s, 3H), 1.06 (s, 9H). Purity: 96%.

Example 80

Preparation of (S)—N-(1-amino-3,3-dimethyl-1-oxobutan-2-yl)-3-(3,4-difluorophenyl)-6,7-dihydropyrano[4,3-c]pyrazole-1(4H)-carboxamide (99) Compound 99 was prepared according to the procedure for the synthesis of compound 28 by replacing tert-leucine methylamide with tert-leucine amide. LCMS (+ESI) m/z=393.3 [M+H]$^+$. $^1$H NMR (CDCl$_3$) δ 7.80 (d, J=9.3 Hz, 1H), 7.36-7.42 (m 1H), 7.10-7.22 (m, 2H), 4.73 (s, 2H), 4.19 (d, J=9.3 Hz, 1H) 3.85 (t, J=5.6 Hz, 2H), 3.06 (m, 2H), 1.06 (s, 9H). Purity: 99%.

Example 81

Preparation of (S)-ethyl 2-(3-(3,4-difluorophenyl)-1-(3,3-dimethyl-1-(methylamino)-1-oxobutan-2-ylcarbamoyl)-6,7-dihydro-1H-pyrazolo[4,3-b]pyridin-4(5H)-yl)acetate (100) Compound 100 was prepared according to the procedure for the synthesis of compound 83 by replacing intermediate 19 with intermediate 20B. LCMS (+ESI) m/z=492.5 [M+H]$^+$.

Example 82

Preparation of (S)-3-(3,4-difluorophenyl)-N-(3,3-dimethyl-1-(methylamino)-1-oxobutan-2-yl)-4-(2-hydroxyethyl)-4,5,6,7-tetrahydro-1H-pyrazolo[4,3-b]pyridine-1-carboxamide (101) Compound 101 was prepared according to the procedure for the synthesis of compound 85. LCMS (+ESI) m/z=450.4 [M+H]$^+$. $^1$H NMR (CDCl$_3$) δ 7.85 (d, J=9.5 Hz, 1H), 7.77-7.82 (m 1H), 7.66-7.70 (m, 1H), 7.16-7.23 (m, 1H), 4.16 (d, J=9.5 Hz, 1H), 3.73 (t, J=5.9 Hz, 2H), 3.13-3.15 (m, 2H), 3.02-3.06 (m, 2H), 2.82-2.85 (m, 5H), 1.78-1.83 (m, 2H), 1.08 (s, 9H). Purity: 92%.

The following compounds having the structure of formula I of the present invention can be synthesized by the methods disclosed herein as will be readily appreciated by those of skill in the art.

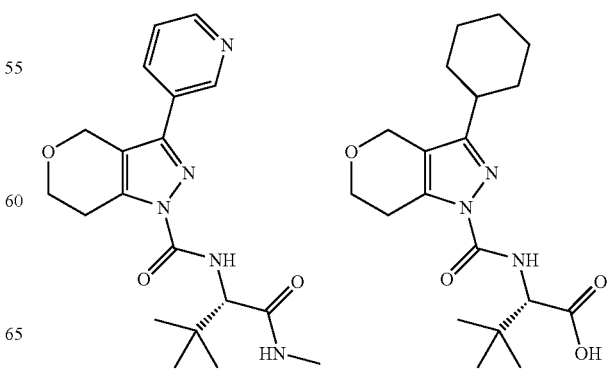

-continued
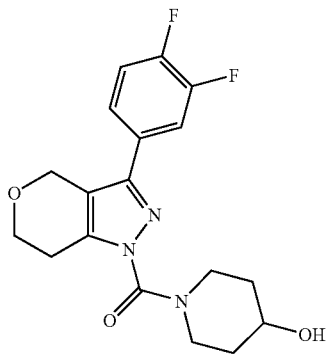
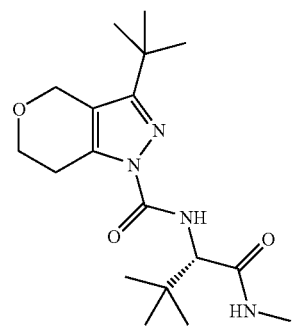
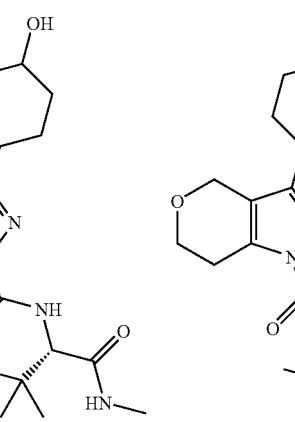
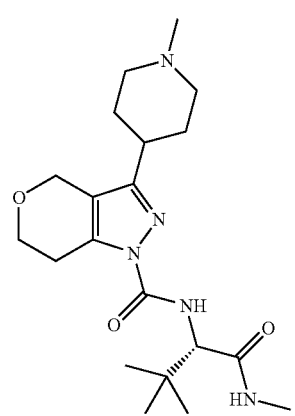
-continued
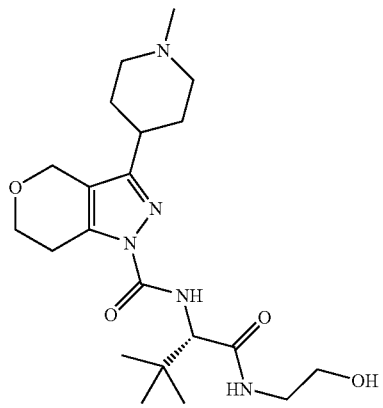
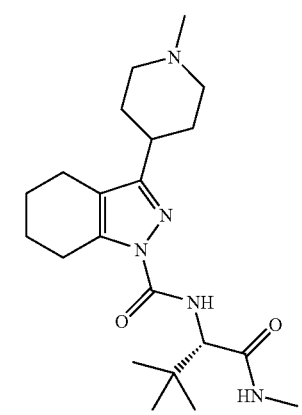
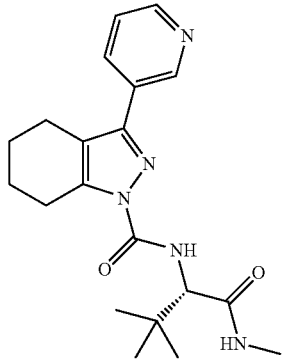
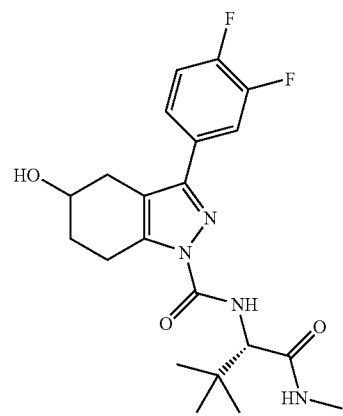

-continued
65
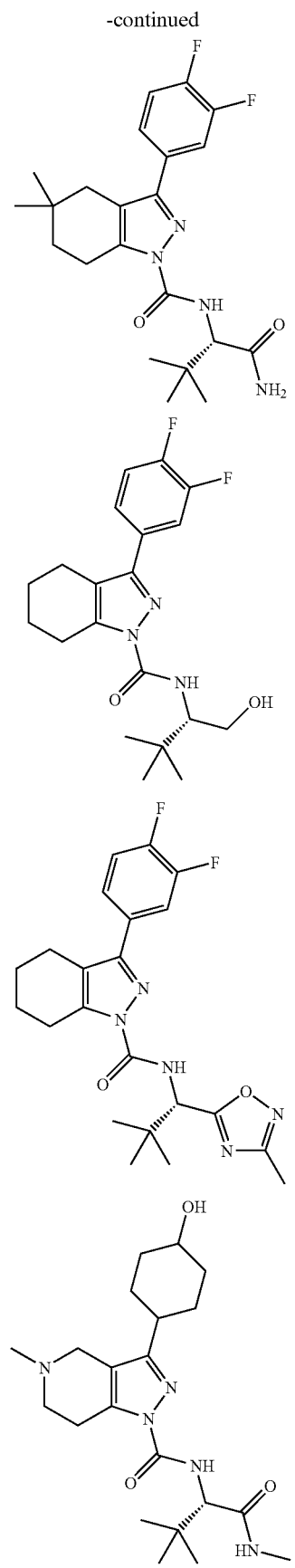
66
-continued
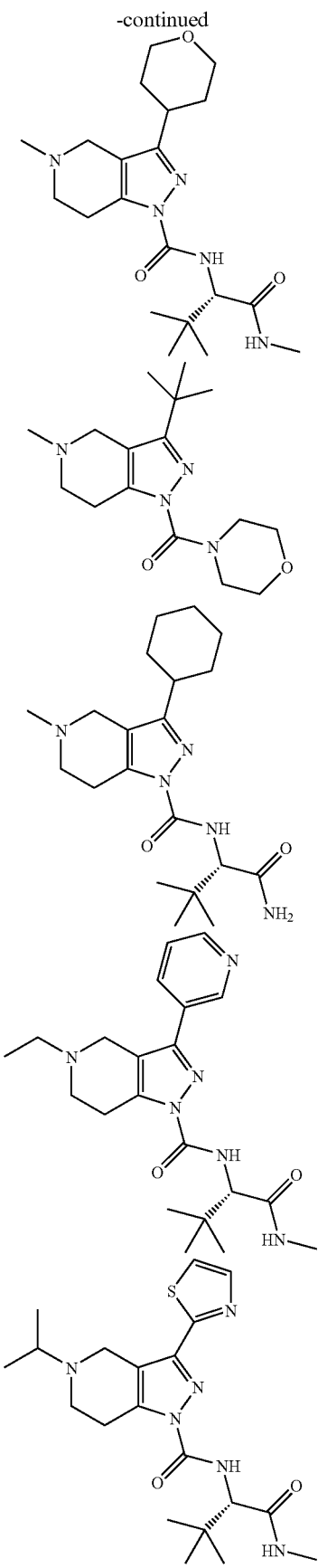

-continued
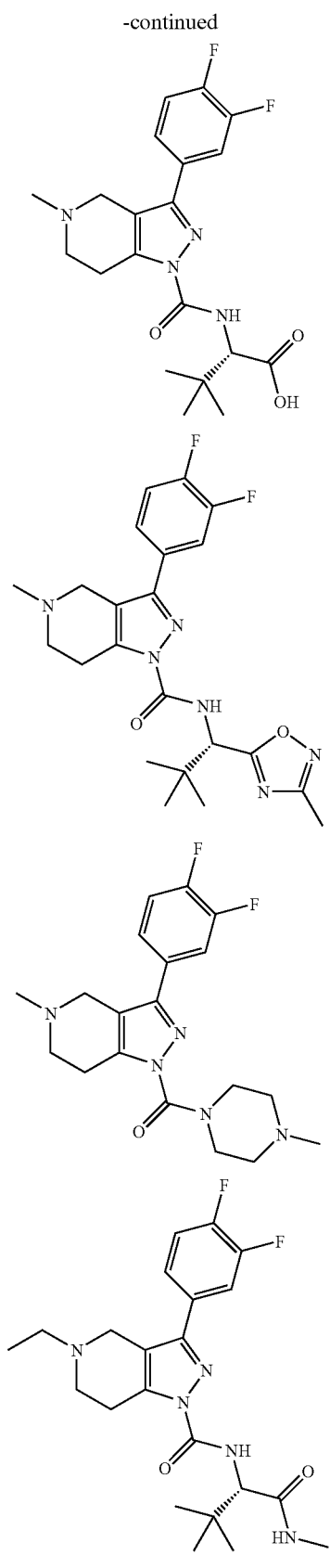
-continued
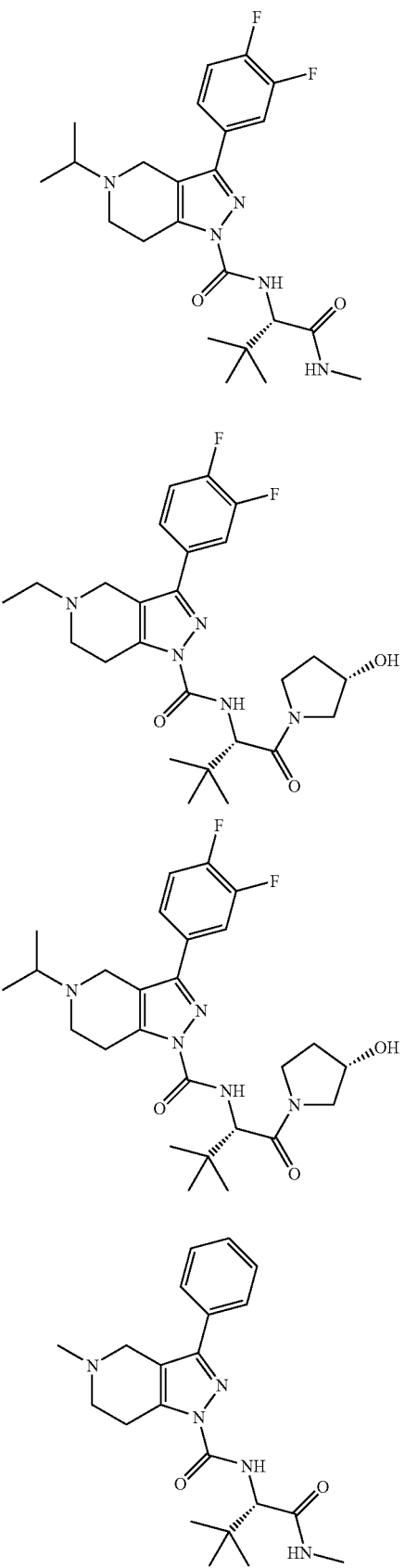

-continued
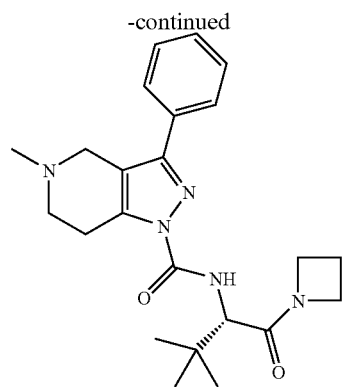
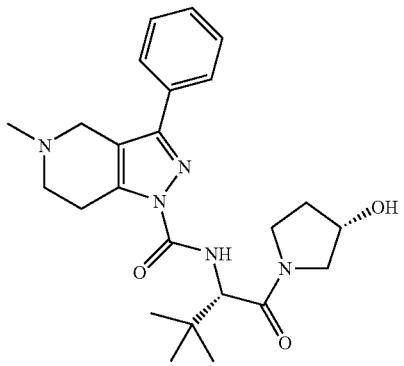
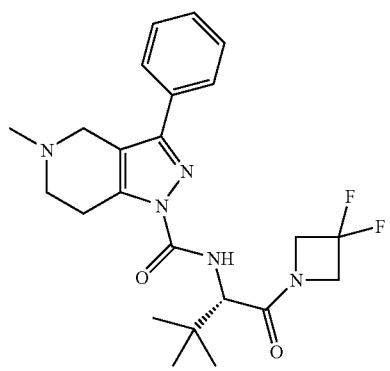
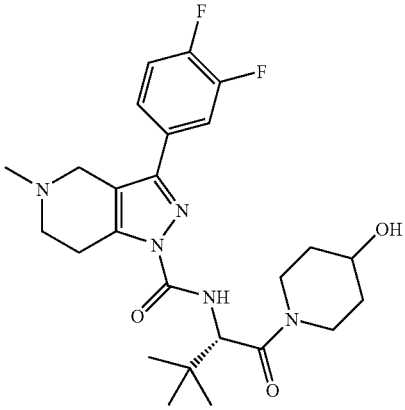
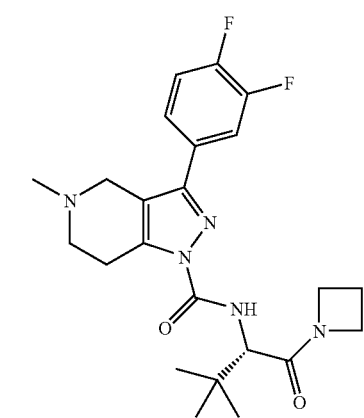
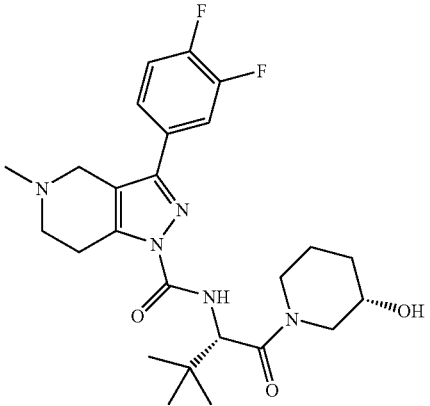
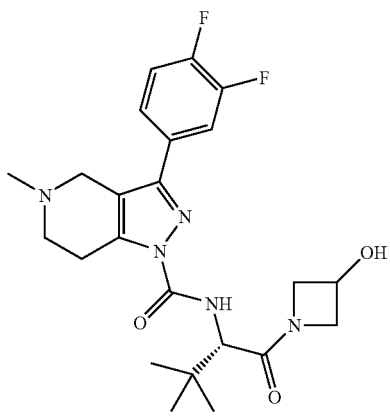
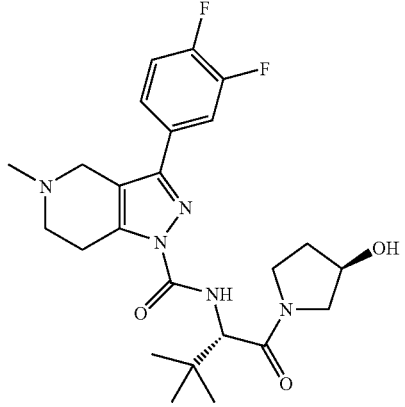

71
-continued
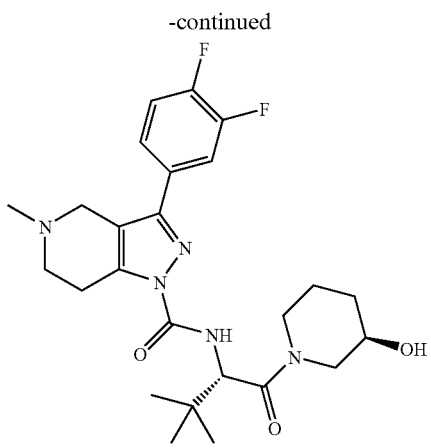
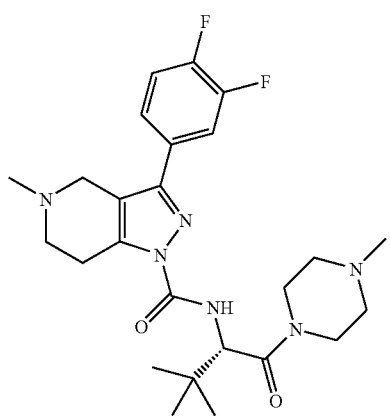
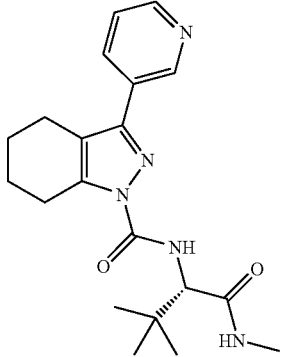
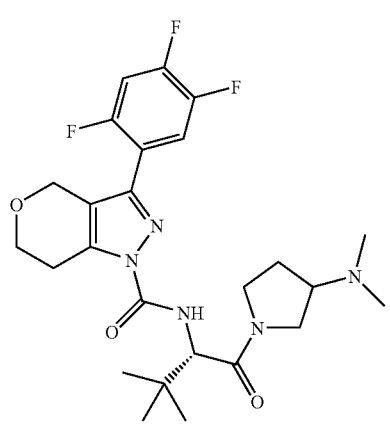
72
-continued
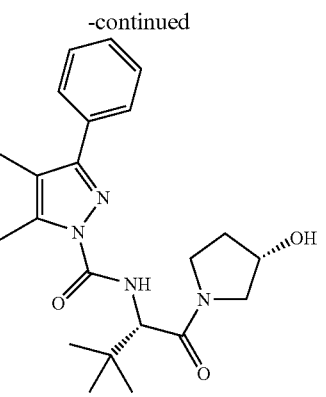
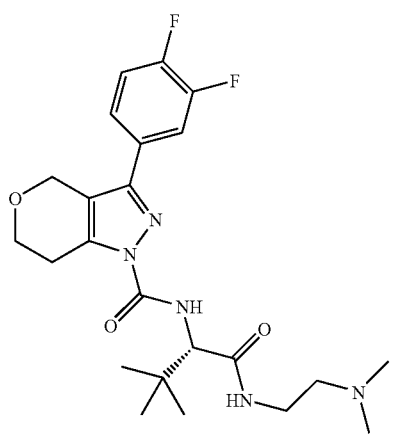
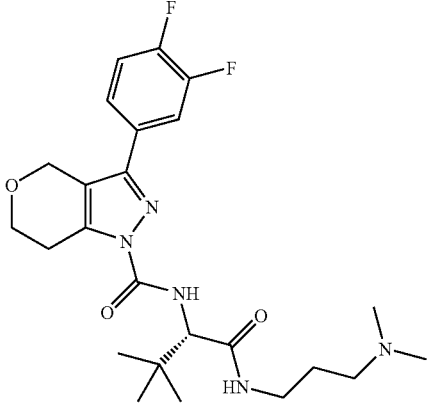
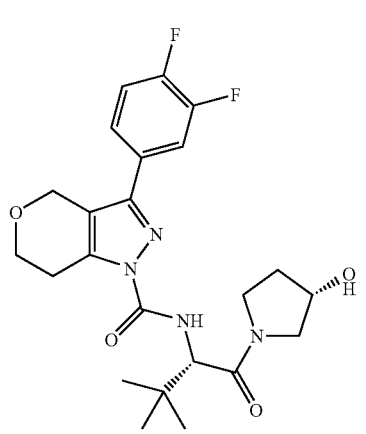

73
-continued
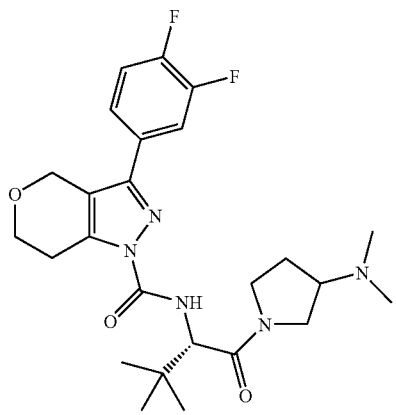
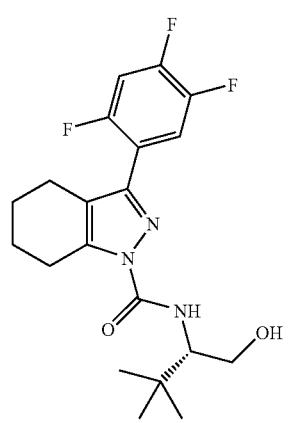
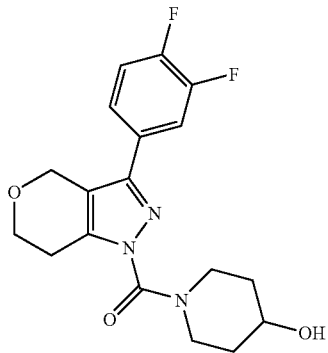
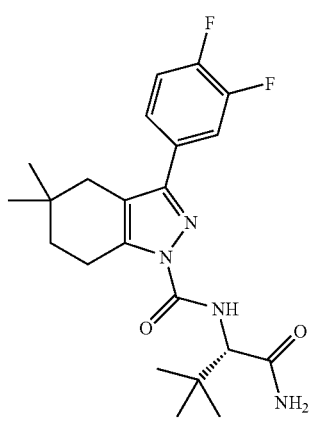
74
-continued
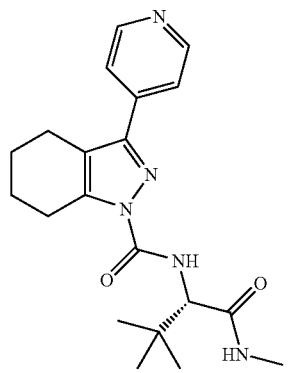
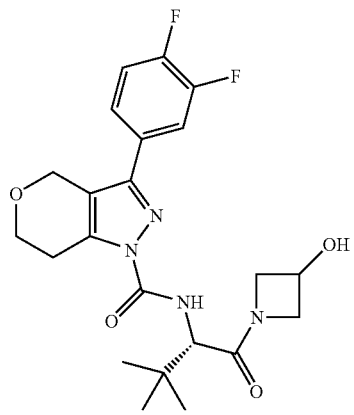
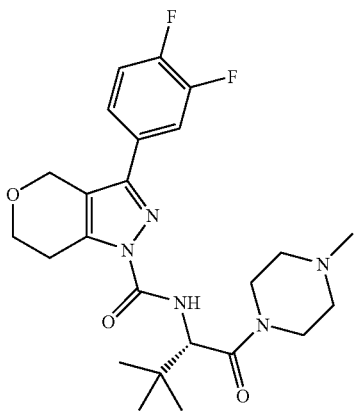
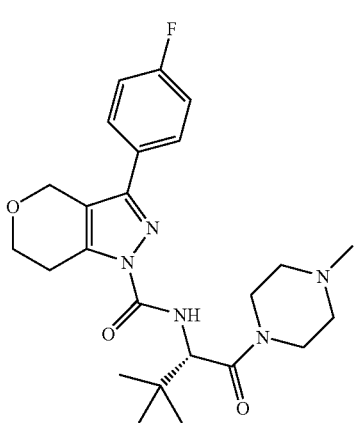

-continued
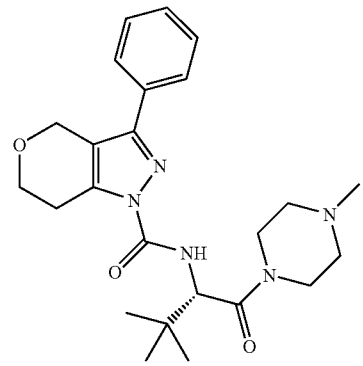
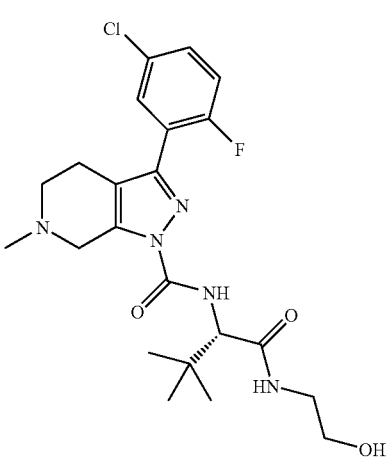
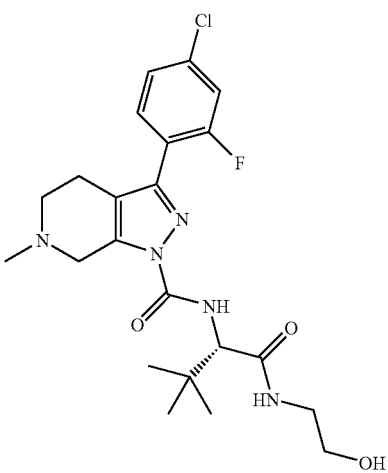
-continued
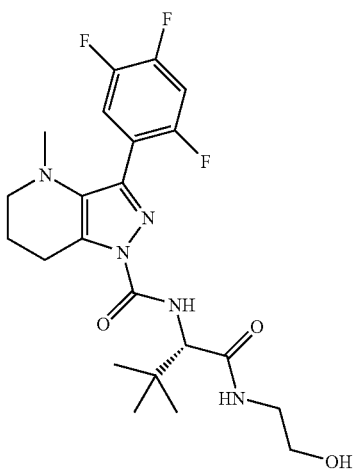
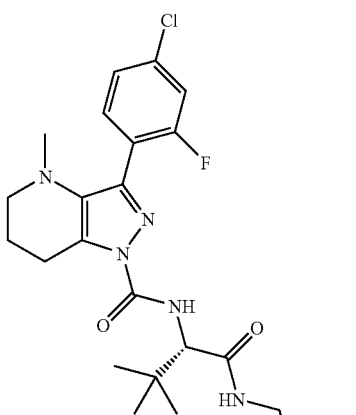
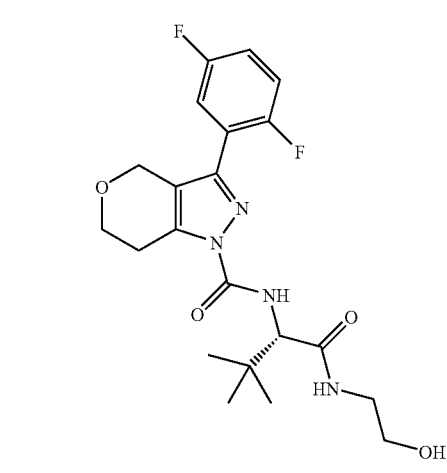

-continued

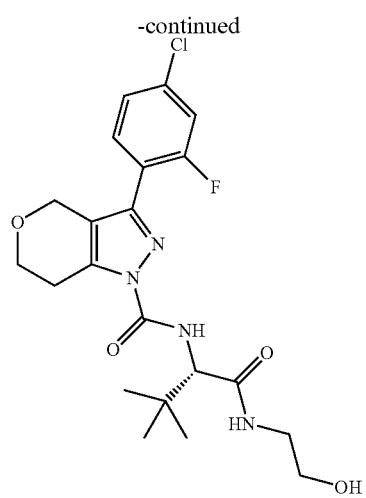

Example 83

Screening Methods

The ability of each of the compounds to act as agonists or inverse agonists at human CB2 and CB1 receptors (hCB2, hCB1, respectively) and at the rat CB2 receptor (rCB2) was determined by measuring changes in intracellular cyclic AMP (cAMP) levels as described in U.S. Pat. No. 7,517,874.

TR-FRET was measured using a 330-380 nm excitation filter, 615 nm and 665 nm emission filters, dichroic minor 380 nm and Z=10 mm. cAMP concentrations in each well were back-calculated from a cAMP standard curve run concurrently during each assay. Each plate contained 16 wells of forskolin stimulated cells and 16 wells of forskolin plus 1 µM CP55,940-treated cells. Concentrations of cAMP were expressed as a percent of the difference of these two groups of wells. Concentration-response data including $EC_{50}$ (the concentration of compound producing 50% of the maximal response) and intrinsic activity (the percent maximal activation compared to full activation by CP55, 940) were determined using a four-parameter non-linear regression algorithm (CambridgeSoft Bioassay).

The $EC_{50}$ values for compounds 71, 81 and 82 at the hCB1 and hCB2 receptors were above the maximum measurable range for the assay employed (30 µM). With these three exceptions, each of the compounds, 28-101 were determined to be agonists or inverse agonists at either the hCB1 or the hCB2 receptor. See Table I.

TABLE I

Potency at Human CB1 and CB2 determined by cAMP Assay

| POTENCY | EC50 > 1 µM | EC50 < 1 µM |
|---|---|---|
| hCB1R | 44, 45, 48, 57, 71, 72, 81, 82 | 28, 29, 30, 31, 32, 33, 34, 35, 36, 37, 38, 39, 40, 41, 42, 43, 46, 47, 49, 50, 51, 52, 53, 54, 55, 56, 58, 59, 60, 61, 62, 63, 64, 65, 66, 67, 68, 69, 70, 73, 74, 75, 76, 77, 78, 79, 80, 83, 84, 85, 86, 87, 88, 89, 90, 91, 92, 93, 94, 95, 96, 97, 98, 99, 100, 101 |
| hCB2R | 41, 43, 45, 46, 47, 58, 64, 66, 70, 71, 72, 73, 74, 75, 76, 77, 78, 79, 80, 81, 82, 83, 90, 99 | 28, 29, 30, 31, 32, 33, 34, 35, 36, 37, 38, 39, 40, 42, 44, 48, 49, 50, 51, 52, 53, 54, 55, 56, 57, 59, 60, 61, 62, 63, 65, 67, 68, 69, 84, 85, 86, 87, 88, 89, 91, 92, 93, 94, 95, 96, 97, 98, 100, 101 |

Example 84

Anti-Hyperalgesia in an Inflammatory Pain Model

The anti-hyperalgesic effects of test compounds in the Complete Freund's Adjuvant (CFA) model of inflammatory pain were determined essentially as described in U.S. Pat. No. 7,517,874 using male Sprague-Dawley rats (Hsd: Sprague-Dawley®SD®, Harlan, Indianapolis, Ind.) weighing 200-300 grams.

Test compounds were prepared in a Cremaphor vehicle mixture of 1:1:18 CremophorEL:ethanol:water. Cremophor was obtained from Sigma Chemical (St. Louis, Mo.). The vehicle mixture or vehicle mixture plus test compound were each administered orally.

Assessment of thermal hyperalgesia: Baseline and post-treatment paw withdrawal latencies to a noxious thermal stimulus were measured using a plantar test apparatus (Ugo Basile; obtained from Stoelting, Wood Dale, Ill.). This apparatus generates an infrared heat source that is linearly increasing in intensity. To avoid tissue damage, the power to the heat source was cut off after 20 seconds.

Paw withdrawal latency is defined as the time required for the rat to flick its paw away from the thermal stimulus. Ibuprofen (100 mg/kg, p.o.) was used as the positive control. Paw withdrawal latencies (in seconds) were measured before (naïve paw latency, L1) and 24 hr following (CFA-inflamed paw latency, L2) a single intraplantar injection of 0.1 mL CFA (Sigma-Aldrich, cat F5881, *Mycobacterium tuberculosis* 1 mg/ml).

Test compounds were administered orally 23 hours following CFA injection; i.e., 1 hour prior to thermal assessment (compound treated CFA-inflamed paw latency, L3). The mean paw withdrawal latency and standard error of the mean (SEM) was determined for the injured paws for each treatment group. See Table II below.

Data were expressed as percent maximum permissible effect (% MPE) defined as the percentage of restoration of latency of test compound-treated CFA inflamed paw as compared to the naïve paw latency.

$$\%MPE = -\frac{(L3-L2)}{(L1-L2)} \times 100$$

TABLE II

Paw withdrawal latency after CFA injection

| COMPOUND | PO Dose (mg/kg) | % MPE (1 hr) |
|---|---|---|
| 36 | 3 | 44 |
| 86 | 3 | 27 |
| 87 | 3 | 50 |
| 88 | 3 | 47 |
| 89 | 3 | 52 |
| 90 | 3 | 25 |
| 91 | 3 | 47 |
| 92 | 3 | 23 |
| 93 | 3 | 28 |
| 94 | 3 | 27 |
| 95 | 3 | 41 |
| 96 | 3 | 52 |
| 98 | 3 | 36 |
| 99 | 3 | 68 |
| 101 | 3 | 28 |

Example 85

Inhibition of Acetic Acid-Induced Writhing in Mice

This test identifies compounds which exhibit analgesic activity against visceral pain or pain associated with activation of low pH-sensitive nociceptors [see Barber and Gottschlich (1986) Med. Res. Rev. 12: 525-562; Ramabadran and Bansinath (1986) Pharm. Res. 3: 263-270]. Intraperitoneal administration of dilute acetic acid solution causes a writhing behavior in mice. A writhe is defined as a contraction of the abdominal muscles accompanied by an extension of the forelimbs and elongation of the body. The number of writhes observed in the presence and absence of test compounds is counted to determine the analgesic activity of the compounds.

Male ICR mice, 20-40 grams in weight, were weighed and placed in individual observation chambers (usually a 4 L beaker) with a fine layer of rodent bedding at the bottom. To determine the activity and potency of test compounds, different doses of the compound solution or vehicle were injected subcutaneously in the back of the neck 30 minutes prior to administration of acetic acid solution. After administration of the compound or vehicle control, mice were returned to their individual observation chambers awaiting the intraperitoneal administration of acetic acid solution.

Thirty minutes later, 10 ml/kg of a 0.6% (v/v) acetic acid solution was then injected into the right lower quadrant of the abdomen. Immediately after the injection, the mouse was returned to its observation chamber and the recording of the number of writhes is begun immediately. The number of writhes was counted over a 15-min period starting from the time of acetic acid injection. Raw data were analyzed using a one-way ANOVA followed by Dunnett's post-tests.

For dose-response analysis, raw data were converted to % maximum possible effect (% MPE) using the formula: % MPE=((Wc−Wv)/(0−Wv))*100, where Wc is the number of writhes in compound-treated mice and Wv is the mean number of writhes in vehicle-treated mice. The dose which elicited 50% attenuation of hypersensitivity (ED50) can be determined using linear regression analysis. (Tallarida & Murray, 1987).

Compounds 28, 31-33, 35 and 37 administered at a dose of 10 mg/kg each gave 100% reversal of the mechanical hyperalgesia induced by the acetic acid treatment.

Example 86

Carrageenan Model of Acute Inflammation

Acute inflammation is produced in rats by injecting 0.1 mL of 2% λ-carrageenan (type IV; Sigma, St. Louis, Mo.) into one hind paw. At various time points following carrageenan injection, paw volume measurements are taken for both hind paws using a plethysmometer (Stoelting). Briefly, the rat is gently held under the arms with one hand, and its ankle is stabilized with the other hand, each paw is dipped into a known volume of fluid for approximately one second (i.e. sufficient time to obtain a stable reading) and the total fluid displacement is recorded. Vehicle or test compounds are administered to the animals prior to carrageenan administration. A statistically significant reduction in hind paw volume relative to the vehicle-treated control group is interpreted as an anti-inflammatory effect.

Example 87

Spinal Nerve Ligation (SNL) Model

The SNL model (Kim and Chung, 1992, Pain 50 (3):355-63) was used to induce chronic neuropathic pain in rats. Rats were anesthetized with isoflurane, the left L5 transverse process was removed, and the L5 and L6 spinal nerves were tightly ligated with 6-0 silk suture. The wound was then closed with internal sutures and external staples. Following at least seven days post SNL, baseline, post-injury and post-treatment values for non-noxious mechanical sensitivity were evaluated using eight Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al., 1994, J. Neurosci. Meth., 53 (1):55-63). Animals were placed on a perforated metallic platform and allowed to acclimate to their surroundings for a minimum of thirty minutes before testing.

Rat L5/L6 SNL model (n=6/group; mean±sem). Sensitivity to non-noxious mechanical stimuli was tested before and at various time points following oral administration of compound (36). The mean and standard error of the mean (SEM) were determined for the injured paw in each treatment group. Since this stimulus is normally not considered painful, significant injury-induced increases in responsiveness in this test are interpreted as a measure of mechanical allodynia. FIG. 1 shows results obtained with compound (36) administered orally doses of 3 mg/kg, 10 mg/kg and 30 mg/kg as compared with gabapentin administered at 200 mg/kg as positive control.

The texts of the references cited in this specification are incorporated herein by reference in their entireties. In the event that a definition of a term as incorporated by reference differs from the meaning defined herein, then the meaning provided herein is intended. The examples provided herein are for illustration purposes only and are not to be interpreted as limiting the scope of the invention, the full scope of which will be immediately recognized by those of skill in the art.

What is claimed is:
1. A compound having the structure of formula I:

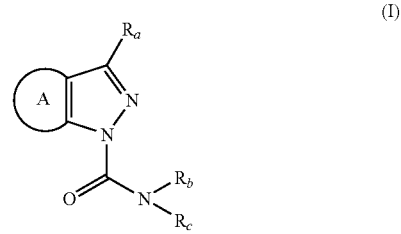

or a pharmaceutically acceptable salt, acid salt, stereoisomer or hydrate thereof, wherein:
the ring moiety A is selected from the group consisting of:

-continued

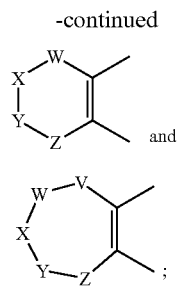

wherein one of V, W, X, Y and Z is O and all others are each $CH_2$;

$R_a$ is selected from the group consisting of $C_1$-$C_8$ alkyl, $C_3$-$C_8$ cycloalkyl, $C_4$-$C_8$ cycloalkenyl, $(CH_2)_p$aryl, $(CH_2)_p$-linked 4-, 5-, 6-, 7-, 8-, 9- and 10-membered heterocyclyl; wherein the $C_1$-$C_8$ alkyl, $C_3$-$C_8$ cycloalkyl, $C_4$-$C_8$ cycloalkenyl, aryl, 4-, 5-, 6-, 7-, 8-, 9- and 10-membered heterocyclyl of $R_a$ are each optionally substituted with one to four substituents independently selected from the group consisting of halo, OH, oxo, $NH_2$, $NO_2$, CN, COOH, $OCF_3$, $CF_3$, $C_1$-$C_6$ alkyl, $C_1$-$C_4$ alkoxy, $C_4$-$C_8$ alkenyl, $C_3$-$C_6$ cycloalkyl, aryl and 4-, 5-, 6-, 7-, 8-, 9- and 10-membered heterocyclyl;

$R_b$ is selected from the group consisting of H, and $C_1$-$C_6$ alkyl optionally substituted with one to four substituents independently selected from the group consisting of $C_1$-$C_4$ alkoxy, halo, OH, $NH_2$ and CN;

$R_c$ is $CR_dR_eR_f$;

$R_d$ is selected from the group consisting of H, $C_1$-$C_6$ alkyl, $C_3$-$C_8$ cycloalkyl, $(CH_2)_p$aryl, $(CH_2)_p$-linked 4-, 5-, 6-, 7-, 8-, 9- and 10-membered heterocyclyl; wherein the $C_1$-$C_6$ alkyl, $C_3$-$C_8$ cycloalkyl, $(CH_2)_p$aryl, $(CH_2)_p$-linked 4-, 5-, 6-, 7-, 8-, 9- and 10-membered heterocyclyl of $R_d$ are optionally substituted with one to four substituents independently selected from the group consisting of $C_1$-$C_4$ alkyl, $C_1$-$C_4$ alkoxy, $C_1$-$C_4$ hydroxyalkyl, $C_1$-$C_4$ haloalkyl, $C_1$-$C_4$ haloalkoxy, aryl, halo, OH, $NR_1R_2$, CN, $NO_2$, and $CONR_1R_2$;

$R_e$ is selected from the group consisting of $COR_3$, $CONR_3R_4$, $CSNR_3R_4$, $COOR_3$, $SOR_3$, $SO_2R_3$, $SO_2NR_3R_4$, $NR_3SO_2R_4$ and $NR_3COR_4$;

$R_f$ is selected from the group consisting of H, $C_1$-$C_6$ alkyl and $C_1$-$C_8$ hydroxyalkyl;

each instance of $R_1$ and $R_2$ is independently selected from the group consisting of H, $C_1$-$C_6$ alkyl, $C_2$-$C_6$ alkenyl, $C_3$-$C_8$ alkynyl and $C_3$-$C_8$ cycloalkyl, wherein the $C_1$-$C_6$ alkyl, $C_2$-$C_6$ alkenyl, $C_3$-$C_8$ alkynyl and $C_3$-$C_8$ cycloalkyl of each $R_1$ and $R_2$ is optionally substituted with one to four substituents independently selected from the group consisting of $C_1$-$C_4$ alkyl, $C_1$-$C_4$ alkoxy, halo, OH, oxo, $NO_2$, CN, $OCF_3$, $CF_3$, $NR_3R_4$, $CONR_3R_4$, $COOR_3$, $SOR_3$, $SO_2R_3$, $SO_2NR_3R_4$, $NR_3COR_4$, and $NR_3SO_2R_4$;

$R_3$ and $R_4$ are each independently selected from the group consisting of H, $C_1$-$C_8$ alkyl, $C_1$-$C_8$ alkoxy, $C_1$-$C_8$ alkoxyalkyl, $C_3$-$C_8$ cycloalkyl, $C_4$-$C_8$ cycloalkenyl, $(CH_2)_p$aryl, $(CH_2)_p$-linked 4-, 5-, 6-, 7-, 8-, 9- and 10-membered heterocyclyl; wherein the $C_1$-$C_8$ alkyl, $C_3$-$C_8$ cycloalkyl, $C_4$-$C_8$ cycloalkenyl, aryl, and 4-, 5-, 6-, 7-, 8-, 9- and 10-membered heterocyclyl of $R_3$ and $R_4$ are each optionally substituted with one to four substituents independently selected from the group consisting of halo, OH, oxo, $NR_5R_6$, $NO_2$, CN, $OCF_3$, $CF_3$, $C_1$-$C_6$ alkyl, $C_1$-$C_4$ alkoxy, $C_1$-$C_4$ hydroxyalkyl, $CONR_5R_6$, $SOR_5$, $SO_2R_5$, $SO_2NR_5R_6$, $COOR_5$, $NR_5COR_6$ and $NR_5SO_2R_6$;

alternatively, $R_3$ and $R_4$ taken together with the nitrogen atom to which they are bonded form a heterocyclyl selected from the group consisting of 4-, 5-, 6-, 7-, 8-, 9- and 10-membered heterocyclyl optionally substituted with one to four substituents independently selected from the group consisting of halo, OH, oxo, $NR_5R_6$, $NO_2$, CN, $OCF_3$, $CF_3$, $C_1$-$C_6$ alkyl, $C_1$-$C_4$ alkoxy, $C_1$-$C_4$ hydroxyalkyl, $CONR_5R_6$, $SOR_5$, $SO_2R_5$, $SO_2NR_5R_6$, $COOR_5$, $NR_5COR_6$ and $NR_5SO_2R_6$;

wherein each instance of $R_5$ and $R_6$ is independently selected from the group consisting of H, $C_1$-$C_4$ alkyl, aryl and 4-, 5-, 6-, 7-, 8-, 9- and 10-membered heterocyclyl, wherein the alkyl, aryl and heterocyclyl are each independently optionally substituted with one to three substituents selected from the group consisting of $C_1$-$C_4$ alkyl, $C_1$-$C_4$ alkoxy, halo, OH, oxo, $NO_2$, $NH_2$, CN, $OCF_3$ and $CF_3$; and wherein each instance of p is independently 0 or an integer from 1 to 6.

2. The compound according to claim 1, wherein:

$R_a$ is selected from the group consisting of $C_1$-$C_8$ alkyl, $C_3$-$C_8$ cycloalkyl, $C_4$-$C_8$ cycloalkenyl, $(CH_2)_p$aryl and $(CH_2)_p$-linked 4-, 5-, 6-, 7-, 8-, 9- and 10-membered heterocyclyl; wherein the alkyl, cycloalkyl, cycloalkenyl, aryl and heterocyclyl of $R_a$ are each optionally substituted with one to four substituents independently selected from the group consisting of halo, OH, oxo, $NH_2$, $NO_2$, CN, COOH, $OCF_3$, $CF_3$, $C_1$-$C_6$ alkyl, and $C_1$-$C_4$ alkoxy;

$R_b$ is selected from the group consisting of H and optionally substituted $C_1$-$C_4$ alkyl;

$R_d$ is selected from the group consisting of $C_1$-$C_6$ alkyl, $C_3$-$C_8$ cycloalkyl, aryl, 4-, 5-, 6-, 7-, 8-, 9- and 10-membered heterocyclyl; wherein the alkyl, cycloalkyl, aryl, and heterocyclyl of $R_d$ are optionally substituted with one to three substituents independently selected from the group consisting of $C_1$-$C_4$ alkyl, $C_1$-$C_4$ alkoxy, $C_1$-$C_4$ hydroxyalkyl, aryl, halo, OH, $NH_2$, CN, and $NO_2$;

$R_f$ is H or $C_1$-$C_6$ alkyl;

wherein each instance of p is independently 0 or an integer from 1 to 3.

3. The compound according to claim 1, wherein $R_a$ is selected from the group consisting of aryl, $C_3$-$C_8$ cycloalkyl, $C_4$-$C_8$ cycloalkenyl, 4-, 5-, 6-, 7-, 8-, 9- and 10-membered heterocyclyl; wherein the aryl, cycloalkyl, cycloalkenyl and heterocyclyl of $R_a$ are each optionally substituted with one to four substituents independently selected from the group consisting of halo, OH, CN, $OCF_3$, $CF_3$, $C_1$-$C_6$ alkyl, and $C_1$-$C_4$ alkoxy.

4. The compound according to claim 2, wherein $R_d$ is selected from the group consisting of $C_1$-$C_6$ alkyl, $C_3$-$C_8$ cycloalkyl; wherein the alkyl and cycloalkyl of $R_d$ are optionally substituted with one to three substituents independently selected from the group consisting of $C_1$-$C_4$ alkyl, $C_1$-$C_4$ alkoxy, $C_1$-$C_4$ hydroxyalkyl, halo, OH, $NH_2$, CN, and $NO_2$;

$R_e$ is selected from the group consisting of $COR_3$, $CONR_3R_4$, $COOR_3$, $NR_3COR_4$ and $SO_2NR_3R_4$;

$R_f$ is H.

5. The compound according to claim 2, wherein
$R_d$ is selected from the group consisting of aryl, 4-, 5-, 6-, 7-, 8-, 9- and 10-membered heterocyclyl; wherein the aryl, and heterocyclyl of $R_d$ are optionally substituted with one to three substituents independently selected from the group consisting of $C_1$-$C_4$ alkyl, $C_1$-$C_4$ alkoxy, $C_1$-$C_4$ hydroxyalkyl, aryl, halo, OH, $NH_2$, CN, and $NO_2$;
$R_e$ is selected from the group consisting of $COR_3$, $CONR_3R_4$, $COOR_3$, $NR_3COR_4$;
$R_f$ is H.

6. The compound according to claim 1, wherein $R_b$ is H or $C_1$-$C_6$ alkyl; wherein the $C_1$-$C_6$ alkyl of $R_b$ is optionally substituted with one to three substituents independently selected from halo and hydroxyl.

7. The compound according to claim 1, wherein:
$R_a$ is selected from the group consisting of $C_3$-$C_8$ cycloalkyl, $C_4$-$C_8$ cycloalkenyl and aryl; wherein the cycloalkyl, cycloalkenyl and aryl are optionally substituted with one to four substituents independently selected from the group consisting of halo, OH, CN, $OCF_3$, $CF_3$, $C_1$-$C_6$ alkyl and $C_1$-$C_4$ alkoxy;
$R_b$ is H or $C_1$-$C_4$ alkyl;
$R_d$ is selected from the group consisting of H and $C_1$-$C_6$ alkyl; wherein the $C_1$-$C_6$ alkyl of $R_d$ is optionally substituted with one to four substituents independently selected from the group consisting of $C_1$-$C_4$ alkoxy, $C_1$-$C_4$ hydroxyalkyl, halo, CN, and OH;
$R_f$ is H or Me.

8. The compound according to claim 7, wherein $R_a$ is phenyl optionally substituted with one to four substituents independently selected from the group consisting of halo, OH, CN, $OCF_3$, $CF_3$, $C_1$-$C_4$ alkyl, and $C_1$-$C_4$ alkoxy.

9. The compound according to claim 1, wherein:
$R_d$ is selected from the group consisting of H, $C_1$-$C_6$ alkyl, aryl, 4-, 5-, 6-, 7-, 8-, 9- and 10-membered heterocyclyl; wherein the alkyl, aryl and heterocyclyl of $R_d$ are optionally substituted with one to four substituents independently selected from the group consisting of $C_1$-$C_4$ alkyl, $C_1$-$C_4$ alkoxy, $C_1$-$C_4$ hydroxyalkyl, aryl, halo, OH, $NH_2$, CN, and $NO_2$;
$R_e$ is selected from the group consisting of $COR_3$, $CONR_3R_4$, $COOR_3$, $NR_3COR_4$ and $SO_2NR_3R_4$; and
$R_f$ is H or $C_1$-$C_4$ alkyl.

10. The compound according to claim 2, wherein $R_d$ is H or optionally substituted $C_1$-$C_6$ alkyl.

11. The compound according to claim 10, wherein $R_e$ is $CONR_3R_4$ or $COOR_3$.

12. The compound according to claim 11, wherein $R_3$ and $R_4$ are each independently selected from the group consisting of H, $C_1$-$C_8$ alkyl, $C_3$-$C_8$ cycloalkyl, $(CH_2)_p$-linked 4-, 5-, 6-, 7- and 8-membered heterocyclyl; wherein the alkyl, cycloalkyl and heterocyclyl of $R_3$ and $R_4$ are each optionally substituted with one to three substituents independently selected from the group consisting of halo, OH, $NH_2$, CN, $COOR_5$, $CONR_5R_6$, $SO_2NR_5R_6$, $SO_2R_5$, $CF_3$, $C_1$-$C_6$ alkyl and $C_1$-$C_6$ alkoxy;
alternatively, $R_3$ and $R_4$ taken together with the nitrogen atom to which they are bonded form an optionally substituted 4-, 5-, 6-, 7- or 8-membered heterocyclyl.

13. The compound according to claim 12, wherein $R_3$ and $R_4$ are each independently selected from the group consisting of H, $C_1$-$C_4$ alkyl and $(CH_2)_p$-linked heterocyclyl, wherein the $C_1$-$C_4$ alkyl and $(CH_2)_p$-linked heterocyclyl are optionally substituted with one to three substituents.

14. The compound according to claim 3, wherein $R_a$ is aryl optionally substituted with one to four substituents.

15. The compound according to claim 3, wherein $R_a$ is selected from the group consisting of 4-, 5-, 6-, 7-, 8-, 9- and 10-membered heterocyclyl optionally substituted with one to four substituents.

16. The compound according to claim 1, having a structure selected from the group consisting of
(S)-3-(3,4-difluorophenyl)-N-(3,3-dimethyl-1-(methylamino)-1-oxobutan-2-yl)-6,7-dihydropyrano[4,3-c]pyrazole-1(4H)-carboxamide (compound 28),
(S)—N-(3,3-dimethyl-1-(methylamino)-1-oxobutan-2-yl)-3-(2,4,5-trifluorophenyl)-6,7-dihydropyrano[4,3-c]pyrazole-1(4H)-carboxamide (compound 30),
N—((S)-1-((S)-3-hydroxypyrrolidin-1-yl)-3,3-dimethyl-1-oxobutan-2-yl)-3-(2,4,5-trifluorophenyl)-6,7-dihydropyrano[4,3-c]pyrazole-1(4H)-carboxamide (compound 31),
(S)—N-(3,3-dimethyl-1-(4-methylpiperazin-1-yl)-1-oxobutan-2-yl)-3-(2,4,5-trifluorophenyl)-6,7-dihydropyrano[4,3-c]pyrazole-1(4H)-carboxamide (compound 32),
(S)—N-(1-hydroxy-3,3-dimethylbutan-2-yl)-3-(2,4,5-trifluorophenyl)-6,7-dihydropyrano[4,3-c]pyrazole-1(4H)-carboxamide (compound 33),
(S)-methyl 3,3-dimethyl-2-(3-(2,4,5-trifluorophenyl)-1,4,6,7-tetrahydropyrano[4,3-c]pyrazole-1-carboxamido) butanoate (compound 34),
(S)—N-(1-(2-hydroxyethylamino)-3,3-dimethyl-1-oxobutan-2-yl)-3-(2,4,5-trifluorophenyl)-6,7-dihydropyrano[4,3-c]pyrazole-1(4H)-carboxamide (compound 35),
(S)—N-(1-(2-hydroxyethylamino)-3,3-dimethyl-1-oxobutan-2-yl)-3-(3,4-difluorophenyl)-6,7-dihydropyrano[4,3-c]pyrazole-1(4H)-carboxamide (compound 36),
N-(4-tert-butylthiazol-2-yl)-3-(3,4-difluorophenyl)-6,7-dihydropyrano[4,3-c]pyrazole-1(4H)-carboxamide (compound 56),
N-(4-tert-butylthiazol-2-yl)-3-(3,4-difluorophenyl)-6,7-dihydropyrano[4,3-c]pyrazole-1(4H)-carboxamide (compound 57),
3-(3,4-difluorophenyl)-N—((S)-1-((S)-3-hydroxypyrrolidin-1-yl)-3,3-dimethyl-1-oxobutan-2-yl)-6,7-dihydropyrano[4,3-c]pyrazole-1(4H)-carboxamide (compound 60),
(S)-3-(5-chloro-2-fluorophenyl)-N-(1-(2-hydroxyethylamino)-3,3-dimethyl-1-oxobutan-2-yl)-6,7-dihydropyrano[4,3-c]pyrazole-1(4H)-carboxamide (compound 86),
(S)-3-(2,5-difluorophenyl)-N-(1-(2-hydroxyethylamino)-3,3-dimethyl-1-oxobutan-2-yl)-6,7-dihydropyrano[4,3-c]pyrazole-1(4H)-carboxamide (compound 87),
(S)-3-(4-chloro-2-fluorophenyl)-N-(1-(2-hydroxyethylamino)-3,3-dimethyl-1-oxobutan-2-yl)-6,7-dihydropyrano[4,3-c]pyrazole-1(4H)-carboxamide (compound 88),
(S)-3-(3,4-difluorophenyl)-N-(1-(2-hydroxyethylamino)-3,3-dimethyl-1-oxobutan-2-yl)-4,5-dihydropyrano[3,4-c]pyrazole-1(7H)-carboxamide (compound 95),
(S)-3-(5-chloro-2-fluorophenyl)-N-(1-(2-hydroxyethylamino)-3,3-dimethyl-1-oxobutan-2-yl)-4,5-dihydropyrano[3,4-c]pyrazole-1(7H)-carboxamide (compound 96),
(S)—N-(1-(2-hydroxyethylamino)-3,3-dimethyl-1-oxobutan-2-yl)-3-(2,4,5-trifluorophenyl)-4,5-dihydropyrano[3,4-c]pyrazole-1(7H)-carboxamide (compound 97) and (S)—N-(1-amino-3,3-dimethyl-1-oxobutan-2-yl)-3-(3,4-difluorophenyl)-6,7-dihydropyrano[4,3-c]pyrazole-1(4H)-carboxamide (compound 99).

17. A pharmaceutical composition comprising a compound according to claim 1 and a pharmaceutically acceptable diluent, excipient or carrier.

18. A method of treatment of a cannabinoid receptor-associated disease or condition in a mammalian subject, wherein the disease or condition is selected from the group consisting of pain, inflammation, and pruritis, the method comprising administering to the subject an effective amount of a compound according to claim 1.

19. The method according to claim 18, wherein the pain is selected from the group consisting of visceral pain, somatic pain, cutaneous pain, neuropathic pain and inflammatory pain.

\* \* \* \* \*